(12) United States Patent
Kinrade et al.

(10) Patent No.: US 7,078,187 B2
(45) Date of Patent: Jul. 18, 2006

(54) MELANIN CONCENTRATING HORMONE RECEPTORS

(75) Inventors: Michele Bennett Kinrade, Northford, CT (US); Robbin M. Brodbeck, Madison, CT (US); James E. Krause, Madison, CT (US)

(73) Assignee: Neurogen Corporation, Branford, CT (US)

(*) Notice: Subject to any disclaimer, the term of this patent is extended or adjusted under 35 U.S.C. 154(b) by 653 days.

(21) Appl. No.: 10/126,764

(22) Filed: Apr. 18, 2002

(65) Prior Publication Data

US 2003/0166834 A1 Sep. 4, 2003

Related U.S. Application Data

(60) Provisional application No. 60/284,835, filed on Apr. 19, 2001.

(51) Int. Cl.
C12N 15/00 (2006.01)
C12N 15/85 (2006.01)
C12N 15/63 (2006.01)
C07H 21/04 (2006.01)

(52) U.S. Cl. .................... 435/69.1; 435/69.7; 435/325; 435/252.3; 435/254.11; 435/254.2; 435/320.1; 536/23.4; 536/23.5

(58) Field of Classification Search ............. 435/320.1, 435/325, 252.3, 254.11, 254.2; 536/23.5; 530/350
See application file for complete search history.

(56) References Cited

U.S. PATENT DOCUMENTS

| | | |
|---|---|---|
| 6,008,012 A | 12/1999 | Bergsma et al. |
| 6,033,872 A | 3/2000 | Bergsma et al. |
| 6,221,613 B1 | 4/2001 | Salon et al. |
| 6,221,616 B1 | 4/2001 | Salon et al. |
| 6,291,195 B1 | 9/2001 | Salon et al. |
| 6,362,326 B1 | 3/2002 | Sathe et al. |
| 6,723,552 B1 | 4/2004 | Salon et al. |
| 2002/0038007 A1 | 3/2002 | Ames et al. |
| 2003/0082623 A1 | 5/2003 | Borowsky et al. |
| 2004/0038855 A1 | 2/2004 | Salon et al. |
| 2004/0248129 A1 | 12/2004 | Tan et al. |

FOREIGN PATENT DOCUMENTS

| | | |
|---|---|---|
| EP | 848060 A2 | 6/1998 |
| WO | WO 96/18651 | 6/1996 |
| WO | WO 99/28492 | 6/1999 |
| WO | WO 00/39279 | 7/2000 |
| WO | WO 00/40725 | 7/2000 |
| WO | WO 00/49170 | 8/2000 |
| WO | WO 00/70347 | 11/2000 |
| WO | WO 00/75166 | 12/2000 |
| WO | WO 01/05947 | 1/2001 |
| WO | WO 01/07606 | 2/2001 |
| WO | WO 01/43759 | 6/2001 |
| WO | WO 01/68706 | 9/2001 |
| WO | WO 02/02744 | 1/2002 |
| WO | WO 02/03070 | 1/2002 |
| WO | WO 02/08290 | 1/2002 |
| WO | WO 02/36076 | 5/2002 |
| WO | WO 03/027239 | 4/2003 |
| WO | WO 03/027240 | 4/2003 |

OTHER PUBLICATIONS

Kolakowski et al., "Characterization of a human gene related to genes encoding somatostatin receptors," FEBS Letters 398 (1996) 253-258.
Lakaye et al., "Cloning of the rat brain cDNA encoding for the SLC-1 G protein-coupled receptor reveals the presence of an intron in the gene," Biochimica et Biophysica Acta 1401 (1998) 216-220.
Chambers et al., "Melanin-concentrating hormone is the cognate ligand for the orphan G-protein-coupled receptor SLC-1," Nature 400 (1999) 261-265.
Saito et al., "Molecular characterization of the melanin-concentrating-hormone receptor," Nature 400 (1999) 265-269.

*Primary Examiner*—Ruixiang Li
(74) *Attorney, Agent, or Firm*—Ann T. Kadlecek; Seth A. Fidel

(57) ABSTRACT

Isolated polynucleotides encoding monkey Melanin Concentrating Hormone (MCH) Type 1 receptors and chimeric polypeptides are provided. Vectors and cells for recombinant expression of such MCH1R polypeptides, and isolated MCH1R polypeptides are also provided. MCH1R polynucleotides and polypeptides may be used, for example, to identify compounds that specifically interact with MCH receptor. Such compounds find use within therapies for humans and animals afflicted with conditions associated with MCH receptor activation.

24 Claims, 4 Drawing Sheets

|              | 1.........10 | .........20 | .........30 | .........40 |
|---|---|---|---|---|
| c.mac MCH1R ext | MSVRAAKEGV | GRAVGLGGGS | GCQAAKEDPL | PDCGACAPGQ |
| c.mac MCH1R | ---------- | ---------- | ---------- | ---------- |
| seq ID 2 6,008,012 | MLCPSKTDGS | GHSGRIHQET | HGEG-KRDKI | SNSEGRE--N |
| human MCH1R | ---------- | ---------- | ---------- | ---------- |
| rat MCH1R | ---------- | ---------- | ---------- | ---------- |

|              | .........50 | .........60 | .........70 | .........80 |
|---|---|---|---|---|
| c.mac MCH1R ext | GGRRWRLPQP | AWVEGSSAWL | WEPATGTGWM | DLEASLLPTG |
| c.mac MCH1R | ---------- | ---------- | ---------M | DLEASLLPTG |
| seq ID 2 6,008,012 | GGRGFQMN-- | ---GGS---- | --------LE | AEHASRMSVL |
| human MCH1R | ---------- | ---------- | ---------M | DLEASLLPTG |
| rat MCH1R | ---------- | ---------- | ---------M | DLQTSLLSTG |

|              | .........90 | ........100 | ........110 | ........120 |
|---|---|---|---|---|
| c.mac MCH1R ext | PNTSNTSDGP | DNLTSAGSPP | RSGSVSYINI | IMPSVFGTIC |
| c.mac MCH1R | PNTSNTSDGP | DNLTSAGSPP | RSGSVSYINI | IMPSVFGTIC |
| seq ID 2 6,008,012 | RAKPMSNSQR | LLLLSPGSPP | RTGSISYINI | IMPSVFGTIC |
| human MCH1R | PNASNTSDGP | DNLTSAGSPP | RTGSISYINI | IMPSVFGTIC |
| rat MCH1R | PNASNISDGQ | DNLTLPGSPP | RTGSVSYINI | IMPSVFGTIC |

|              | ........130 | ........140 | ........150 | ........160 |
|---|---|---|---|---|
| c.mac MCH1R ext | LLGIIGNSMV | IFAVVKKSKL | HWCNNVPDIF | IINLSVVDLL |
| c.mac MCH1R | LLGIIGNSMV | IFAVVKKSKL | HWCNNVPDIF | IINLSVVDLL |
| seq ID 2 6,008,012 | LLGIIGNSTV | IFAVVKKSKL | HWCNNVPDIF | IINLSVVDLL |
| human MCH1R | LLGIIGNSTV | IFAVVKKSKL | HWCNNVPDIF | IINLSVVDLL |
| rat MCH1R | LLGIVGNSTV | IFAVVKKSKL | HWCSNVPDIF | IINLSVVDLL |

|              | ........170 | ........180 | ........190 | ........200 |
|---|---|---|---|---|
| c.mac MCH1R ext | FLLGMPFMIH | QLMGNGVWHF | GETMCTLITA | MDANSQFTST |
| c.mac MCH1R | FLLGMPFMIH | QLMGNGVWHF | GETMCTLITA | MDANSQFTST |
| seq ID 2 6,008,012 | FLLGMPFMIH | QLMGNGVWHF | GETMCTLITA | MDANSQFTST |
| human MCH1R | FLLGMPFMIH | QLMGNGVWHF | GETMCTLITA | MDANSQFTST |
| rat MCH1R | FLLGMPFMIH | QLMGNGVWHF | GETMCTLITA | MDANSQFTST |

|              | ........210 | ........220 | ........230 | ........240 |
|---|---|---|---|---|
| c.mac MCH1R ext | YILTAMAIDR | YLATVHPISS | TKFRKPSVAT | LVICLLWALS |
| c.mac MCH1R | YILTAMAIDR | YLATVHPISS | TKFRKPSVAT | LVICLLWALS |
| seq ID 2 6,008,012 | YILTAMAIDR | YLATVHPISS | TKFRKPSVAT | LVICLLWALS |
| human MCH1R | YILTAMAIDR | YLATVHPISS | TKFRKPSVAT | LVICLLWALS |
| rat MCH1R | YILTAMTIDR | YLATVHPISS | TKFRKPSMAT | LVICLLWALS |

Figure 1A

```
                           ........250  ........260  ........270  ........280
c.mac MCH1R ext            FISITPVWLY   ARLIPFPGGA   VGCGIRLPNP   DTDLYWFTLY
c.mac MCH1R                FISITPVWLY   ARLIPFPGGA   VGCGIRLPNP   DTDLYWFTLY
seq ID 2 6,008,012         FISITPVWLY   ARLIPFPGGA   VGCGIRLPNP   DTDLYWFTLY
human MCH1R                FISITPVWLY   ARLIPFPGGA   VGCGIRLPNP   DTDLYWFTLY
rat MCH1R                  FISITPVWLY   ARLIPFPGGA   VGCGIRLPNP   DTDLYWFTLY ........290  ........300  ........310  ........320
c.mac MCH1R ext            QFFLAFALPF   VVITAAYVRI   LQRMTSSVAP   ASQRSIRLRT
c.mac MCH1R                QFFLAFALPF   VVITAAYVRI   LQRMTSSVAP   ASQRSIRLRT
seq ID 2 6,008,012         QFFLAFALPF   VVITAAYVRI   LQRMTSSVAP   ASQRSIRLRT
human MCH1R                QFFLAFALPF   VVITAAYVRI   LQRMTSSVAP   ASQRSIRLRT
rat MCH1R                  QFFLAFALPF   VVITAAYVKI   LQRMTSSVAP   ASQRSIRLRT ........330  ........340  ........350  ........360
c.mac MCH1R ext            KRVTRTAIAI   CLVFFVCWAP   YYVLQLTQLS   ISRPTLTFVY
c.mac MCH1R                KRVTRTAIAI   CLVFFVCWAP   YYVLQLTQLS   ISRPTLTFVY
seq ID 2 6,008,012         KRVTRTAIAI   CLVFFVCWAP   YYVLQLTQLS   ISRPTLTFVY
human MCH1R                KRVTRTAIAI   CLVFFVCWAP   YYVLQLTQLS   ISRPTLTFVY
rat MCH1R                  KRVTRTAIAI   CLVFFVCWAP   YYVLQLTQLS   ISRPTLTFVY ........370  ........380  ........390  ........400
c.mac MCH1R ext            LYNAAISLGY   ANSCLNPFVY   IVLCETFRKR   LVLSVKPAAQ
c.mac MCH1R                LYNAAISLGY   ANSCLNPFVY   IVLCETFRKR   LVLSVKPAAQ
seq ID 2 6,008,012         LYNAAISLGY   ANSCLNPFVY   IVLCETFRKR   LVLSVKPAAQ
human MCH1R                LYNAAISLGY   ANSCLNPFVY   IVLCETFRKR   LVLSVKPAAQ
rat MCH1R                  LYNAAISLGY   ANSCLNPFVY   IVLCETFRKR   LVLSVKPAAQ ........410  ........420  ........430  ........440
c.mac MCH1R ext            GQLRAVSNAQ   TADEERTESK   GT
c.mac MCH1R                GQLRAVSNAQ   TADEERTESK   GT
seq ID 2 6,008,012         GQLRAVSNAQ   TADEERTESK   GT
human MCH1R                GQLRAVSNAQ   TADEERTESK   GT
rat MCH1R                  GQLRTVSNAQ   TADEERTESK   GT
```

Figure 1B

|                | 1.........10 | .........20 | .........30 | .........40 |
|----------------|------------|------------|------------|------------|
| c.mac MCH1R    | ---------- | ---------- | ---------- | ---------- |
| c.mac MCH1R ext| MSVRAAKEGV | GRAVGLGGGS | GCQAAKEDPL | PDCGACAPGQ |
| AR169785 hMCH1 | MSVGAMKKGV | GRAVGLGGGS | GCQATEEDPL | PDCGACAPGQ |

|                | .........50 | .........60 | .........70 | .........80 |
|----------------|------------|------------|------------|------------|
| c.mac MCH1R    | ---------- | ---------- | ---------M | DLEASLLPTG |
| c.mac MCH1R ext| GGRRWRLPQP | AWVEGSSAWL | WEPATGTGWM | DLEASLLPTG |
| AR169785 hMCH1 | GGRRWRLPQP | AWVEGSSAWL | WEQATGTGWM | DLEASLLPTG |

|                | .........90 | ........100 | ........110 | ........120 |
|----------------|------------|------------|------------|------------|
| c.mac MCH1R    | PNTSNTSDGP | DNLTSAGSPP | RSGSVSYINI | IMPSVFGTIC |
| c.mac MCH1R ext| PNTSNTSDGP | DNLTSAGSPP | RSGSVSYINI | IMPSVFGTIC |
| AR169785 hMCH1 | PNASNTSDGP | DNLTSAGSPP | RTGSISYINI | IMPSVFGTIC |

|                | ........130 | ........140 | ........150 | ........160 |
|----------------|------------|------------|------------|------------|
| c.mac MCH1R    | LLGIIGNSMV | IFAVVKKSKL | HWCNNVPDIF | IINLSVVDLL |
| c.mac MCH1R ext| LLGIIGNSMV | IFAVVKKSKL | HWCNNVPDIF | IINLSVVDLL |
| AR169785 hMCH1 | LLGIIGNSTV | IFAVVKKSKL | HWCNNVPDIF | IINLSVVDLL |

|                | ........170 | ........180 | ........190 | ........200 |
|----------------|------------|------------|------------|------------|
| c.mac MCH1R ext| FLLGMPFMIH | QLMGNGVWHF | GETMCTLITA | MDANSQFTST |
| c.mac MCH1R ext| FLLGMPFMIH | QLMGNGVWHF | GETMCTLITA | MDANSQFTST |
| AR169785 hMCH1 | FLLGMPFMIH | QLMGNGVWHF | GETMCTLITA | MDANSQFTST |

|                | ........210 | ........220 | ........230 | ........240 |
|----------------|------------|------------|------------|------------|
| c.mac MCH1R    | YILTAMAIDR | YLATVHPISS | TKFRKPSVAT | LVICLLWALS |
| c.mac MCH1R ext| YILTAMAIDR | YLATVHPISS | TKFRKPSVAT | LVICLLWALS |
| AR169785 hMCH1 | YILTAMAIDR | YLATVHPISS | TKFRKPSVAT | LVICLLWALS |

Figure 2A

```
                  ........250   ........260   ........270   ........280
c.mac MCH1R       FISITPVWLY    ARLIPFPGGA    VGCGIRLPNP    DTDLYWFTLY
c.mac MCH1R ext   FISITPVWLY    ARLIPFPGGA    VGCGIRLPNP    DTDLYWFTLY
AR169785 hMCH1    FISITPVWLY    ARLIPFPGGA    VGCGIRLPNP    DTDLYWFTLY ........290   ........300   ........310   ........320
c.mac MCH1R       QFFLAFALPF    VVITAAYVRI    LQRMTSSVAP    ASQRSIRLRT
c.mac MCH1R ext   QFFLAFALPF    VVITAAYVRI    LQRMTSSVAP    ASQRSIRLRT
AR169785 hMCH1    QFFLAFALPF    VVITAAYVRI    LQRMTSSVAP    ASQRSIRLRT ........330   ........340   ........350   ........360
c.mac MCH1R       KRVTRTAIAI    CLVFFVCWAP    YYVLQLTQLS    ISRPTLTFVY
c.mac MCH1R ext   KRVTRTAIAI    CLVFFVCWAP    YYVLQLTQLS    ISRPTLTFVY
AR169785 hMCH1    KRVTRTAIAI    CLVFFVCWAP    YYVLQLTQLS    ISRPTLTFVY ........370   ........380   ........390   ........400
c.mac MCH1R       LYNAAISLGY    ANSCLNPFVY    IVLCETFRKR    LVLSVKPAAQ
c.mac MCH1R ext   LYNAAISLGY    ANSCLNPFVY    IVLCETFRKR    LVLSVKPAAQ
AR169785 hMCH1    LYNAAISLGY    ANSCLNPFVY    IVLCETFRKR    LVLSVKPAAQ ........410   ........420   ........430   ........440
c.mac MCH1R       GQLRAVSNAQ    TADEERTESK    GT
c.mac MCH1R ext   GQLRAVSNAQ    TADEERTESK    GT
AR169785 hMCH1    GQLRAVSNAQ    TADEERTESK    GT
```

Figure 2B

SEQUENCE LISTING

<160> NUMBER OF SEQ ID NOS: 58

<210> SEQ ID NO 1
<211> LENGTH: 1062
<212> TYPE: DNA
<213> ORGANISM: Macaca fascicularis

<400> SEQUENCE: 1

```
atggacctgg aagcctcgct gctgcccact ggtcccaaca ccagcaacac ctctgatggc      60
cccgataacc tcacctcggc aggatcacct cctcgctcag ggagcgtctc ctacatcaac     120
atcatcatgc cttcggtgtt cggcaccatc tgcctcctgg gcatcatcgg aactccatg     180
gtcatcttcg cggtcgtgaa gagtccaag ctgcactggt gcaacaatgt ccccgacatc     240
ttcatcatca acctctcggt ggtggatctc ctctttctcc tgggcatgcc cttcatgatc     300
caccagctca tgggcaatgg ggtgtggcac tttggggaga ccatgtgcac cctcatcacg     360
gccatggatg ccaatagtca gttcaccagc acctacatcc tgaccgccat ggccattgac     420
cgctacctgg ccaccgtcca ccccatctct ccacaaagt tccggaagcc ctctgtggcc     480
accctggtga tctgcctcct gtgggccctc ccttcatca gcatcacccc cgtgtggttg     540
tatgccagac tcatcccctt ccaggaggt gcagtgggct gcggcatccg cttgcccaac     600
ccggacactg acctttactg gttcaccctg taccagtttt tcctggcctt tgccctgccc     660
ttcgtggtca tcacggccgc atacgtgagg atcctgcagc gcatgacgtc ctcagtggcc     720
cccgcctccc agcgcagcat ccggctgcgg acaaagaggg tgacccgcac agccatcgcc     780
atctgcctgg tcttctttgt gtgctgggca ccctactatg tgctacagct gacccagttg     840
tccatcagcc gcccgaccct caccttgtc tacctgtaca atgcggccat cagcttgggc     900
tacgccaaca gctgcctcaa ccccttgtg tacattgtgc tctgcgagac gttccgcaaa     960
cgcttggtcc tttcggtgaa gcctgcagcc caggggcagc ttcgcgctgt cagcaacgct    1020
cagacggctg acgaggagag gacagaaaagc aaaggtacct ga                      1062
```

<210> SEQ ID NO 2
<211> LENGTH: 353
<212> TYPE: PRT
<213> ORGANISM: Macaca fascicularis

<400> SEQUENCE: 2

```
Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
            20                  25                  30

Ser Gly Ser Val Ser Tyr Ile Asn Ile Ile Met Pro Ser Val Phe Gly
        35                  40                  45

Thr Ile Cys Leu Leu Gly Ile Ile Gly Asn Ser Met Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125
```

```
Thr Ser Thr Tyr Ile Leu Thr Ala Met Ala Ile Asp Arg Tyr Leu Ala
        130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
                260                 265                 270

Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
            290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
                340                 345                 350

Thr

<210> SEQ ID NO 3
<211> LENGTH: 6
<212> TYPE: PRT
<213> ORGANISM: Artificial Sequence
<220> FEATURE:
<223> OTHER INFORMATION: His 6x epitope

<400> SEQUENCE: 3

His His His His His His
1               5

<210> SEQ ID NO 4
<211> LENGTH: 8
<212> TYPE: PRT
<213> ORGANISM: Artificial Sequence
<220> FEATURE:
<223> OTHER INFORMATION: FLAG epitope

<400> SEQUENCE: 4

Asp Tyr Lys Asp Asp Asp Asp Lys
1               5

<210> SEQ ID NO 5
<211> LENGTH: 1062
<212> TYPE: DNA
<213> ORGANISM: Homo sapiens

<400> SEQUENCE: 5
```

-continued

```
atggacctgg aagcctcgct gctgcccact ggtcccaatg ccagcaacac ctctgatggc      60
cccgataacc tcacttcggc aggatcacct cctcgcacgg ggagcatctc ctacatcaac     120
atcatcatgc cttcggtgtt cggcaccatc tgcctcctgg gcatcatcgg gaactccacg     180
gtcatcttcg cggtcgtgaa gaagtccaag ctgcactggt gcaacaacgt ccccgacatc     240
ttcatcatca acctctcggt agtagatctc ctctttctcc tgggcatgcc cttcatgatc     300
caccagctca tgggcaatgg ggtgtggcac tttggggaga ccatgtgcac cctcatcacg     360
gccatggatg ccaatagtca gttcaccagc acctacatcc tgaccgccat ggccattgac     420
cgctacctgg ccactgtcca ccccatctct tccacgaagt tccggaagcc ctctgtggcc     480
accctggtga tctgcctcct gtgggccctc tccttcatca gcatcacccc tgtgtggctg     540
tatgccagac tcatcccctt cccaggaggt gcagtgggct gcggcatacg cctgcccaac     600
ccagacactg acctctactg gttcaccctg taccagtttt tcctggcctt tgccctgcct     660
tttgtggtca tcagccgc atacgtgagg atcctgcagc gcatgacgtc ctcagtggcc       720
cccgcctccc agcgcagcat ccggctgcgg acaaagaggg tgacccgcac agccatcgcc     780
atctgtctgg tcttctttgt gtgctgggca ccctactatg tgctacagct gacccagttg     840
tccatcagcc gcccgaccct cacctttgtc tacttataca atgcggccat cagcttgggc     900
tatgccaaca gctgcctcaa cccctttgtg tacatcgtgc tctgtgagac gttccgcaaa     960
cgcttggtcc tgtcggtgaa gctgcagcc caggggcagc ttcgcgctgt cagcaacgct    1020
cagacggctg acgaggagag gacagaaagc aaaggcacct ga                       1062
```

<210> SEQ ID NO 6
<211> LENGTH: 353
<212> TYPE: PRT
<213> ORGANISM: homo sapiens

<400> SEQUENCE: 6

```
Met Asp Leu Glu Ala Ser Leu Leu Pro Thr Gly Pro Asn Ala Ser Asn
1               5                   10                  15

Thr Ser Asp Gly Pro Asp Asn Leu Thr Ser Ala Gly Ser Pro Pro Arg
            20                  25                  30

Thr Gly Ser Ile Ser Tyr Ile Asn Ile Ile Met Pro Ser Val Phe Gly
        35                  40                  45

Thr Ile Cys Leu Leu Gly Ile Ile Gly Asn Ser Thr Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190
```

```
Gly Cys Gly Ile Arg Leu Pro Asn Pro Asp Thr Asp Leu Tyr Trp Phe
            195                 200                 205
Thr Leu Tyr Gln Phe Phe Leu Ala Phe Ala Leu Pro Phe Val Val Ile
        210                 215                 220
Thr Ala Ala Tyr Val Arg Ile Leu Gln Arg Met Thr Ser Ser Val Ala
225                 230                 235                 240
Pro Ala Ser Gln Arg Ser Ile Arg Leu Arg Thr Lys Arg Val Thr Arg
                245                 250                 255
Thr Ala Ile Ala Ile Cys Leu Val Phe Phe Val Cys Trp Ala Pro Tyr
            260                 265                 270
Tyr Val Leu Gln Leu Thr Gln Leu Ser Ile Ser Arg Pro Thr Leu Thr
        275                 280                 285
Phe Val Tyr Leu Tyr Asn Ala Ala Ile Ser Leu Gly Tyr Ala Asn Ser
        290                 295                 300
Cys Leu Asn Pro Phe Val Tyr Ile Val Leu Cys Glu Thr Phe Arg Lys
305                 310                 315                 320
Arg Leu Val Leu Ser Val Lys Pro Ala Ala Gln Gly Gln Leu Arg Ala
                325                 330                 335
Val Ser Asn Ala Gln Thr Ala Asp Glu Glu Arg Thr Glu Ser Lys Gly
            340                 345                 350
Thr
```

<210> SEQ ID NO 7
<211> LENGTH: 24
<212> TYPE: DNA
<213> ORGANISM: Artificial Sequence
<220> FEATURE:
<223> OTHER INFORMATION: 5' macaque MCH1R primer

<400> SEQUENCE: 7
gagcaggcga ccggcactgg ctgg                                    24

<210> SEQ ID NO 8
<211> LENGTH: 28
<212> TYPE: DNA
<213> ORGANISM: Artificial Sequence
<220> FEATURE:
<223> OTHER INFORMATION: 3' macaque MCH1R primer

<400> SEQUENCE: 8
ggaggtgtgc agggtggcag gggaagta                                28

<210> SEQ ID NO 9
<211> LENGTH: 1155
<212> TYPE: DNA
<213> ORGANISM: Homo sapiens

<400> SEQUENCE: 9
atgaattcaa cattattttc ccaggttgaa atcattcag tccactctaa tttctcagag      60
aagaatgccc agcttctggc ttttgaaaat gatgattgtc atctgccctt ggccatgata    120
tttaccttag ctcttgctta tggagctgtg atcattcttg gtgtctctgg aaacctggcc    180
ttgatcataa tcatccttga acaaaaggag atgagaaatg ttaccaacat cctgattgtg    240
aacctttcct tctcagactt gcttgttgcc atcatgtgtc tccccttta atttgtctac     300 acattaatgg accactgggt ctttggtgag gcgatgtgta agttgaatcc ttttgtgcaa    360 tgtgttttcaa tcactgtgtc catttttctct ctggttctca ttgctgtgga acgacatcag    420
```

```
ctgataatca accctcgagg gtggagacca aataatagac atgcttatgt aggtattgct      480
gtgatttggg tccttgctgt ggcttcttct ttgccttttcc tgatctacca agtaatgact     540
gatgagccgt tccaaaatgt aacacttgat gcgtacaaag acaaatacgt gtgctttgat     600
caatttccat cggactctca taggttgtct tataccactc tcctcttggt gctgcagtat     660
tttggtccac tttgttttat atttatttgc tacttcaaga tatatatacg cctaaaaagg     720
agaaacaaca tgatggacaa gatgagagac aataagtaca ggtccagtga aaccaaaaga     780
atcaatatca tgctgctctc cattgtggta gcatttgcag tctgctggct ccctcttacc     840
atctttaaca ctgtgtttga ttggaatcat cagatcattg ctacctgcaa ccacaatctg     900
ttattcctgc tctgccacct cacagcaatg atatccactt gtgtcaaccc catattttat     960
gggttcctga acaaaaactt ccagagagac ttgcagttct tcttcaactt ttgtgatttc     1020
cggtctcggg atgatgatta tgaaacaata gccatgtcca cgatgcacac agatgtttcc     1080
aaaacttctt tgaagcaagc aagcccagtc gcatttaaaa aaatcaacaa caatgatgat     1140
aatgaaaaaa tctga                                                       1155
```

<210> SEQ ID NO 10
<211> LENGTH: 384
<212> TYPE: PRT
<213> ORGANISM: homo sapiens

<400> SEQUENCE: 10

```
Met Asn Ser Thr Leu Phe Ser Gln Val Glu Asn His Ser Val His Ser
1               5                   10                  15

Asn Phe Ser Glu Lys Asn Ala Gln Leu Leu Ala Phe Glu Asn Asp Asp
                20                  25                  30

Cys His Leu Pro Leu Ala Met Ile Phe Thr Leu Ala Leu Ala Tyr Gly
            35                  40                  45

Ala Val Ile Ile Leu Gly Val Ser Gly Asn Leu Ala Leu Ile Ile Ile
        50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
                100                 105                 110

Cys Lys Leu Asn Pro Phe Val Gln Cys Val Ser Ile Thr Val Ser Ile
            115                 120                 125

Phe Ser Leu Val Leu Ile Ala Val Glu Arg His Gln Leu Ile Ile Asn
        130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
                180                 185                 190

Lys Asp Lys Tyr Val Cys Phe Asp Gln Phe Pro Ser Asp Ser His Arg
            195                 200                 205

Leu Ser Tyr Thr Thr Leu Leu Leu Val Leu Gln Tyr Phe Gly Pro Leu
        210                 215                 220

Cys Phe Ile Phe Ile Cys Tyr Phe Lys Ile Tyr Ile Arg Leu Lys Arg
225                 230                 235                 240
```

```
Arg Asn Asn Met Met Asp Lys Met Arg Asp Asn Lys Tyr Arg Ser Ser
                245                 250                 255

Glu Thr Lys Arg Ile Asn Ile Met Leu Leu Ser Ile Val Val Ala Phe
            260                 265                 270

Ala Val Cys Trp Leu Pro Leu Thr Ile Phe Asn Thr Val Phe Asp Trp
        275                 280                 285

Asn His Gln Ile Ile Ala Thr Cys Asn His Asn Leu Leu Phe Leu Leu
    290                 295                 300

Cys His Leu Thr Ala Met Ile Ser Thr Cys Val Asn Pro Ile Phe Tyr
305                 310                 315                 320

Gly Phe Leu Asn Lys Asn Phe Gln Arg Asp Leu Gln Phe Phe Phe Asn
                325                 330                 335

Phe Cys Asp Phe Arg Ser Arg Asp Asp Tyr Glu Thr Ile Ala Met
            340                 345                 350

Ser Thr Met His Thr Asp Val Ser Lys Thr Ser Leu Lys Gln Ala Ser
                355                 360                 365

Pro Val Ala Phe Lys Lys Ile Asn Asn Asn Asp Asp Asn Glu Lys Ile
            370                 375                 380

<210> SEQ ID NO 11
<211> LENGTH: 25
<212> TYPE: DNA
<213> ORGANISM: Artificial Sequence
<220> FEATURE:
<223> OTHER INFORMATION: human NPY1 receptor - BspE forward primer for
      C-terminal

<400> SEQUENCE: 11
aaacttccgg agagacttgc agttc                                          25

<210> SEQ ID NO 12
<211> LENGTH: 32
<212> TYPE: DNA
<213> ORGANISM: Artificial Sequence
<220> FEATURE:
<223> OTHER INFORMATION: human NPY1 receptor - reverse primer for
      C-terminal

<400> SEQUENCE: 12
catccgcggc cgcaggctat aagtagtttc ag                                  32

<210> SEQ ID NO 13
<211> LENGTH: 199
<212> TYPE: DNA
<213> ORGANISM: Homo sapiens

<400> SEQUENCE: 13
tccggagaga cttgcagttc ttcttcaact tttgtgattt ccggtctcgg gatgatgatt     60
atgaaacaat agccatgtcc acgatgcaca cagatgtttc caaaacttct ttgaagcaag   120
caagcccagt cgcatttaaa aaaatcaaca acaatgatga taatgaaaaa atctgaaact   180
acttatagcc tgcggccgc                                                199

<210> SEQ ID NO 14
<211> LENGTH: 82
<212> TYPE: DNA
<213> ORGANISM: Artificial Sequence
<220> FEATURE:
<223> OTHER INFORMATION: IC3 sense oligo

<400> SEQUENCE: 14
```

```
gatcctgata cgcctaaaaa ggagaaacaa catgatggac aagatgagag acaataagta    60
caggtccagt gaaaccaaaa gg                                             82
```

<210> SEQ ID NO 15
<211> LENGTH: 83
<212> TYPE: DNA
<213> ORGANISM: Artificial Sequence
<220> FEATURE:
<223> OTHER INFORMATION: IC3 antisense oligo

<400> SEQUENCE: 15

```
gtcacccttt tggtttcact ggacctgtac ttattgtctc tcatcttgtc catcatgttg    60
tttctccttt ttaggcgtat cag                                            83
```

<210> SEQ ID NO 16
<211> LENGTH: 1062
<212> TYPE: DNA
<213> ORGANISM: Artificial Sequence
<220> FEATURE:
<223> OTHER INFORMATION: human MCH1R plus BspE site added for C-terminal
      chimera

<400> SEQUENCE: 16

```
atggacctgg aagcctcgct gctgcccact ggtcccaatg ccagcaacac ctctgatggc    60
cccgataacc tcacttcggc aggatcacct cctcgcacgg ggagcatctc ctacatcaac   120
atcatcatgc cttcggtgtt cggcaccatc tgcctcctgg gcatcatcgg aactccacg   180 gtcatcttcg cggtcgtgaa gaagtccaag ctgcactggt gcaacaacgt ccccgacatc   240
ttcatcatca acctctcggt agtagatctc ctctttctcc tgggcatgcc cttcatgatc   300
caccagctca tgggcaatgg ggtgtggcac tttggggaga ccatgtgcac cctcatcacg   360
gccatggatg ccaatagtca gttcaccagc acctacatcc tgaccgccat ggccattgac   420
cgctacctgg ccactgtcca ccccatctct tccacgaagt tccggaagcc ctctgtggcc   480
accctggtga tctgcctcct gtgggccctc tccttcatca gcatcacccc tgtgtggctg   540
tatgccagac tcatcccctt ccaggaggt gcagtgggct cgggcatacg cctgcccaac   600
ccagacactg acctctactg gttcacccctg taccagtttt tcctggcctt tgccctgcct   660
tttgtggtca tcagccgc atacgtgagg atcctgcagc gcatgacgtc ctcagtggcc   720
cccgcctccc agcgcagcat ccggctgcgg acaaagaggg tgacccgcac agccatcgcc   780
atctgtctgg tcttctttgt gtgctgggca ccctactatg tgctacagct gacccagttg   840
tccatcagcc gcccgaccct cacctttgtc tacttataca atgcggccat cagcttgggc   900
tatgccaaca gctgcctcaa cccctttgtg tacatcgtgc tctgtgagac gttccggaaa   960
cgcttggtcc tgtcggtgaa gcctgcagcc caggggcagc ttcgcgctgt cagcaacgct  1020
cagacggctg acgaggagag gacagaaagc aaaggcacct ga                    1062
```

<210> SEQ ID NO 17
<211> LENGTH: 1074
<212> TYPE: DNA
<213> ORGANISM: Artificial Sequence
<220> FEATURE:
<223> OTHER INFORMATION: human MCH1R/NPY1 IC3 chimera

<400> SEQUENCE: 17

```
atggacctgg aagcctcgct gctgcccact ggtcccaatg ccagcaacac ctctgatggc    60
cccgataacc tcacttcggc aggatcacct cctcgcacgg ggagcatctc ctacatcaac   120
```

-continued

```
atcatcatgc cttcggtgtt cggcaccatc tgcctcctgg gcatcatcgg gaactccacg      180
gtcatcttcg cggtcgtgaa gaagtccaag ctgcactggt gcaacaacgt ccccgacatc      240
ttcatcatca acctctcggt agtagatctc ctctttctcc tgggcatgcc cttcatgatc      300
caccagctca tgggcaatgg ggtgtggcac tttggggaga ccatgtgcac cctcatcacg      360
gccatggatg ccaatagtca gttcaccagc acctacatcc tgaccgccat ggccattgac      420
cgctacctgg ccactgtcca ccccatctct tccacgaagt tccggaagcc ctctgtggcc      480
accctggtga tctgcctcct gtgggccctc tccttcatca gcatcacccc tgtgtggctg      540
tatgccagac tcatcccctt cccaggaggt gcagtgggct cgggcatacg cctgcccaac      600
ccagacactg acctctactg gttcacccctg taccagtttt tcctggcctt tgccctgcct      660
tttgtggtca tcacagccgc atacgtgagg atcctgatac gcctaaaaag agaaacaac       720
atgatggaca agatgagaga caataagtac aggtccagtg aaaccaaaag ggtgacccgc      780
acagccatcg ccatctgtct ggtcttcttt gtgtgctggg caccctacta tgtgctacag      840
ctgacccagt tgtccatcag ccgcccgacc ctcaccttttg tctacttata caatgcggcc      900
atcagcttgg gctatgccaa cagctgcctc aaccccttttg tgtacatcgt gctctgtgag      960
acgttccgca aacgcttggt cctgtcggtg aagcctgcag cccagggggca gcttcgcgct     1020
gtcagcaacg ctcagacggc tgacgaggag aggacagaaa gcaaaggcac ctga           1074
```

<210> SEQ ID NO 18
<211> LENGTH: 357
<212> TYPE: PRT
<213> ORGANISM: Artificial Sequence
<220> FEATURE:
<223> OTHER INFORMATION: human MCH1R/NPY1 IC3 chimera

<400> SEQUENCE: 18

```
Met Asp Leu Glu Ala Ser Leu Leu Pro Thr Gly Pro Asn Ala Ser Asn
  1               5                  10                  15

Thr Ser Asp Gly Pro Asp Asn Leu Thr Ser Ala Gly Ser Pro Pro Arg
             20                  25                  30

Thr Gly Ser Ile Ser Tyr Ile Asn Ile Ile Met Pro Ser Val Phe Gly
         35                  40                  45

Thr Ile Cys Leu Leu Gly Ile Ile Gly Asn Ser Thr Val Ile Phe Ala
     50                  55                  60

Val Val Lys Lys Ser Lys Leu His Trp Cys Asn Asn Val Pro Asp Ile
 65                  70                  75                  80

Phe Ile Ile Asn Leu Ser Val Val Asp Leu Leu Phe Leu Leu Gly Met
                 85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
```

-continued

```
                195                 200                 205
Thr Leu Tyr Gln Phe Phe Leu Ala Phe Ala Leu Pro Phe Val Val Ile
        210                 215                 220
Thr Ala Ala Tyr Val Arg Ile Leu Ile Arg Leu Lys Arg Arg Asn Asn
225                 230                 235                 240
Met Met Asp Lys Met Arg Asp Asn Lys Tyr Arg Ser Ser Glu Thr Lys
                245                 250                 255
Arg Val Thr Arg Thr Ala Ile Ala Ile Cys Leu Val Phe Phe Val Cys
            260                 265                 270
Trp Ala Pro Tyr Tyr Val Leu Gln Leu Thr Gln Leu Ser Ile Ser Arg
            275                 280                 285
Pro Thr Leu Thr Phe Val Tyr Leu Tyr Asn Ala Ala Ile Ser Leu Gly
            290                 295                 300
Tyr Ala Asn Ser Cys Leu Asn Pro Phe Val Tyr Ile Val Leu Cys Glu
305                 310                 315                 320
Thr Phe Arg Lys Arg Leu Val Leu Ser Val Lys Pro Ala Ala Gln Gly
                325                 330                 335
Gln Leu Arg Ala Val Ser Asn Ala Gln Thr Ala Asp Glu Glu Arg Thr
            340                 345                 350
Glu Ser Lys Gly Thr
        355

<210> SEQ ID NO 19
<211> LENGTH: 1128
<212> TYPE: DNA
<213> ORGANISM: Artificial Sequence
<220> FEATURE:
<223> OTHER INFORMATION: human MCH1R/human NPY1 C-terminal chimera

<400> SEQUENCE: 19
atggacctgg aagcctcgct gctgcccact ggtcccaatg ccagcaacac ctctgatggc      60
cccgataacc tcacttcggc aggatcacct cctcgcacgg ggagcatctc ctacatcaac     120
atcatcatgc cttcggtgtt cggcaccatc tgcctcctgg catcatcgg gaactccacg      180
gtcatcttcg cggtcgtgaa gagtccaag ctgcactggt gcaacaacgt ccccgacatc      240
ttcatcatca cctctcggt agtagatctc ctctttctcc tgggcatgcc cttcatgatc      300
caccagctca tgggcaatgg ggtgtggcac tttgggggaga ccatgtgcac cctcatcacg      360
gccatggatg ccaatagtca gttcaccagc acctacatcc tgaccgccat ggccattgac      420
cgctacctgg ccactgtcca ccccatctct tccacgaagt tccggaagcc ctctgtggcc      480
accctggtga tctgcctcct gtgggccctc tccttcatca gcatcacccc tgtgtggctg      540
tatgccagac tcatcccctt cccaggaggt gcagtgggct cggcatacg cctgcccaac      600
ccagacactg acctctactg gttcaccctg taccagtttt tcctggcctt tgccctgcct      660
tttgtggtca tcagccgc atacgtgagg atcctgcagc gcatgacgtc ctcagtggcc      720
cccgcctccc agcgcagcat ccggctgcgg acaaagaggg tgacccgcac agccatcgcc      780
atctgtctgg tcttctttgt gtgctgggca ccctactatg tgctacagct gacccagttg      840
tccatcagcc gcccgaccct cacctttgtc tacttataca atgcggccat cagcttgggc      900
tatgccaaca gctgcctcaa cccctttgtg tacatcgtgc tctgtgagac gttccggaga      960
gacttgcagt tcttcttcaa cttttgtgat tccggtctc gggatgatga ttatgaaaca     1020
atagccatgt ccacgatgca cacagatgtt tccaaaactt cttgaagca agcaagccca     1080
gtcgcattta aaaaaatcaa caacaatgat gataatgaaa aaatctga                1128
```

-continued

<210> SEQ ID NO 20
<211> LENGTH: 375
<212> TYPE: PRT
<213> ORGANISM: Artificial Sequence
<220> FEATURE:
<223> OTHER INFORMATION: human MCH1R/human NPY1 C-terminal chimera
    protein sequence

<400> SEQUENCE: 20

```
Met Asp Leu Glu Ala Ser Leu Leu Pro Thr Gly Pro Asn Ala Ser Asn
1               5                   10                  15

Thr Ser Asp Gly Pro Asp Asn Leu Thr Ser Ala Gly Ser Pro Pro Arg
            20                  25                  30

Thr Gly Ser Ile Ser Tyr Ile Asn Ile Ile Met Pro Ser Val Phe Gly
        35                  40                  45

Thr Ile Cys Leu Leu Gly Ile Ile Gly Asn Ser Thr Val Ile Phe Ala
    50                  55                  60

Val Val Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Arg
305                 310                 315                 320

Asp Leu Gln Phe Phe Asn Phe Cys Asp Phe Arg Ser Arg Asp Asp
                325                 330                 335

Asp Tyr Glu Thr Ile Ala Met Ser Thr Met His Thr Asp Val Ser Lys
            340                 345                 350

Thr Ser Leu Lys Gln Ala Ser Pro Val Ala Phe Lys Lys Ile Asn Asn
```

355                 360                 365
Asn Asp Asp Asn Glu Lys Ile
    370             375

<210> SEQ ID NO 21
<211> LENGTH: 6498
<212> TYPE: DNA
<213> ORGANISM: Artificial Sequence
<220> FEATURE:
<223> OTHER INFORMATION: human MCH1R/human NPY1 IC3 chimera in
      pcDNA3.1Plus (pN105)

<400> SEQUENCE: 21

| | | | | | |
|---|---|---|---|---|---|
| gacggatcgg | gagatctccc | gatcccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacgggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagcttggta | ccgagctcgg | atccgccccc | accatggacc | tggaagcctc | 960 |
| gctgctgccc | actggtccca | atgccagcaa | cacctctgat | ggccccgata | acctcacttc | 1020 |
| ggcaggatca | cctcctcgca | cggggagcat | ctcctacatc | aacatcatca | tgccttcgt | 1080 |
| gttcggcacc | atctgcctcc | tgggcatcat | cgggaactcc | acggtcatct | cgcggtcgt | 1140 |
| gaagaagtcc | aagctgcact | ggtgcaacaa | cgtccccgac | atcttcatca | tcaacctctc | 1200 |
| ggtagtagat | ctcctctttc | tcctgggcat | gcccttcatg | atccaccagc | tcatgggcaa | 1260 |
| tgggggtgtgg | cactttgggg | agaccatgtg | caccctcatc | acggccatgg | atgccaatag | 1320 |
| tcagttcacc | agcacctaca | tcctgaccgc | catggccatt | gaccgctacc | tggccactgt | 1380 |
| ccacccatc | tcttccacga | agttccggaa | gccctctgtg | gccacccactgg | tgatctgcct | 1440 |
| cctgtgggcc | ctctccttca | tcagcatcac | ccctgtgtgg | ctgtatgcca | gactcatccc | 1500 |
| cttcccagga | ggtgcagtgg | gctgcggcat | acgcctgccc | aacccagaca | ctgacctcta | 1560 |
| ctggttcacc | ctgtaccagt | ttttcctggc | ctttgccctg | cctttgtgg | tcatcacagc | 1620 |
| cgcatacgtg | aggatcctga | tacgcctaaa | aaggagaaac | aacatgatgg | acaagatgag | 1680 |
| agacaataag | tacaggtcca | gtgaaaccaa | aagggtgacc | cgcacagcca | tcgccatctg | 1740 |
| tctggtcttc | tttgtgtgct | gggcacccta | ctatgtgcta | cagctgaccc | agttgtccat | 1800 |
| cagccgcccg | accctcacct | ttgtctactt | atacaatgcg | gccatcagct | ggggctatgc | 1860 |
| caacagctgc | ctcaacccct | tgtgtacat | cgtgctctgt | gagacgttcc | gcaaacgctt | 1920 |

-continued

```
ggtcctgtcg gtgaagcctg cagcccaggg gcagcttcgc gctgtcagca acgctcagac    1980
ggctgacgag gagaggacag aaagcaaagg cacctgatac ttcccctgcc accctgggct    2040
agagcggccg ctcgagtcta gagggcccgt ttaaacccgc tgatcagcct cgactgtgcc    2100
ttctagttgc cagccatctg ttgtttgccc ctcccccgtg ccttccttga ccctggaagg    2160
tgccactccc actgtccttt cctaataaaa tgaggaaatt gcatcgcatt gtctgagtag    2220
gtgtcattct attctggggg gtggggtggg gcaggacagc aaggggagg attgggaaga     2280
caatagcagg catgctgggg atgcgtgggg ctctatggct tctgaggcgg aaagaaccag    2340
ctgggctct aggggtatc cccacgcgcc ctgtagcggc gcattaagcg cggcgggtgt      2400
ggtggttacg cgcagcgtga ccgctacact tgccagcgcc ctagcgcccg ctcctttcgc    2460
tttcttccct tcctttctcg ccacgttcgc cggctttccc cgtcaagctc taaatcgggg    2520
catccctta gggttccgat ttagtgcttt acggcacctc gaccccaaaa aacttgatta     2580
gggtgatggt tcacgtagtg ggccatcgcc ctgatagacg ttttttcgcc ctttgacgtt    2640
ggagtccacg ttctttaata gtggactctt gttccaaact ggaacaacac tcaaccctat    2700
ctcggtctat tcttttgatt tataagggat tttggggatt tcggcctatt ggttaaaaaa    2760
tgagctgatt taacaaaaat ttaacgcgaa ttaattctgt ggaatgtgtg tcagttaggg    2820
tgtggaaagt ccccaggctc cccaggcagg cagaagtatg caaagcatgc atctcaatta    2880
gtcagcaacc aggtgtggaa agtccccagg ctccccagca ggcagaagta tgcaaagcat    2940
gcatctcaat tagtcagcaa ccatagtccc gcccctaact ccgcccatcc cgcccctaac    3000
tccgcccagt tccgcccatt ctccgcccca tggctgacta attttttttta tttatgcaga    3060
ggccgaggcc gcctctgcct ctgagctatt ccagaagtag tgaggaggct ttttttggagg    3120
cctaggcttt tgcaaaaagc tcccgggagc ttgtatatcc attttcggat ctgatcaaga    3180
gacaggatga ggatcgtttc gcatgattga acaagatgga ttgcacgcag gttctccggc    3240
cgcttgggtg gagaggctat tcggctatga ctgggcacaa cagacaatcg gctgctctga    3300
tgccgccgtg ttccggctgt cagcgcaggg gcgcccggtt ctttttgtca agaccgacct    3360
gtccggtgcc ctgaatgaac tgcaggacga ggcagcgcgg ctatcgtggc tggccacgac    3420
gggcgttcct tgcgcagctg tgctcgacgt tgtcactgaa gcgggaaggg actggctgct    3480
attgggcgaa gtgccggggc aggatctcct gtcatctcac cttgctcctg ccgagaaagt    3540
atccatcatg gctgatgcaa tgcggcggct gcatacgctt gatccggcta cctgcccatt    3600
cgaccaccaa gcgaaacatc gcatcgagcg agcacgtact cggatggaag ccggtcttgt    3660
cgatcaggat gatctggacg aagagcatca ggggctcgcg ccagccgaac tgttcgccag    3720
gctcaaggcg cgcatgcccg acggcgagga tctcgtcgtg acccatggcg atgcctgctt    3780
gccgaatatc atggtggaaa atggccgctt ttctggattc atcgactgtg gccggctggg    3840
tgtggcggac cgctatcagg acatagcgtt ggctacccgt gatattgctg aagagcttgg    3900
cggcgaatgg gctgaccgct tcctcgtgct ttacggtatc gccgctcccg attcgcagcg    3960
catcgccttc tatcgccttc ttgacgagtt cttctgagcg ggactctggg gttcgaaatg    4020
accgaccaag cgacgcccaa cctgccatca cgagatttcg attccaccgc cgccttctat    4080
gaaaggttgg gcttcggaat cgttttccgg gacgccggct ggatgatcct ccagcgcggg    4140
gatctcatgc tggagttctt cgcccacccc aacttgttta ttgcagctta taatggttac    4200
aaataaagca atagcatcac aaatttcaca aataaagcat ttttttcact gcattctagt    4260
```

-continued

```
tgtggtttgt ccaaactcat caatgtatct tatcatgtct gtataccgtc gacctctagc      4320
tagagcttgg cgtaatcatg gtcatagctg tttcctgtgt gaaattgtta tccgctcaca      4380
attccacaca acatacgagc cggaagcata aagtgtaaag cctggggtgc ctaatgagtg      4440
agctaactca cattaattgc gttgcgctca ctgcccgctt tccagtcggg aaacctgtcg      4500
tgccagctgc attaatgaat cggccaacgc gcggggagag gcggtttgcg tattgggcgc      4560
tcttccgctt cctcgctcac tgactcgctg cgctcggtcg ttcggctgcg gcgagcggta      4620
tcagctcact caaaggcggt aatacggtta tccacagaat cagggataa cgcaggaaag      4680 aacatgtgag caaaaggcca gcaaaaggcc aggaaccgta aaaaggccgc gttgctggcg      4740 ttttccata ggctccgccc ccctgacgag catcacaaaa atcgacgctc aagtcagagg      4800
tggcgaaacc cgacaggact ataaagatac caggcgtttc ccctggaag ctccctcgtg      4860 cgctctcctg ttccgaccct gccgcttacc ggatacctgt ccgcctttct cccttcggga      4920
agcgtggcgc tttctcaatg ctcacgctgt aggtatctca gttcggtgta ggtcgttcgc      4980
tccaagctgg gctgtgtgca cgaaccccc gttcagcccg accgctgcgc cttatccggt      5040
aactatcgtc ttgagtccaa cccggtaaga cacgacttat cgccactggc agcagccact      5100
ggtaacagga ttagcagagc gaggtatgta ggcggtgcta cagagttctt gaagtggtgg      5160
cctaactacg gctacactag aaggacagta tttggtatct gcgctctgct gaagccagtt      5220
accttcggaa aaagagttgg tagctcttga tccggcaaac aaaccaccgc tggtagcggt      5280 ggttttttg tttgcaagca gcagattacg cgcagaaaaa aaggatctca agaagatcct      5340
ttgatctttt ctacggggtc tgacgctcag tggaacgaaa actcacgtta agggattttg      5400
gtcatgagat tatcaaaaag gatcttcacc tagatccttt taaattaaaa atgaagtttt      5460
aaatcaatct aaagtatata tgagtaaact tggtctgaca gttaccaatg cttaatcagt      5520
gaggcaccta tctcagcgat ctgtctattt cgttcatcca tagttgcctg actccccgtc      5580
gtgtagataa ctacgatacg ggagggctta ccatctggcc ccagtgctgc aatgataccg      5640
cgagacccac gctcaccggc tccagattta tcagcaataa accagccagc cggaagggcc      5700
gagcgcagaa gtggtcctgc aactttatcc gcctccatcc agtctattaa ttgttgccgg      5760
gaagctagag taagtagttc gccagttaat agtttgcgca acgttgttgc cattgctaca      5820
ggcatcgtgg tgtcacgctc gtcgtttggt atggcttcat tcagctccgg ttcccaacga      5880
tcaaggcgag ttacatgatc ccccatgttg tgcaaaaaag cggttagctc cttcggtcct      5940
ccgatcgttg tcagaagtaa gttggccgca gtgttatcac tcatggttat ggcagcactg      6000
cataattctc ttactgtcat gccatccgta agatgctttt ctgtgactgg tgagtactca      6060
accaagtcat tctgagaata gtgtatgcgg cgaccgagtt gctcttgccc ggcgtcaata      6120
cgggataata ccgcgccaca tagcagaact ttaaaagtgc tcatcattgg aaaacgttct      6180
tcggggcgaa aactctcaag gatcttaccg ctgttgagat ccagttcgat gtaacccact      6240
cgtgcaccca actgatcttc agcatctttt actttcacca gcgtttctgg gtgagcaaaa      6300
acaggaaggc aaaatgccgc aaaaaaggga ataagggcga cacggaaatg ttgaatactc      6360
atactcttcc ttttcaata ttattgaagc atttatcagg gttattgtct catgagcgga      6420
tacatatttg aatgtattta gaaaaataaa caaataggg ttccgcgcac atttccccga      6480
aaagtgccac ctgacgtc                                                   6498
```

<210> SEQ ID NO 22
<211> LENGTH: 6582

<212> TYPE: DNA
<213> ORGANISM: Artificial Sequence
<220> FEATURE:
<223> OTHER INFORMATION: human MCH1R/human NPY1 C-terminal chimera in
      pcDNA3.1Plus (pN107)

<400> SEQUENCE: 22

| | | | | | |
|---|---|---|---|---|---|
| gacggatcgg | gagatctccc | gatccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacgggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagcttggta | ccgagctcgg | atccactagt | ccagtgtggt | ggaattcctg | 960 |
| cagcccgggg | gatccgcccc | caccatggac | ctggaagcct | cgctgctgcc | cactggtccc | 1020 |
| aatgccagca | acacctctga | tggccccgat | aacctcactt | cggcaggatc | acctcctcgc | 1080 |
| acggggagca | tctcctacat | caacatcatc | atgccttcgg | tgttcggcac | catctgcctc | 1140 |
| ctgggcatca | tcgggaactc | cacggtcatc | ttcgcggtcg | tgaagaagtc | caagctgcac | 1200 |
| tggtgcaaca | acgtccccga | catcttcatc | atcaacctct | cggtagtaga | tctcctcttt | 1260 |
| ctcctgggca | tgcccttcat | gatccaccag | ctcatgggca | atgggggtgtg | gcactttggg | 1320 |
| gagaccatgt | gcaccctcat | cacggccatg | gatgccaata | gtcagttcac | cagcacctac | 1380 |
| atcctgaccg | ccatggccat | tgaccgctac | ctggccactg | tccacccat | ctcttccacg | 1440 |
| aagttccgga | agccctctgt | ggccaccctg | gtgatctgcc | tcctgtgggc | cctctccttc | 1500 |
| atcagcatca | cccctgtgtg | gctgtatgcc | agactcatcc | ccttcccagg | aggtgcagtg | 1560 |
| ggctgcggca | tacgcctgcc | caacccagac | actgacctct | actggttcac | cctgtaccag | 1620 |
| tttttcctgg | cctttgccct | gccttttgtg | gtcatcacag | ccgcatacgt | gaggatcctg | 1680 |
| cagcgcatga | cgtcctcagt | ggcccccgcc | tcccagcgca | gcatccggct | gcggacaaag | 1740 |
| agggtgaccc | gcacagccat | cgccatctgt | ctggtcttct | tgtgtgctg | gcaccctac | 1800 |
| tatgtgctac | agctgaccca | gttgtccatc | agccgcccga | ccctcacctt | tgtctactta | 1860 |
| tacaatgcgg | ccatcagctt | gggctatgcc | aacagctgcc | tcaacccctt | tgtgtacatc | 1920 |
| gtgctctgtg | agacgttccg | gagagacttg | cagttcttct | tcaactttg | tgatttccgg | 1980 |
| tctcggggatg | atgattatga | aacaatagcc | atgtccacga | tgcacacaga | tgtttccaaa | 2040 |
| acttctttga | agcaagcaag | cccagtcgca | tttaaaaaaa | tcaacaacaa | tgatgataat | 2100 |
| gaaaaaatct | gaaactactt | atagcctgcg | gccgctcgag | tctagagggc | ccgtttaaac | 2160 |

-continued

```
ccgctgatca gcctcgactg tgccttctag ttgccagcca tctgttgttt gcccctcccc   2220
cgtgccttcc ttgaccctgg aaggtgccac tcccactgtc ctttcctaat aaaatgagga   2280
aattgcatcg cattgtctga gtaggtgtca ttctattctg gggggtgggg tggggcagga   2340
cagcaagggg gaggattggg aagacaatag caggcatgct ggggatgcgg tgggctctat   2400
ggcttctgag gcgaaagaa ccagctgggg ctctagggg tatccccacg cgccctgtag   2460
cggcgcatta agcgcggcgg gtgtggtggt tacgcgcagc gtgaccgcta cacttgccag   2520
cgccctagcg cccgctcctt tcgctttctt ccttcctt ctcgccacgt tcgccggctt   2580
tccccgtcaa gctctaaatc gggcatccc tttagggttc cgatttagtg ctttacggca   2640
cctcgacccc aaaaaacttg attagggtga tggttcacgt agtgggccat cgccctgata   2700
gacggttttt cgccctttga cgttggagtc cacgttcttt aatagtggac tcttgttcca   2760
aactggaaca acactcaacc ctatctcggt ctattctttt gatttataag ggattttggg   2820
gatttcggcc tattggttaa aaaatgagct gatttaacaa aaatttaacg cgaattaatt   2880
ctgtggaatg tgtgtcagtt agggtgtgga agtccccag gctccccagg caggcagaag   2940
tatgcaaagc atgcatctca attagtcagc aaccaggtgt ggaaagtccc caggctcccc   3000
agcaggcaga gtatgcaaa gcatgcatct caattagtca gcaaccatag tcccgcccct   3060
aactccgccc atcccgcccc taactccgcc cagttccgcc cattctccgc ccatggctg    3120
actaattttt tttatttatg cagaggccga ggccgcctct gcctctgagc tattccagaa   3180
gtagtgagga ggcttttttg gaggcctagg cttttgcaaa aagctcccgg gagcttgtat   3240
atccattttc ggatctgatc aagagacagg atgaggatcg tttcgcatga ttgaacaaga   3300
tggattgcac gcaggttctc cggccgcttg ggtggagagg ctattcggct atgactgggc   3360
acaacagaca atcggctgct ctgatgccgc cgtgttccgg ctgtcagcgc agggggcgccc   3420
ggttctttt gtcaagaccg acctgtccgg tgccctgaat gaactgcagg acgaggcagc   3480
gcggctatcg tggctggcca cgacgggcgt tccttgcgca gctgtgctcg acgttgtcac   3540
tgaagcggga agggactggc tgctattggg cgaagtgccg gggcaggatc tcctgtcatc   3600
tcaccttgct cctgccgaga agtatccat catggctgat gcaatgcggc ggctgcatac   3660
gcttgatccg gctacctgcc cattcgacca ccaagcgaaa catcgcatcg agcgagcacg   3720
tactcggatg gaagccggtc ttgtcgatca ggatgatctg gacgaagagc atcaggggct   3780
cgcgccagcc gaactgttcg ccaggctcaa ggcgcgcatg cccgacggcg aggatctcgt   3840
cgtgacccat ggcgatgcct gcttgccgaa tatcatggtg gaaaatggcc gcttttctgg   3900
attcatcgac tgtggccggc tgggtgtggc ggaccgctat caggacatag cgttggctac   3960
ccgtgatatt gctgaagagc ttggcggcga atgggctgac cgcttcctcg tgctttacgg   4020
tatcgccgct cccgattcgc agcgcatcgc cttctatcgc cttcttgacg agttcttctg   4080
agcgggactc tggggttcga aatgaccgac caagcgacgc ccaacctgcc atcacgagat   4140
ttcgattcca ccgccgcctt ctatgaaagg ttgggcttcg aatcgttttt ccggacgcc    4200
ggctggatga tcctccagcg cggggatctc atgctggagt tcttcgccca ccccaacttg   4260
tttattgcag cttataatgg ttacaaataa agcaatagca tcacaaattt cacaaataaa   4320
gcatttttt cactgcattc tagttgtggt ttgtccaaac tcatcaatgt atcttatcat   4380
gtctgtatac cgtcgacctc tagctagagc ttggcgtaat catggtcata gctgtttcct   4440
gtgtgaaatt gttatccgct cacaattcca cacaacatac gagccggaag cataaagtgt   4500
```

```
aaagcctggg gtgcctaatg agtgagctaa ctcacattaa ttgcgttgcg ctcactgccc    4560
gctttccagt cgggaaacct gtcgtgccag ctgcattaat gaatcggcca acgcgcgggg    4620
agaggcggtt tgcgtattgg cgctcttcc gcttcctcgc tcactgactc gctgcgctcg     4680
gtcgttcggc tgcggcgagc ggtatcagct cactcaaagg cggtaatacg gttatccaca    4740
gaatcagggg ataacgcagg aaagaacatg tgagcaaaag gccagcaaaa ggccaggaac    4800
cgtaaaaagg ccgcgttgct ggcgtttttc cataggctcc gcccccctga cgagcatcac    4860
aaaaatcgac gctcaagtca gaggtggcga acccgacag gactataaag ataccaggcg     4920
tttccccctg aagctccct cgtgcgctct cctgttccga ccctgccgct taccggatac     4980
ctgtccgcct ttctcccttc gggaagcgtg gcgctttctc aatgctcacg ctgtaggtat    5040
ctcagttcgg tgtaggtcgt tcgctccaag ctgggctgtg tgcacgaacc cccgttcag    5100 cccgaccgct gcgccttatc cggtaactat cgtcttgagt ccaacccggt aagacacgac    5160
ttatcgccac tggcagcagc cactggtaac aggattagca gagcgaggta tgtaggcggt    5220
gctacagagt tcttgaagtg gtggcctaac tacggctaca ctagaaggac agtatttggt    5280
atctgcgctc tgctgaagcc agttaccttc ggaaaaagag ttggtagctc ttgatccggc    5340
aaacaaacca ccgctggtag cggtggtttt tttgtttgca agcagcagat tacgcgcaga    5400
aaaaaaggat ctcaagaaga tcctttgatc ttttctacgg ggtctgacgc tcagtggaac    5460
gaaaactcac gttaagggat tttggtcatg agattatcaa aaaggatctt cacctagatc    5520 ctttaaatt aaaaatgaag ttttaaatca atctaaagta tatatgagta aacttggtct    5580
gacagttacc aatgcttaat cagtgaggca cctatctcag cgatctgtct atttcgttca    5640
tccatagttg cctgactccc cgtcgtgtag ataactacga tacgggaggg cttaccatct    5700
ggccccagtg ctgcaatgat accgcgagac ccacgctcac cggctccaga tttatcagca    5760
ataaaccagc cagccggaag ggccgagcgc agaagtggtc ctgcaacttt atccgcctcc    5820
atccagtcta ttaattgttg ccgggaagct agagtaagta gttcgccagt taatagtttg    5880
cgcaacgttg ttgccattgc tacaggcatc gtggtgtcac gctcgtcgtt tggtatggct    5940
tcattcagct ccggttccca acgatcaagg cgagttacat gatcccccat gttgtgcaaa    6000
aaagcggtta gctccttcgg tcctccgatc gttgtcagaa gtaagttggc cgcagtgtta    6060
tcactcatgg ttatggcagc actgcataat tctcttactg tcatgccatc cgtaagatgc    6120
ttttctgtga ctggtgagta ctcaaccaag tcattctgag aatagtgtat gcggcgaccg    6180
agttgctctt gcccggcgtc aatacgggat aataccgcgc cacatagcag aactttaaaa    6240
gtgctcatca ttggaaaacg ttcttcgggg cgaaaactct caaggatctt accgctgttg    6300
agatccagtt cgatgtaacc cactcgtgca cccaactgat cttcagcatc ttttactttc    6360
accagcgttt ctgggtgagc aaaaacagga aggcaaaatg ccgcaaaaaa gggaataagg    6420
gcgacacgga aatgttgaat actcatactc ttcctttttc aatattattg aagcatttat    6480
cagggttatt gtctcatgag cggatacata tttgaatgta tttagaaaaa taaacaaata    6540
ggggttccgc gcacatttcc ccgaaaagtg ccacctgacg tc                       6582
```

<210> SEQ ID NO 23
<211> LENGTH: 2305
<212> TYPE: DNA
<213> ORGANISM: Homo sapiens

<400> SEQUENCE: 23

```
gaattcatgc cgcgtttctg tgttggacag gggtgacttt gtgccggatg gcttctgtgt    60
```

-continued

```
gagagcgcgc gcgagtgtgc atgtcggtga gctgggaggg tgtgtctcag tgtctatggc    120
tgtggttcgg tataagtcta agcatgtctg ccagggtgta tttgtgcctg tatgtgcgtg    180
cctcggtggg cactctcgtt tccttccgaa tgtggggcag tgccggtgtg ctgccctctg    240
ccttgagacc tcaagccgcg caggcgccca gggcaggcag gtagcggcca cagaagagcc    300
aaaagctccc gggttggctg gtaagcacac cacctccagc tttagccctc tggggccagc    360
cagggtagcc gggaagcagt ggtggcccgc cctccaggga gcagttgggc cccgcccggg    420
ccagcctcag gagaaggagg gcgaggggag gggagggaaa ggggaggagt gcctcgcccc    480
ttcgcggctg ccggcgtgcc attggccgaa agttcccgta cgtcacggcg agggcagttc    540
ccctaaagtc ctgtgcacat aacgggcaga acgcactgcg aagcggcttc ttcagagcac    600
gggctggaac tggcaggcac cgcgagcccc tagcacccga caagctgagt gtgcaggacg    660
agtccccacc acaccacac cacagccgct gaatgaggct tccaggcgtc cgctcgcggc    720
ccgcagagcc ccgccgtggg tccgcctgct gaggcgcccc cagccagtgc gcttacctgc    780
cagactgcgc gccatggggc aacccgggaa cggcagcgcc ttcttgctgg cacccaatag    840
aagccatgcg ccggaccacg acgtcacgca gcaaagggac gaggtgtggg tggtgggcat    900
gggcatcgtc atgtctctca tcgtcctggc catcgtgttt ggcaatgtgc tggtcatcac    960
agccattgcc aagttcgagc gtctgcagac ggtcaccaac tacttcatca cttcactggc   1020
ctgtgctgat ctggtcatgg gcctggcagt ggtgccctt ggggccgccc atattcttat   1080
gaaaatgtgg acttttggca acttctggtg cgagttttgg acttccattg atgtgctgtg   1140
cgtcacggcc agcattgaga ccctgtgcgt gatcgcagtg gatcgctact ttgccattac   1200
ttcacctttc aagtaccaga gcctgctgac caagaataag gcccgggtga tcattctgat   1260
ggtgtggatt gtgtcaggcc ttacctcctt cttgcccatt cagatgcact ggtaccgggc   1320
cacccaccag gaagccatca actgctatgc caatgagacc tgctgtgact cttcacgaa    1380
ccaagcctat gccattgcct cttccatcgt gtccttctac gttcccctgg tgatcatggt   1440
cttcgtctac tccagggtct ttcaggaggc caaaaggcag ctccagaaga ttgacaaatc   1500
tgagggccgc ttccatgtcc agaaccttag ccaggtggag caggatgggc ggacggggca   1560
tggactccga agatcttcca agttctgctt gaaggagcac aaaagccctca agacgttagg   1620
catcatcatg ggcacttca ccctctgctg gctgcccttc ttcatcgtta cattgtgca    1680
tgtgatccag gataacctca tccgtaagga agtttacatc ctcctaaatt ggataggcta   1740
tgtcaattct ggtttcaatc cccttatcta ctgccggagc ccagatttca ggattgcctt   1800
ccaggagctt ctgtgcctgc gcaggtcttc tttgaaggcc tatgggaatg ctactccag    1860
caacggcaac acagggagc agagtggata tcacgtggaa caggagaaag aaaataaact   1920
gctgtgtgaa gacctcccag gcacggaaga ctttgtgggc catcaaggta ctgtgcctag   1980
cgataacatt gattcacaag ggaggaattg tagtacaaat gactcactgc tgtaaagcag   2040
ttttctact tttaaagacc ccccccccca acagaacact aaacagacta tttaacttga   2100
gggtaataaa cttagaataa aattgtaaaa ttgtatagag atatgcagaa ggaagggcat   2160
ccttctgcct ttttatttt tttaagctgt aaaaagagag aaaacttatt tgagtgatta   2220
tttgttattt gtacagttca gttcctcttt gcatggaatt tgtaagttta tgtctaaaga   2280
gctttagtcc tagaggacct gagtc                                        2305
```

<210> SEQ ID NO 24

<211> LENGTH: 413
<212> TYPE: PRT
<213> ORGANISM: homo sapiens

<400> SEQUENCE: 24

```
Met Gly Gln Pro Gly Asn Gly Ser Ala Phe Leu Leu Ala Pro Asn Arg
 1               5                  10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
        355                 360                 365

Glu Gln Glu Lys Glu Asn Lys Leu Leu Cys Glu Asp Leu Pro Gly Thr
    370                 375                 380

Glu Asp Phe Val Gly His Gln Gly Thr Val Pro Ser Asp Asn Ile Asp
```

385                 390                 395                 400
Ser Gln Gly Arg Asn Cys Ser Thr Asn Asp Ser Leu Leu
                    405                 410

<210> SEQ ID NO 25
<211> LENGTH: 29
<212> TYPE: DNA
<213> ORGANISM: Artificial Sequence
<220> FEATURE:
<223> OTHER INFORMATION: human beta-2 adrenergic receptor forward primer

<400> SEQUENCE: 25
tgttccggag ttctttgaag gcctatggg                                       29

<210> SEQ ID NO 26
<211> LENGTH: 25
<212> TYPE: DNA
<213> ORGANISM: Artificial Sequence
<220> FEATURE:
<223> OTHER INFORMATION: human beta-2 adrenergic receptor reverse primer

<400> SEQUENCE: 26
gctctagagc ttacagcagt gagtc                                           25

<210> SEQ ID NO 27
<211> LENGTH: 1167
<212> TYPE: DNA
<213> ORGANISM: Artificial Sequence
<220> FEATURE:
<223> OTHER INFORMATION: human MCH1R/human beta-2 adrenergic receptor
      C-terminal chimera

<400> SEQUENCE: 27
atggacctgg aagcctcgct gctgcccact ggtcccaatg ccagcaacac ctctgatggc      60
cccgataacc tcacttcggc aggatcacct cctcgcacgg ggagcatctc ctacatcaac     120
atcatcatgc cttcggtgtt cggcaccatc tgcctcctgg gcatcatcgg gaactccacg     180
gtcatcttcg cggtcgtgaa gaagtccaag ctgcactggt gcaacaacgt ccccgacatc     240
ttcatcatca acctctcggt agtagatctc ctctttctcc tgggcatgcc cttcatgatc     300
caccagctca tgggcaatgg ggtgtggcac tttggggaga ccatgtgcac cctcatcacg     360
gccatggatg ccaatagtca gttcaccagc acctacatcc tgaccgccat ggccattgac     420
cgctacctgg ccactgtcca ccccatctct ccacgaagt tccggaagcc ctctgtggcc      480
accctggtga tctgcctcct gtgggccctc ccttcatca gcatcacccc tgtgtggctg     540
tatgccagac tcatcccctt ccaggaggt gcagtgggct gcggcatacg cctgcccaac     600
ccagacactg acctctactg gttcaccctg taccagtttt tcctggcctt tgccctgcct     660
tttgtggtca tcacagccgc atacgtgagg atcctgcagc gcatgacgtc ctcagtggcc     720
cccgcctccc agcgcagcat ccggctgcgg acaaagaggg tgacccgcac agccatcgcc     780
atctgtctgg tcttctttgt gtgctggca ccctactatg tgctacagct gacccagttg     840
tccatcagcc gcccgaccct cacctttgtc tacttataca tgcgggccat cagcttgggc     900
tatgccaaca gctgcctcaa ccccttttgtg tacatcgtgc tctgtgagac gttccggagt     960
tctttgaagg cctatgggaa tggctactcc agcaacggca cacagggga gcagagtgga    1020 tatcacgtgg aacaggagaa agaaaataaa ctgctgtgtg aagacctccc aggcacggaa    1080
gactttgtgg gccatcaagg tactgtgcct agcgataaca ttgattcaca agggaggaat    1140
tgtagtacaa atgactcact gctgtaa                                       1167

<210> SEQ ID NO 28
<211> LENGTH: 388
<212> TYPE: PRT
<213> ORGANISM: Artificial Sequence
<220> FEATURE:
<223> OTHER INFORMATION: human MCH1R/human beta-2 adrenergic receptor
      C-terminal chimera protein sequence

<400> SEQUENCE: 28

```
Met Asp Leu Glu Ala Ser Leu Leu Pro Thr Gly Pro Asn Ala Ser Asn
1               5                   10                  15

Thr Ser Asp Gly Pro Asp Asn Leu Thr Ser Ala Gly Ser Pro Pro Arg
                20                  25                  30

Thr Gly Ser Ile Ser Tyr Ile Asn Ile Ile Met Pro Ser Val Phe Gly
            35                  40                  45

Thr Ile Cys Leu Leu Gly Ile Ile Gly Asn Ser Thr Val Ile Phe Ala
        50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
                100                 105                 110

Glu Thr Met Cys Thr Leu Ile Thr Ala Met Asp Ala Asn Ser Gln Phe
            115                 120                 125

Thr Ser Thr Tyr Ile Leu Thr Ala Met Ala Ile Asp Arg Tyr Leu Ala
        130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
                180                 185                 190

Gly Cys Gly Ile Arg Leu Pro Asn Pro Asp Thr Asp Leu Tyr Trp Phe
            195                 200                 205

Thr Leu Tyr Gln Phe Phe Leu Ala Phe Ala Leu Pro Phe Val Val Ile
        210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
                260                 265                 270

Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
        290                 295                 300

Cys Leu Asn Pro Phe Val Tyr Ile Val Leu Cys Glu Thr Phe Arg Ser
305                 310                 315                 320

Ser Leu Lys Ala Tyr Gly Asn Gly Tyr Ser Ser Asn Gly Asn Thr Gly
                325                 330                 335

Glu Gln Ser Gly Tyr His Val Glu Gln Glu Lys Glu Asn Lys Leu Leu
            340                 345                 350

Cys Glu Asp Leu Pro Gly Thr Glu Asp Phe Val Gly His Gln Gly Thr
```

-continued

```
            355                 360                 365
Val Pro Ser Asp Asn Ile Asp Ser Gln Gly Arg Asn Cys Ser Thr Asn
    370                 375                 380

Asp Ser Leu Leu
385

<210> SEQ ID NO 29
<211> LENGTH: 6595
<212> TYPE: DNA
<213> ORGANISM: Artificial Sequence
<220> FEATURE:
<223> OTHER INFORMATION: human MCH1R/human beta-2 adrenergic receptor in
      pcDNA3.1Plus(pN125)

<400> SEQUENCE: 29
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca caaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccactagt ccagtgtggt ggaattcctg     960
cagcccgggg gatccgcccc accatggacc tggaagcct cgctgctgcc cactggtccc    1020
aatgccagca cacctctga tggccccgat aacctcactt cggcaggatc acctcctcgc    1080
acggggagca tctcctacat caacatcatc atgccttcgg tgttcggcac catctgcctc    1140
ctgggcatca tcgggaactc cacggtcatc ttcgcggtcg tgaagaagtc caagctgcac    1200
tggtgcaaca acgtccccga catcttcatc atcaacctct cggtagtaga tctcctcttt    1260
ctcctgggca tgcccttcat gatccaccag ctcatgggca tggggtgtg gcactttggg    1320 gagaccatgt gcaccctcat cacggccatg gatgccaata gtcagttcac cagcacctac    1380
atcctgaccg ccatggccat tgaccgctac ctggccactg ccacccccat ctcttccacg    1440
aagttccgga gccctctgt ggccaccctg gtgatctgcc tcctgtgggc cctctccttc    1500
atcagcatca cccctgtgtg gctgtatgcc agactcatcc ccttcccagg aggtgcagtg    1560
ggctgcggca tacgcctgcc caacccagac actgacctct actggttcac cctgtaccag    1620
tttttcctgg cctttgccct gccttttgtg gtcatcacag ccgcatacgt gaggatcctg    1680
cagcgcatga cgtcctcagt ggccccgcc tcccagcgca gcatccggct gcggacaaag    1740
agggtgaccc gcacagccat cgccatctgt ctggtcttct ttgtgtgctg ggcaccctac    1800
```

```
tatgtgctac agctgaccca gttgtccatc agccgcccga ccctcacctt tgtctactta    1860
tacaatgcgg ccatcagctt gggctatgcc aacagctgcc tcaaccccett tgtgtacatc    1920 gtgctctgtg agacgttccg gagttctttg aaggcctatg gaatggcta ctccagcaac    1980 ggcaacacag gggagcagag tggatatcac gtggaacagg agaaagaaaa taaactgctg    2040
tgtgaagacc tcccaggcac ggaagacttt gtgggccatc aaggtactgt gcctagcgat    2100
aacattgatt cacaagggag gaattgtagt acaaatgact cactgctgta agctctagag    2160
ggcccgttta aacccgctga tcagcctcga ctgtgccttc tagttgccag ccatctgttg    2220
tttgcccctc ccccgtgcct tccttgaccc tggaaggtgc cactcccact gtcctttcct    2280
aataaaatga ggaaattgca tcgcattgtc tgagtaggtg tcattctatt ctggggggtg    2340
gggtggggca ggacagcaag ggggaggatt gggaagacaa tagcaggcat gctgggatg    2400 cggtgggctc tatggcttct gaggcggaaa gaaccagctg gggctctagg gggtatcccc    2460
acgcgccctg tagcggcgca ttaagcgcgg cgggtgtggt ggttacgcgc agcgtgaccg    2520
ctacacttgc cagcgcccta gcgcccgctc ctttcgcttt cttcccttcc tttctcgcca    2580
cgttcgccgg ctttccccgt caagctctaa atcggggcat ccctttaggg ttccgattta    2640
gtgctttacg gcacctcgac cccaaaaaac ttgattaggg tgatggttca cgtagtgggc    2700
catcgccctg atagacggtt tttcgccctt gacgttgga gtccacgttc tttaatagtg    2760
gactcttgtt ccaaactgga acaacactca accctatctc ggtctattct tttgatttat    2820
aagggatttt ggggatttcg gcctattggt taaaaaatga gctgatttaa caaaaattta    2880
acgcgaatta attctgtgga atgtgtgtca gttagggtgt ggaaagtccc caggctcccc    2940
aggcaggcag aagtatgcaa agcatgcatc tcaattagtc agcaaccagg tgtggaaagt    3000
ccccaggctc cccagcaggc agaagtatgc aaagcatgca tctcaattag tcagcaacca    3060
tagtcccgcc cctaactccg cccatcccgc cctaactcc gcccagttcc gcccattctc    3120
cgccccatgg ctgactaatt ttttttattt atgcagaggc cgaggccgcc tctgcctctg    3180
agctattcca gaagtagtga ggaggctttt ttggaggcct aggcttttgc aaaaagctcc    3240
cgggagcttg tatatccatt ttcggatctg atcaagagac aggatgagga tcgtttcgca    3300
tgattgaaca agatggattg cacgcaggtt ctccggccgc ttgggtggag aggctattcg    3360
gctatgactg ggcacaacag acaatcggct gctctgatgc cgccgtgttc cggctgtcag    3420
cgcaggggcg cccggttctt tttgtcaaga ccgacctgtc cggtgccctg aatgaactgc    3480
aggacgaggc agcgcggcta tcgtggctgg ccacgacggg cgttccttgc gcagctgtgc    3540
tcgacgttgt cactgaagcg ggaagggact ggctgctatt gggcgaagtg ccggggcagg    3600
atctcctgtc atctcacctt gctcctgccg agaaagtatc catcatggct gatgcaatgc    3660
ggcggctgca tacgcttgat ccggctacct gcccattcga ccaccaagcg aaacatcgca    3720
tcgagcgagc acgtactcgg atggaagccg gtcttgtcga tcaggatgat ctggacgaag    3780
agcatcaggg gctcgcgcca gccgaactgt tcgccaggct caaggcgcgc atgcccgacg    3840
gcgaggatct cgtcgtgacc catggcgatg cctgcttgcc gaatatcatg gtggaaaatg    3900
gccgcttttc tggattcatc gactgtggcc ggctgggtgt ggcggaccgc tatcaggaca    3960
tagcgttggc tacccgtgat attgctgaag agcttggcgg cgaatgggct gaccgcttcc    4020
tcgtgcttta cggtatcgcc gctcccgatt cgcagcgcat cgccttctat cgccttcttg    4080
acgagttctt ctgagcggga ctctggggtt cgaaatgacc gaccaagcga cgcccaacct    4140
gccatcacga gatttcgatt ccaccgccgc cttctatgaa aggttgggct tcggaatcgt    4200
```

-continued

```
tttccgggac gccggctgga tgatcctcca gcgcggggat ctcatgctgg agttcttcgc    4260 ccacccaac ttgtttattg cagcttataa tggttacaaa taaagcaata gcatcacaaa    4320
tttcacaaat aaagcatttt tttcactgca ttctagttgt ggtttgtcca aactcatcaa    4380
tgtatcttat catgtctgta taccgtcgac ctctagctag agcttggcgt aatcatggtc    4440
atagctgttt cctgtgtgaa attgttatcc gctcacaatt ccacacaaca tacgagccgg    4500
aagcataaag tgtaaagcct ggggtgccta atgagtgagc taactcacat taattgcgtt    4560
gcgctcactg cccgctttcc agtcgggaaa cctgtcgtgc cagctgcatt aatgaatcgg    4620
ccaacgcgcg gggagaggcg gtttgcgtat tgggcgctct tccgcttcct cgctcactga    4680
ctcgctgcgc tcggtcgttc ggctgcggcg agcggtatca gctcactcaa aggcggtaat    4740
acggttatcc acagaatcag gggataacgc aggaaagaac atgtgagcaa aaggccagca    4800
aaaggccagg aaccgtaaaa aggccgcgtt gctggcgttt ttccataggc tccgcccccc    4860
tgacgagcat cacaaaaatc gacgctcaag tcagaggtgg cgaaacccga caggactata    4920
aagataccag gcgtttcccc ctggaagctc cctcgtgcgc tctcctgttc cgaccctgcc    4980
gcttaccgga tacctgtccg cctttctccc ttcgggaagc gtggcgcttt ctcaatgctc    5040
acgctgtagg tatctcagtt cggtgtaggt cgttcgctcc aagctgggct gtgtgcacga    5100
accccccgtt cagcccgacc gctgcgcctt atccggtaac tatcgtcttg agtccaaccc    5160
ggtaagacac gacttatcgc cactggcagc agccactggt aacaggatta gcagagcgag    5220
gtatgtaggc ggtgctacag agttcttgaa gtggtggcct aactacggct acactagaag    5280
gacagtattt ggtatctgcg ctctgctgaa gccagttacc ttcggaaaaa gagttggtag    5340
ctcttgatcc ggcaaacaaa ccaccgctgg tagcggtggt ttttttgttt gcaagcagca    5400
gattacgcgc agaaaaaaag gatctcaaga agatcctttg atcttttcta cggggtctga    5460
cgctcagtgg aacgaaaact cacgttaagg gattttggtc atgagattat caaaaaggat    5520
cttcacctag atccttttaa attaaaaatg aagttttaaa tcaatctaaa gtatatatga    5580
gtaaacttgg tctgacagtt accaatgctt aatcagtgag gcacctatct cagcgatctg    5640
tctatttcgt tcatccatag ttgcctgact ccccgtcgtg tagataacta cgatacggga    5700
gggcttacca tctggcccca gtgctgcaat gataccgcga gacccacgct caccggctcc    5760
agatttatca gcaataaacc agccagccgg aagggccgag cgcagaagtg gtcctgcaac    5820
tttatccgcc tccatccagt ctattaattg ttgccgggaa gctagagtaa gtagttcgcc    5880
agttaatagt ttgcgcaacg ttgttgccat tgctacaggc atcgtggtgt cacgctcgtc    5940
gtttggtatg gcttcattca gctccggttc ccaacgatca aggcgagtta catgatcccc    6000
catgttgtgc aaaaaagcgg ttagctcctt cggtcctccg atcgttgtca agtaagtt    6060 ggccgcagtg ttatcactca tggttatggc agcactgcat aattctctta ctgtcatgcc    6120
atccgtaaga tgcttttctg tgactggtga gtactcaacc aagtcattct gagaatagtg    6180
tatgcggcga ccgagttgct cttgcccggc gtcaatacgg gataataccg cgccacatag    6240
cagaacttta aaagtgctca tcattggaaa acgttcttcg ggcgaaaac tctcaaggat    6300 cttaccgctg ttgagatcca gttcgatgta acccactcgt gcacccaact gatcttcagc    6360
atcttttact ttcaccagcg tttctgggtg agcaaaaaca ggaaggcaaa atgccgcaaa    6420
aaagggaata agggcgacac ggaaatgttg aatactcata ctcttccttt ttcaatatta    6480
ttgaagcatt tatcagggtt attgtctcat gagcggatac atatttgaat gtatttagaa    6540
```

```
aaataaacaa ataggggttc cgcgcacatt tccccgaaaa gtgccacctg acgtc        6595
```

<210> SEQ ID NO 30
<211> LENGTH: 31
<212> TYPE: PRT
<213> ORGANISM: homo sapiens

<400> SEQUENCE: 30

Pro Pro Arg Ser Gly Ser Val Ser Tyr Ile Asn Ile Ile Met Pro Ser
1               5                   10                  15

Val Phe Gly Thr Ile Cys Leu Leu Gly Ile Ile Gly Asn Ser Met
            20                  25                  30

<210> SEQ ID NO 31
<211> LENGTH: 23
<212> TYPE: DNA
<213> ORGANISM: Artificial Sequence
<220> FEATURE:
<223> OTHER INFORMATION: human MCH1R forward primer

<400> SEQUENCE: 31

```
ccaccatgga cctggaagcc tcg                                             23
```

<210> SEQ ID NO 32
<211> LENGTH: 20
<212> TYPE: DNA
<213> ORGANISM: Artificial Sequence
<220> FEATURE:
<223> OTHER INFORMATION: human MCH1R reverse primer

<400> SEQUENCE: 32

```
agggtggcag gggaagtatc                                                 20
```

<210> SEQ ID NO 33
<211> LENGTH: 1023
<212> TYPE: DNA
<213> ORGANISM: Macaca fascicularis

<400> SEQUENCE: 33

```
atgaatccat ttcactcatc ttgttggaac acctctgccg aactttcaaa caaatcctgg     60
aataaagagt ttgcttatca aactgccagt gttgtagata cagtcatcct cccttccatg    120
attgggatta tctgttcaac agggctggtt ggcaacatcc tcattgtatt cactataata    180
aggtccagaa aaaaacagt ccctgacatc tatatctgca acctggctgt ggctgatttg    240
gtccacatcg ttggaatgcc ttttcttatt caccagtggg cccgaggggg agagtgggta    300
tttgggggc ctctctgcac catcatcaca tccctggata cttgtaacca atttgcctgt    360
agtgccatca tgactgtaat gagtgtggac aggtactttg ccctcgtcca accatttcga    420
ctgacgagtt ggaggacaag gtacaagacc atccggatca atttgggcct ttgggcagct    480
tcctttatcc tggcattgcc tgtctggatc tactcgaagg tcatcaaatt taaagacggt    540
gtcgagagtt gtgcttttga tttgacatcc cctgacgatg tactctggta tacactttat    600
ttgacaataa caactttctt tttccctcta cccttgattt tggtgtgcta tattttaatt    660
ttatgctata cttgggagat gtatcaacag aataaggatg ccagatgttg caatcccagc    720
gtaccaaaac agagagtgat gaagttgaca agatggtgc tggtgctggt ggcagtcttt    780
atcctaagtg ctgccccctta tcatgtgata caactggtga acttacagat ggaacagccc    840
acactggcct tctatgtggg ttattacctc tccatctgtc tcagctatgc cagcagcagc    900
attaacccctt ttctctacat cctgctgagt ggaaattttcc agaaacgtct gcctcaaatc    960
```

-continued caaggagag tgactgacaa ggaaatcaaa aatatgggaa acactctgaa atcacacttt 1020
tag 1023

<210> SEQ ID NO 34
<211> LENGTH: 340
<212> TYPE: PRT
<213> ORGANISM: Macaca fascicularis

<400> SEQUENCE: 34

```
Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Val Thr Asp Lys Glu Ile Lys Asn Met Gly Asn Thr Leu
                325                 330                 335

Lys Ser His Phe
            340
```

<210> SEQ ID NO 35
<211> LENGTH: 1023
<212> TYPE: DNA
<213> ORGANISM: Macaca fascicularis

<400> SEQUENCE: 35

```
atgaatccat tcactcatc ttgttggaac acctctgccg aactttcaaa caaatcctgg      60
aataaagagt ttgcttatca aactgccagt gttgtagata cagtcatcct cctttccatg    120
attgggatta tctgttcaac agggctggtt ggcaacatcc tcattgtatt cactataata    180
aggtccagaa aaaaaacagt ccctgacatc tatatctgca acctggctgt ggctgatttg    240
gtccacatcg ttggaatgcc ttttcttatt caccagtggg cccgaggggg agagtgggta    300
tttgggggc ctctctgcac catcatcaca tccctgata cttgtaacca atttgcctgt      360
agtgccatca tgactgtaat gagtgtggac aggtacttttg ccctcgtcca accatttcga   420
ctgacgagtt ggaggacaag gtacaagacc atccggatca atttgggcct ttgggcagct   480
tcctttatcc tggcattgcc tgtctggatc tactcgaagg tcatcaaatt taaagacggt   540
gtcgagagtt gtgcttttga tttgacatcc cctgacgatg tactctggta tactttat    600
ttgacaataa caactttctt tttccctcta cccttgattt tggtgtgcta tattttaatt  660
ttatgctata cttgggagat gtatcaacag aataaggatg ccagatgttg caatcccagc  720
gtaccaaaac agagagtgat gaagttgaca agatggtgc tggtgctggt ggcagtcttt   780
atcctaagtg ctgcccctta tcatgtgata caactggtga acttacagat ggaacagccc  840
acactggcct tctatgtggg ttattacctc tccatctgtc tcagctatgc cagcagcagc  900
attaacccttt ttctctacat cctgctgagt ggaaatttcc agaaacgtct gcctcaaatc  960
caaaggagag tgactgacaa ggaaatcaaa aatatgggaa acactctgaa atcacacttt  1020
tag                                                                1023
```

<210> SEQ ID NO 36
<211> LENGTH: 340
<212> TYPE: PRT
<213> ORGANISM: Macaca fascicularis

<400> SEQUENCE: 36

```
Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
    130                 135                 140
```

```
                Arg Thr Arg Tyr Lys Thr Ile Arg Ile Asn Leu Gly Leu Trp Ala Ala
                145                 150                 155                 160

Ser Phe Ile Leu Ala Leu Pro Val Trp Ile Tyr Ser Lys Val Ile Lys
                                165                 170                 175

Phe Lys Asp Gly Val Glu Ser Cys Ala Phe Asp Leu Thr Ser Pro Asp
                            180                 185                 190

Asp Val Leu Trp Tyr Thr Leu Tyr Leu Thr Ile Thr Thr Phe Phe Phe
                                195                 200                 205

Pro Leu Pro Leu Ile Leu Val Cys Tyr Ile Leu Ile Leu Cys Tyr Thr
                            210                 215                 220

Trp Glu Met Tyr Gln Gln Asn Lys Asp Ala Arg Cys Cys Asn Pro Ser
                225                 230                 235                 240

Val Pro Lys Gln Arg Val Met Lys Leu Thr Lys Met Val Leu Val Leu
                                245                 250                 255

Val Ala Val Phe Ile Leu Ser Ala Ala Pro Tyr His Val Ile Gln Leu
                            260                 265                 270

Val Asn Leu Gln Met Glu Gln Pro Thr Leu Ala Phe Tyr Val Gly Tyr
                                275                 280                 285

Tyr Leu Ser Ile Cys Leu Ser Tyr Ala Ser Ser Ile Asn Pro Phe
                            290                 295                 300

Leu Tyr Ile Leu Leu Ser Gly Asn Phe Gln Lys Arg Leu Pro Gln Ile
                305                 310                 315                 320

Gln Arg Arg Val Thr Asp Lys Glu Ile Lys Asn Met Gly Asn Thr Leu
                                325                 330                 335

Lys Ser His Phe
                            340

<210> SEQ ID NO 37
<211> LENGTH: 1023
<212> TYPE: DNA
<213> ORGANISM: Macaca fascicularis

<400> SEQUENCE: 37
atgaatccat tcactcatc  ttgttggaac acctctgccg aactttcaaa caaatcctgg    60
aataaagagt tgcttatca  aactgccagt gttgtagata cagtcatcct cccttccatg   120
attgggatta tctgttcaac agggctggtt ggcaacatcc tcattgtatt cactataata   180
aggtccagaa aaaaaacagt ccctgacatc tatatctgca acctggctgt ggctgatttg   240
gtccacatcg ttggaatgcc ttttcttatt caccagtggg cccgaggggg agagtgggta   300 tttgggggc  ctctctgcac catcatcaca tccctggata cttgtaacca atttgcctgt   360
agtgccatca tgactgtaat gagtgtggac aggtactttg ccctcgtcca accatttcga   420
ctgacaagtt ggagaacaag gtacaagacc atccggatca atttgggcct tgggcagct    480 tcctttatcc tggcattgcc tgtctggatc tactcgaagg tcatcaaatt taaagacggt   540
gtcgagagtt gtgcttttga tttgacatcc cctgacgatg tactctggta tacactttat   600
ttgacaataa caactttctt tttcccctcta cccttgattt tggtgtgcta tattttaatt   660
ttatgctata cttgggagat gtatcaacag aataaggatg ccagatgttg caatcccagc   720
gtaccaaaac agagagtgat gaagttgaca aagatggtgc tggtgctggt ggcagtcttt   780
atcctaagtg ctgcccctta tcatgtgata caactggtga acttacagat ggaacagccc   840
acactggcct tctatgtggg ttattacctc tccatctgtc tcagctatgc cagcagcagc   900 attaacccctt ttctctacat cctgctgagt ggaaattttc agaaacgtct gcctcaaatc   960
```

```
caaaggagag tgactgacaa ggaaatcaaa aatatgggaa acactctgaa atcacacttt    1020
tag                                                                 1023
```

<210> SEQ ID NO 38
<211> LENGTH: 993
<212> TYPE: DNA
<213> ORGANISM: Canis sp.

<400> SEQUENCE: 38

```
atgtattcac ttcactcatc ctgttggaac acctctgctg aacctttgaa caaatcctgc     60
aataaagagt ttgcttatca caccctcagc attttagata caatcatcct cccttctatg    120
attgggatta tctgttcaat ggggctagtt ggcaacatcc tcattgtatt cactataata    180
aggtccagga aaaaaccat tcctgacatt tatatctgca acctggctgt ggctgatctg     240
gtccacatca ttggaatgcc atttcttatt catcagtggg cccggggagg agagtgggtg    300 tttgggggc cctctgcac cattatcaca tccctggata cctgcaacca gtttgcctgt     360
agtgccatca tgactgtgat gagtatagac aggtacttgg ctctcgtcca accatttcga    420
cttacaagtt ggagaacgag gtacaagacc atccgcatca atttgggcct ttgggcagct    480
tccttcattc tggcgctgcc tgtctgggtc tactcgaagg tcatcaaatt taaagacggc    540
gtggagagtt gtgctttga tttaacatcc cctgacgatg tactccggta tacactttat    600
ttgacgataa aactttttt tttccctttg cctttgattt tggtgtgcta tattttaatt     660
ttatgctata cttgggagat gtatcaacag aataaagatg caagatgtta caatcccagt    720
gttccaaaag agagagtgat gaagctgaca agatggtgc tggtgctggt ggcggtcttt     780
atcctaagtg ctgcccccta ccacgtgata caactggtga acttaaagat gcagcagccc    840
acactggcct tccatgtagg ctattatctc tccatctgtt tcagctatgc cagcagcagc    900 attaacccctt tcctctacat catgctgagt ggaaatttcc ggaaacgcct acctcaagta    960
caaaggagag tgactgagaa atcaacaata tag                                 993
```

<210> SEQ ID NO 39
<211> LENGTH: 330
<212> TYPE: PRT
<213> ORGANISM: Canis sp.

<400> SEQUENCE: 39

```
Met Tyr Ser Leu His Ser Ser Cys Trp Asn Thr Ser Ala Glu Pro Leu
  1               5                  10                  15

Asn Lys Ser Cys Asn Lys Glu Phe Ala Tyr His Thr Leu Ser Ile Leu
             20                  25                  30

Asp Thr Ile Ile Leu Pro Ser Met Ile Gly Ile Ile Cys Ser Met Gly
         35                  40                  45

Leu Val Gly Asn Ile Leu Ile Val Phe Thr Ile Arg Ser Arg Lys
     50                  55                  60

Lys Thr Ile Pro Asp Ile Tyr Ile Cys Asn Leu Ala Val Ala Asp Leu
 65                  70                  75                  80

Val His Ile Ile Gly Met Pro Phe Leu Ile His Gln Trp Ala Arg Gly
                 85                  90                  95

Gly Glu Trp Val Phe Gly Gly Pro Leu Cys Thr Ile Thr Ser Leu
                100                 105                 110

Asp Thr Cys Asn Gln Phe Ala Cys Ser Ala Ile Met Thr Val Met Ser
            115                 120                 125

Ile Asp Arg Tyr Leu Ala Leu Val Gln Pro Phe Arg Leu Thr Ser Trp
```

```
                    130              135             140
Arg Thr Arg Tyr Lys Thr Ile Arg Ile Asn Leu Gly Leu Trp Ala Ala
145                 150             155                 160

Ser Phe Ile Leu Ala Leu Pro Val Trp Val Tyr Ser Lys Val Ile Lys
                165                 170                 175

Phe Lys Asp Gly Val Glu Ser Cys Ala Phe Asp Leu Thr Ser Pro Asp
                180                 185                 190

Asp Val Leu Arg Tyr Thr Leu Tyr Leu Thr Ile Thr Thr Phe Phe
                195                 200             205

Pro Leu Pro Leu Ile Leu Val Cys Tyr Ile Leu Ile Leu Cys Tyr Thr
            210                 215                 220

Trp Glu Met Tyr Gln Gln Asn Lys Asp Ala Arg Cys Tyr Asn Pro Ser
225                 230                 235                 240

Val Pro Lys Glu Arg Val Met Lys Leu Thr Lys Met Val Leu Val Leu
                245                 250                 255

Val Ala Val Phe Ile Leu Ser Ala Ala Pro Tyr His Val Ile Gln Leu
                260                 265                 270

Val Asn Leu Lys Met Gln Gln Pro Thr Leu Ala Phe His Val Gly Tyr
                275                 280                 285

Tyr Leu Ser Ile Cys Phe Ser Tyr Ala Ser Ser Ser Ile Asn Pro Phe
            290                 295                 300

Leu Tyr Ile Met Leu Ser Gly Asn Phe Arg Lys Arg Leu Pro Gln Val
305                 310                 315                 320

Gln Arg Arg Val Thr Glu Lys Ser Thr Ile
                325                 330
```

<210> SEQ ID NO 40
<211> LENGTH: 1062
<212> TYPE: DNA
<213> ORGANISM: Artificial Sequence
<220> FEATURE:
<223> OTHER INFORMATION: Cynomolgus macaque MCH1R DNA sequence with BspE
      site added for C-terminal chimeras

<400> SEQUENCE: 40

```
atggacctgg aagcctcgct gctgcccact ggtcccaaca ccagcaacac ctctgatggc    60
cccgataacc tcacctcggc aggatcacct cctcgctcag ggagcgtctc ctacatcaac   120
atcatcatgc cttcggtgtt cggcaccatc tgcctcctgg gcatcatcgg aactccatg    180 gtcatcttcg cggtcgtgaa gaagtccaag ctgcactggt gcaacaatgt ccccgacatc   240
ttcatcatca acctctcggt ggtggatctc ctctttctcc tgggcatgcc cttcatgatc   300
caccagctca tgggcaatgg ggtgtggcac tttggggaga ccatgtgcac cctcatcacg   360
gccatggatg ccaatagtca gttcaccagc acctacatcc tgaccgccat ggccattgac   420
cgctacctgg ccaccgtcca ccccatctct ccacaaagt tccggaagcc ctctgtggcc    480
accctggtga tctgcctcct gtgggccctc ccttcatca gcatcacccc cgtgtggttg    540
tatgccagac tcatcccctt ccaggaggt gcagtgggct gcggcatccg cttgcccaac    600
ccggacactg acctttactg gttcaccctg taccagtttt tcctggcctt tgccctgccc    660
ttcgtggtca tcacggccgc atacgtgagg atcctgcagc gcatgacgtc ctcagtggcc    720
cccgcctccc agcgcagcat ccggctgcgg acaaagaggg tgacccgcac agccatcgcc    780
atctgcctgg tcttctttgt gtgctgggca ccctactatg tgctacagct gacccagttg    840
tccatcagcc gcccgaccct cacctttgtc tacctgtaca atgcggccat cagcttgggc    900
```

-continued

```
tacgccaaca gctgcctcaa ccccttttgtg tacattgtgc tctgcgagac gttccggaaa    960
cgcttggtcc tttcggtgaa gcctgcagcc caggggcagc ttcgcgctgt cagcaacgct   1020
cagacggctg acgaggagag gacagaaagc aaaggtacct ga                      1062
```

<210> SEQ ID NO 41
<211> LENGTH: 1074
<212> TYPE: DNA
<213> ORGANISM: Artificial Sequence
<220> FEATURE:
<223> OTHER INFORMATION: Cynomolgus macaque MCH1R/human NPY1 IC3 chimera

<400> SEQUENCE: 41

```
atggacctgg aagcctcgct gctgcccact ggtcccaaca ccagcaacac ctctgatggc     60
cccgataacc tcacctcggc aggatcacct cctcgctcag ggagcgtctc ctacatcaac    120
atcatcatgc cttcggtgtt cggcaccatc tgcctcctgg catcatcgg aactccatg    180 gtcatcttcg cggtcgtgaa gaagtccaag ctgcactggt gcaacaatgt ccccgacatc    240
ttcatcatca acctctcggt ggtggatctc ctctttctcc tgggcatgcc cttcatgatc    300
caccagctca tgggcaatgg ggtgtggcac tttggggaga ccatgtgcac cctcatcacg    360
gccatggatg ccaatagtca gttcaccagc acctacatcc tgaccgccat ggccattgac    420
cgctacctgg ccaccgtcca ccccatctct tccacaaagt tccggaagcc ctctgtggcc    480
accctggtga tctgcctcct gtgggccctc ccttcatca gcatcacccc cgtgtggttg    540
tatgccagac tcatcccctt ccaggaggt gcagtgggct gcggcatccg cttgcccaac    600
ccggacactg acctttactg gttcaccctg taccagttt tcctggcctt tgccctgccc    660
ttcgtggtca tcacggccgc atacgtgagg atcctgata gcctaaaaag gagaaacaac    720
atgatggaca agatgagaga caataagtac aggtccagtg aaaccaaaag ggtgacccgc    780
acagccatcg ccatctgcct ggtcttcttt gtgtgctggg ccctacta tgtgctacag    840 ctgacccagt tgtccatcag ccgcccgacc ctcacctttg tctacctgta caatgcggcc    900
atcagcttgg gctacgccaa cagctgcctc aaccccttg tgtacattgt gctctgcgag    960
acgttccgca aacgcttggt cctttcggtg aagcctgcag cccaggggca gcttcgcgct   1020
gtcagcaacg ctcagacggc tgacgaggag aggacagaaa gcaaaggtac ctga         1074
```

<210> SEQ ID NO 42
<211> LENGTH: 357
<212> TYPE: PRT
<213> ORGANISM: artificial sequence
<220> FEATURE:
<223> OTHER INFORMATION: Cynomolgus macaque MCH1R/human NPY1 IC3 chimera
    - amino acid sequence

<400> SEQUENCE: 42

```
Met Asp Leu Glu Ala Ser Leu Leu Pro Thr Gly Pro Asn Thr Ser Asn
1               5                  10                   15

Thr Ser Asp Gly Pro Asp Asn Leu Thr Ser Ala Gly Ser Pro Pro Arg
            20                  25                   30

Ser Gly Ser Val Ser Tyr Ile Asn Ile Ile Met Pro Ser Val Phe Gly
        35                  40                   45

Thr Ile Cys Leu Leu Gly Ile Ile Gly Asn Ser Met Val Ile Phe Ala
    50                  55                   60

Val Val Lys Lys Ser Lys Leu His Trp Cys Asn Asn Val Pro Asp Ile
65                  70                  75                   80

Phe Ile Ile Asn Leu Ser Val Val Asp Leu Leu Phe Leu Leu Gly Met
```

```
                    85                  90                  95
Pro Phe Met Ile His Gln Leu Met Gly Asn Gly Val Trp His Phe Gly
            100                 105                 110
Glu Thr Met Cys Thr Leu Ile Thr Ala Met Asp Ala Asn Ser Gln Phe
        115                 120                 125
Thr Ser Thr Tyr Ile Leu Thr Ala Met Ala Ile Asp Arg Tyr Leu Ala
    130                 135                 140
Thr Val His Pro Ile Ser Ser Thr Lys Phe Arg Lys Pro Ser Val Ala
145                 150                 155                 160
Thr Leu Val Ile Cys Leu Leu Trp Ala Leu Ser Phe Ile Ser Ile Thr
                165                 170                 175
Pro Val Trp Leu Tyr Ala Arg Leu Ile Pro Phe Pro Gly Gly Ala Val
            180                 185                 190
Gly Cys Gly Ile Arg Leu Pro Asn Pro Asp Thr Asp Leu Tyr Trp Phe
        195                 200                 205
Thr Leu Tyr Gln Phe Phe Leu Ala Phe Ala Leu Pro Phe Val Val Ile
    210                 215                 220
Thr Ala Ala Tyr Val Arg Ile Leu Ile Arg Leu Lys Arg Arg Asn Asn
225                 230                 235                 240
Met Met Asp Lys Met Arg Asp Asn Lys Tyr Arg Ser Ser Glu Thr Lys
                245                 250                 255
Arg Val Thr Arg Thr Ala Ile Ala Ile Cys Leu Val Phe Phe Val Cys
            260                 265                 270
Trp Ala Pro Tyr Tyr Val Leu Gln Leu Thr Gln Leu Ser Ile Ser Arg
        275                 280                 285
Pro Thr Leu Thr Phe Val Tyr Leu Tyr Asn Ala Ala Ile Ser Leu Gly
    290                 295                 300
Tyr Ala Asn Ser Cys Leu Asn Pro Phe Val Tyr Ile Val Leu Cys Glu
305                 310                 315                 320
Thr Phe Arg Lys Arg Leu Val Leu Ser Val Lys Pro Ala Ala Gln Gly
                325                 330                 335
Gln Leu Arg Ala Val Ser Asn Ala Gln Thr Ala Asp Glu Glu Arg Thr
            340                 345                 350
Glu Ser Lys Gly Thr
        355

<210> SEQ ID NO 43
<211> LENGTH: 1128
<212> TYPE: DNA
<213> ORGANISM: Artificial Sequence
<220> FEATURE:
<223> OTHER INFORMATION: Cynomolgus macaque MCH1R/human NPY1
      C-terminal chimera

<400> SEQUENCE: 43
atggacctgg aagcctcgct gctgcccact ggtcccaaca ccagcaacac ctctgatggc        60
cccgataacc tcacctcggc aggatcacct cctcgctcag ggagcgtctc ctacatcaac       120
atcatcatgc cttcggtgtt cggcaccatc tgcctcctgg gcatcatcgg gaactccatg       180
gtcatcttcg cggtcgtgaa gaagtccaag ctgcactggt gcaacaatgt ccccgacatc       240
ttcatcatca acctctcggt ggtggatctc ctctttctcc tgggcatgcc cttcatgatc       300
caccagctca tgggcaatgg ggtgtggcac tttggggaga ccatgtgcac cctcatcacg       360
gccatggatg ccaatagtca gttcaccagc acctacatcc tgaccgccat ggccattgac       420
cgctacctgg ccaccgtcca ccccatctct tccacaaagt tccggaagcc ctctgtggcc       480
```

-continued

```
acctggtga tctgcctcct gtgggccctc tccttcatca gcatcacccc cgtgtggttg      540
tatgccagac tcatcccctt cccaggaggt gcagtgggct gcggcatccg cttgcccaac     600
ccggacactg acctttactg gttcacctg taccagtttt tcctggcctt tgccctgccc     660
ttcgtggtca tcacggccgc atacgtgagg atcctgcagc gcatgacgtc ctcagtggcc     720
cccgcctccc agcgcagcat ccggctgcgg acaaagaggg tgacccgcac agccatcgcc     780
atctgcctgg tcttctttgt gtgctgggca ccctactatg tgctacagct gacccagttg     840
tccatcagcc gcccgaccct cacctttgtc tacctgtaca atgcggccat cagcttgggc     900
tacgccaaca gctgcctcaa ccccttttgtg tacattgtgc tctgcgagac gttccggaga    960
gacttgcagt tcttcttcaa cttttgtgat ttccggtctc gggatgatga ttatgaaaca    1020
atagccatgt ccacgatgca cacagatgtt tccaaaactt ctttgaagca agcaagccca    1080
gtcgcattta aaaaaatcaa caacaatgat gataatgaaa aaatctga                 1128
```

<210> SEQ ID NO 44
<211> LENGTH: 375
<212> TYPE: PRT
<213> ORGANISM: Artificial Sequence
<220> FEATURE:
<223> OTHER INFORMATION: Cynomolgus macaque MCH1R/human NPY1 C-terminal chimera - amino acid sequence

<400> SEQUENCE: 44

```
Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
            20                  25                  30

Ser Gly Ser Val Ser Tyr Ile Asn Ile Ile Met Pro Ser Val Phe Gly
        35                  40                  45

Thr Ile Cys Leu Leu Gly Ile Ile Gly Asn Ser Met Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240
```

```
             Pro Ala Ser Gln Arg Ser Ile Arg Leu Arg Thr Lys Arg Val Thr Arg
                             245                 250                 255

Thr Ala Ile Ala Ile Cys Leu Val Phe Phe Val Cys Trp Ala Pro Tyr
                         260                 265                 270

Tyr Val Leu Gln Leu Thr Gln Leu Ser Ile Ser Arg Pro Thr Leu Thr
                     275                 280                 285

Phe Val Tyr Leu Tyr Asn Ala Ala Ile Ser Leu Gly Tyr Ala Asn Ser
                 290                 295                 300

Cys Leu Asn Pro Phe Val Tyr Ile Val Leu Cys Glu Thr Phe Arg Arg
             305                 310                 315                 320

Asp Leu Gln Phe Phe Asn Phe Cys Asp Phe Arg Ser Arg Asp Asp
                             325                 330                 335

Asp Tyr Glu Thr Ile Ala Met Ser Thr Met His Thr Asp Val Ser Lys
                         340                 345                 350

Thr Ser Leu Lys Gln Ala Ser Pro Val Ala Phe Lys Lys Ile Asn Asn
                     355                 360                 365

Asn Asp Asp Asn Glu Lys Ile
                 370                 375

<210> SEQ ID NO 45
<211> LENGTH: 1167
<212> TYPE: DNA
<213> ORGANISM: Artificial Sequence
<220> FEATURE:
<223> OTHER INFORMATION: Cynomolgus macaque MCH1R/human beta-2
      adrenergic receptor C-terminal chimera

<400> SEQUENCE: 45
atggacctgg aagcctcgct gctgcccact ggtcccaaca ccagcaacac ctctgatggc     60
cccgataacc tcacctcggc aggatcacct cctcgctcag ggagcgtctc ctacatcaac    120
atcatcatgc cttcggtgtt cggcaccatc tgcctcctgg gcatcatcgg gaactccatg    180
gtcatcttcg cggtcgtgaa gagtccaag ctgcactggt gcaacaatgt ccccgacatc    240
ttcatcatca acctctcggt ggtggatctc tctttctcc tgggcatgcc cttcatgatc    300
caccagctca tgggcaatgg ggtgtggcac tttgggagag ccatgtgcac cctcatcacg    360
gccatggatg ccaatagtca gttcaccagc acctacatcc tgaccgccat ggccattgac    420
cgctacctgg ccaccgtcca ccccatctct tccacaaagt tccggaagcc ctctgtggcc    480
accctggtga tctgcctcct gtgggccctc tccttcatca gcatcacccc cgtgtgttg    540 tatgccagac tcatcccctt cccaggaggt gcagtgggct cggcatccg cttgcccaac    600 ccggacactg acctttactg gttcaccctg taccagtttt tcctggcctt tgccctgccc    660
ttcgtggtca tcacggccgc atacgtgagg atcctgcagc gcatgacgtc ctcagtggcc    720
cccgcctccc agcgcagcat ccggctgcgg acaaagaggg tgaccgcac agccatcgcc    780 atctgcctgg tcttctttgt gtgctgggca ccctactatg tgctacagct gacccagttg    840
tccatcagcc gcccgaccct cacctttgtc tacctgtaca atgcggccat cagcttgggc    900
tacgccaaca gctgcctcaa ccccttgtg tacattgtgc tctgcgagac gttccggagt    960
tctttgaagg cctatgggaa tggctactcc agcaacggca acacagggga gcagagtgga   1020
tatcacgtgg aacaggagaa agaaaataaa ctgctgtgtg aagacctccc aggcacggaa   1080
gactttgtgg gccatcaagg tactgtgcct agcgataaca ttgattcaca agggaggaat   1140
tgtagtacaa atgactcact gctgtaa                                       1167
```

-continued

<210> SEQ ID NO 46
<211> LENGTH: 388
<212> TYPE: PRT
<213> ORGANISM: Artificial Sequence
<220> FEATURE:
<223> OTHER INFORMATION: Cynomolgus macaque MCH1R/human beta-2
      adrenergic receptor C-terminal chimera - amino acid sequence

<400> SEQUENCE: 46

```
Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
            20                  25                  30

Ser Gly Ser Val Ser Tyr Ile Asn Ile Ile Met Pro Ser Val Phe Gly
        35                  40                  45

Thr Ile Cys Leu Leu Gly Ile Gly Asn Ser Met Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Ser
305                 310                 315                 320

Ser Leu Lys Ala Tyr Gly Asn Gly Tyr Ser Ser Asn Gly Asn Thr Gly
                325                 330                 335

Glu Gln Ser Gly Tyr His Val Glu Gln Glu Lys Glu Asn Lys Leu Leu
            340                 345                 350

Cys Glu Asp Leu Pro Gly Thr Glu Asp Phe Val Gly His Gln Gly Thr
        355                 360                 365
```

Val Pro Ser Asp Asn Ile Asp Ser Gln Gly Arg Asn Cys Ser Thr Asn
    370                 375                 380

Asp Ser Leu Leu
385

<210> SEQ ID NO 47
<211> LENGTH: 1059
<212> TYPE: DNA
<213> ORGANISM: Artificial Sequence
<220> FEATURE:
<223> OTHER INFORMATION: Cynomolgus macaque MCH1R/MCH2R N-terminal
      chimera

<400> SEQUENCE: 47

| | | | | | |
|---|---|---|---|---|---|
| atgaatccat | ttcactcatc | ttgttggaac | acctctgccg | aactttcaaa | caaatcctgg | 60 |
| aataaagagt | ttgcttatca | aactgccagt | gttgtagata | ccgtctccta | catcaacatc | 120 |
| atcatgcctt | cggtgttcgg | caccatctgc | ctcctgggca | tcatcgggaa | ctccatggtc | 180 |
| atcttcgcgg | tcgtgaagaa | gtccaagctg | cactggtgca | acaatgtccc | cgacatcttc | 240 |
| atcatcaacc | tctcggtggt | ggatctcctc | tttctcctgg | gcatgccctt | catgatccac | 300 |
| cagctcatgg | gcaatggggt | gtggcacttt | ggggagacca | tgtgcaccct | catcacggcc | 360 |
| atggatgcca | atagtcagtt | caccagcacc | tacatcctga | ccgccatggc | cattgaccgc | 420 |
| tacctggcca | ccgtccaccc | catctcttcc | acaaagttcc | ggaagccctc | tgtggccacc | 480 |
| ctggtgatct | gcctcctgtg | ggcccctctcc | ttcatcagca | tcaccccgt | gtggttgtat | 540 |
| gccagactca | tccccttccc | aggaggtgca | gtgggctgcg | gcatccgctt | gcccaacccg | 600 |
| gacactgacc | tttactggtt | caccctgtac | cagttttttcc | tggcctttgc | cctgcccttc | 660 |
| gtggtcatca | cggccgcata | cgtgaggatc | ctgcagcgca | tgacgtcctc | agtggccccc | 720 |
| gcctcccagc | gcagcatccg | gctgcggaca | aagagggtga | cccgcacagc | catcgccatc | 780 |
| tgcctggtct | tctttgtgtg | ctgggcaccc | tactatgtgc | tacagctgac | ccagttgtcc | 840 |
| atcagccgcc | cgaccctcac | ctttgtctac | ctgtacaatg | cggccatcag | cttgggctac | 900 |
| gccaacagct | gcctcaaccc | cttttgtgtac | attgtgctct | gcgagacgtt | ccgcaaacgc | 960 |
| ttggtccttt | cggtgaagcc | tgcagcccag | ggcagcttc | gcgctgtcag | caacgctcag | 1020 |
| acggctgacg | aggagaggac | agaaagcaaa | ggtacctga | | | 1059 |

<210> SEQ ID NO 48
<211> LENGTH: 352
<212> TYPE: PRT
<213> ORGANISM: Artificial Sequence
<220> FEATURE:
<223> OTHER INFORMATION: Cynomolgus macaque MCH1R/MCH2R N-terminal
      chimera - amino acid sequence

<400> SEQUENCE: 48

Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ser Tyr Ile Asn Ile Ile Met Pro Ser Val Phe Gly Thr
        35                  40                  45

Ile Cys Leu Leu Gly Ile Ile Gly Asn Ser Met Val Ile Phe Ala Val
    50                  55                  60

Val Lys Lys Ser Lys Leu His Trp Cys Asn Asn Val Pro Asp Ile Phe
65                  70                  75                  80

```
Ile Ile Asn Leu Ser Val Val Asp Leu Leu Phe Leu Leu Gly Met Pro
                85                  90                  95
Phe Met Ile His Gln Leu Met Gly Asn Gly Val Trp His Phe Gly Glu
            100                 105                 110
Thr Met Cys Thr Leu Ile Thr Ala Met Asp Ala Asn Ser Gln Phe Thr
        115                 120                 125
Ser Thr Tyr Ile Leu Thr Ala Met Ala Ile Asp Arg Tyr Leu Ala Thr
    130                 135                 140
Val His Pro Ile Ser Ser Thr Lys Phe Arg Lys Pro Ser Val Ala Thr
145                 150                 155                 160
Leu Val Ile Cys Leu Leu Trp Ala Leu Ser Phe Ile Ser Ile Thr Pro
                165                 170                 175
Val Trp Leu Tyr Ala Arg Leu Ile Pro Phe Pro Gly Gly Ala Val Gly
            180                 185                 190
Cys Gly Ile Arg Leu Pro Asn Pro Asp Thr Asp Leu Tyr Trp Phe Thr
        195                 200                 205
Leu Tyr Gln Phe Phe Leu Ala Phe Ala Leu Pro Phe Val Val Ile Thr
    210                 215                 220
Ala Ala Tyr Val Arg Ile Leu Gln Arg Met Thr Ser Ser Val Ala Pro
225                 230                 235                 240
Ala Ser Gln Arg Ser Ile Arg Leu Arg Thr Lys Arg Val Thr Arg Thr
                245                 250                 255
Ala Ile Ala Ile Cys Leu Val Phe Phe Val Cys Trp Ala Pro Tyr Tyr
            260                 265                 270
Val Leu Gln Leu Thr Gln Leu Ser Ile Ser Arg Pro Thr Leu Thr Phe
        275                 280                 285
Val Tyr Leu Tyr Asn Ala Ala Ile Ser Leu Gly Tyr Ala Asn Ser Cys
    290                 295                 300
Leu Asn Pro Phe Val Tyr Ile Val Leu Cys Glu Thr Phe Arg Lys Arg
305                 310                 315                 320
Leu Val Leu Ser Val Lys Pro Ala Ala Gln Gly Gln Leu Arg Ala Val
                325                 330                 335
Ser Asn Ala Gln Thr Ala Asp Glu Glu Arg Thr Glu Ser Lys Gly Thr
            340                 345                 350

<210> SEQ ID NO 49
<211> LENGTH: 1080
<212> TYPE: DNA
<213> ORGANISM: Artificial Sequence
<220> FEATURE:
<223> OTHER INFORMATION: Cynomolgus macaque MCH1R/MCH2R IC3 chimera

<400> SEQUENCE: 49
atggacctgg aagcctcgct gctgcccact ggtcccaaca ccagcaacac ctctgatggc      60
cccgataacc tcacctcggc aggatcacct cctcgctcag ggagcgtctc ctacatcaac     120
atcatcatgc cttcggtgtt cggcaccatc tgcctcctgg gcatcatcgg aactccatg     180 gtcatcttcg cggtcgtgaa gaagtccaag ctgcactggt gcaacaatgt ccccgacatc     240
ttcatcatca acctctcggt ggtggatctc ctctttctcc tgggcatgcc cttcatgatc     300
caccagctca tgggcaatgg ggtgtggcac tttgggggaga ccatgtgcac cctcatcacg     360
gccatggatg ccaatagtca gttcaccagc acctacatcc tgaccgccat ggccattgac     420
cgctacctgg ccaccgtcca ccccatctct tccacaaagt tccggaagcc ctctgtggcc     480
accctggtga tctgcctcct gtgggccctc tccttcatca gcatcacccc cgtgtggttg     540
```

```
tatgccagac tcatcccctt cccaggaggt gcagtgggct gcggcatccg cttgcccaac      600
ccggacactg acctttactg gttcaccctg taccagtttt tcctggcctt tgccctgccc      660
ttcgtggtca tcacggccgc atacgtgagg atcctgtgct atacttggga gatgtatcaa      720
cagaataagg atgccagatg ttgcaatccc agcgtaccaa acagagagt gatgaaggtg       780
acccgcacag ccatcgccat ctgcctggtc ttctttgtgt gctgggcacc ctactatgtg      840
ctacagctga cccagttgtc catcagccgc ccgaccctca cctttgtcta cctgtacaat      900
gcggccatca gcttgggcta cgccaacagc tgcctcaacc cctttgtgta cattgtgctc      960
tgcgagacgt tccgcaaacg cttggtcctt tcggtgaagc ctgcagccca ggggcagctt     1020
cgcgctgtca gcaacgctca gacggctgac gaggagagga cagaaagcaa aggtacctga     1080
```

<210> SEQ ID NO 50
<211> LENGTH: 359
<212> TYPE: PRT
<213> ORGANISM: Artificial Sequence
<220> FEATURE:
<223> OTHER INFORMATION: Cynomolgus macaque MCH1R/MCH2R IC3 chimera – amino acid sequence

<400> SEQUENCE: 50

```
Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
            20                  25                  30

Ser Gly Ser Val Ser Tyr Ile Asn Ile Ile Met Pro Ser Val Phe Gly
        35                  40                  45

Thr Ile Cys Leu Leu Gly Ile Ile Gly Asn Ser Met Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Cys Tyr Thr Trp Glu Met Tyr Gln
225                 230                 235                 240

Gln Asn Lys Asp Ala Arg Cys Cys Asn Pro Ser Val Pro Lys Gln Arg
                245                 250                 255

Val Met Lys Val Thr Arg Thr Ala Ile Ala Ile Cys Leu Val Phe Phe
            260                 265                 270
```

Val Cys Trp Ala Pro Tyr Tyr Val Leu Gln Leu Thr Gln Leu Ser Ile
            275                 280                 285

Ser Arg Pro Thr Leu Thr Phe Val Tyr Leu Tyr Asn Ala Ala Ile Ser
            290                 295                 300

Leu Gly Tyr Ala Asn Ser Cys Leu Asn Pro Phe Val Tyr Ile Val Leu
305                 310                 315                 320

Cys Glu Thr Phe Arg Lys Arg Leu Val Leu Ser Val Lys Pro Ala Ala
                325                 330                 335

Gln Gly Gln Leu Arg Ala Val Ser Asn Ala Gln Thr Ala Asp Glu Glu
            340                 345                 350

Arg Thr Glu Ser Lys Gly Thr
            355

<210> SEQ ID NO 51
<211> LENGTH: 1038
<212> TYPE: DNA
<213> ORGANISM: Artificial Sequence
<220> FEATURE:
<223> OTHER INFORMATION: Cynomolgus macaque MCH1R/MCH2R C-terminal
      chimera

<400> SEQUENCE: 51
atggacctgg aagcctcgct gctgcccact ggtcccaaca ccagcaacac ctctgatggc      60
cccgataacc tcacctcggc aggatcacct cctcgctcag ggagcgtctc ctacatcaac     120
atcatcatgc cttcggtgtt cggcaccatc tgcctcctgg catcatcgg gaactccatg     180 gtcatcttcg cggtcgtgaa gaagtccaag ctgcactggt gcaacaatgt ccccgacatc     240
ttcatcatca cctctcggt ggtggatctc ctctttctcc tgggcatgcc cttcatgatc     300
caccagctca tgggcaatgg ggtgtggcac tttggggaga ccatgtgcac cctcatcacg     360
gccatggatg ccaatagtca gttcaccagc acctacatcc tgaccgccat ggccattgac     420
cgctacctgg ccaccgtcca ccccatctct tccacaaagt tccggaagcc ctctgtggcc     480
accctggtga tctgcctcct gtgggccctc tccttcatca gcatcacccc cgtgtggttg     540
tatgccagac tcatcccctt cccaggaggt gcagtgggct gcggcatccg cttgcccaac     600
ccggacactg accttactg gttcaccctg taccagtttt tcctggcctt tgccctgccc     660
ttcgtggtca tcacggccgc atacgtgagg atcctgcagc gcatgacgtc ctcagtggcc     720
cccgcctccc agcgcagcat ccggctgcgg acaaagaggg tgaccgcac agccatcgcc     780 atctgcctgg tcttctttgt gtgctgggca ccctactatg tgctacagct gacccagttg     840
tccatcagcc gcccgaccct caccttgtc tacctgtaca atgcggccat cagcttgggc     900
tacgccaaca gctgcctcaa ccccttgtg tacattgtgc tctgcgagac gttccggaaa     960
cgtctgcctc aaatccaaag gagagtgact gacaaggaaa tcaaaaatat gggaaacact    1020
ctgaaatcac acttttag                                                 1038

<210> SEQ ID NO 52
<211> LENGTH: 345
<212> TYPE: PRT
<213> ORGANISM: Artificial Sequence
<220> FEATURE:
<223> OTHER INFORMATION: Cynomolgus macaque MCH1R/MCH2R C-terminal
      chimera - amino acid sequence

<400> SEQUENCE: 52

Met Asp Leu Glu Ala Ser Leu Leu Pro Thr Gly Pro Asn Thr Ser Asn
1               5                   10                  15

```
Thr Ser Asp Gly Pro Asp Asn Leu Thr Ser Ala Gly Ser Pro Pro Arg
             20                  25                  30
Ser Gly Ser Val Ser Tyr Ile Asn Ile Ile Met Pro Ser Val Phe Gly
         35                  40                  45
Thr Ile Cys Leu Leu Gly Ile Ile Gly Asn Ser Met Val Ile Phe Ala
     50                  55                  60
Val Val Lys Lys Ser Lys Leu His Trp Cys Asn Asn Val Pro Asp Ile
 65                  70                  75                  80
Phe Ile Ile Asn Leu Ser Val Val Asp Leu Leu Phe Leu Leu Gly Met
                 85                  90                  95
Pro Phe Met Ile His Gln Leu Met Gly Asn Gly Val Trp His Phe Gly
             100                 105                 110
Glu Thr Met Cys Thr Leu Ile Thr Ala Met Asp Ala Asn Ser Gln Phe
         115                 120                 125
Thr Ser Thr Tyr Ile Leu Thr Ala Met Ala Ile Asp Arg Tyr Leu Ala
    130                 135                 140
Thr Val His Pro Ile Ser Ser Thr Lys Phe Arg Lys Pro Ser Val Ala
145                 150                 155                 160
Thr Leu Val Ile Cys Leu Leu Trp Ala Leu Ser Phe Ile Ser Ile Thr
                165                 170                 175
Pro Val Trp Leu Tyr Ala Arg Leu Ile Pro Phe Pro Gly Gly Ala Val
            180                 185                 190
Gly Cys Gly Ile Arg Leu Pro Asn Pro Asp Thr Asp Leu Tyr Trp Phe
        195                 200                 205
Thr Leu Tyr Gln Phe Phe Leu Ala Phe Ala Leu Pro Phe Val Val Ile
    210                 215                 220
Thr Ala Ala Tyr Val Arg Ile Leu Gln Arg Met Thr Ser Ser Val Ala
225                 230                 235                 240
Pro Ala Ser Gln Arg Ser Ile Arg Leu Arg Thr Lys Arg Val Thr Arg
                245                 250                 255
Thr Ala Ile Ala Ile Cys Leu Val Phe Phe Val Cys Trp Ala Pro Tyr
            260                 265                 270
Tyr Val Leu Gln Leu Thr Gln Leu Ser Ile Ser Arg Pro Thr Leu Thr
        275                 280                 285
Phe Val Tyr Leu Tyr Asn Ala Ala Ile Ser Leu Gly Tyr Ala Asn Ser
    290                 295                 300
Cys Leu Asn Pro Phe Val Tyr Ile Val Leu Cys Glu Thr Phe Arg Lys
305                 310                 315                 320
Arg Leu Pro Gln Ile Gln Arg Arg Val Thr Asp Lys Glu Ile Lys Asn
                325                 330                 335
Met Gly Asn Thr Leu Lys Ser His Phe
            340                 345

<210> SEQ ID NO 53
<211> LENGTH: 207
<212> TYPE: DNA
<213> ORGANISM: Macaca fascicularis

<400> SEQUENCE: 53
atgtcagtga gagccgcgaa ggagggagta gggagggcag ttgggcttgg aggcggcagc    60
ggctgccagg ctgccaagga agacccctt cccgactgcg gggcttgcgc tcctggacaa   120
ggtggcaggc gctggaggct gccgcagcct gcgtgggtgg aggggagctc agcttggttg   180
tgggagccgg cgaccggcac tggctgg                                       207
```

<210> SEQ ID NO 54
<211> LENGTH: 69
<212> TYPE: PRT
<213> ORGANISM: Macaca fascicularis

<400> SEQUENCE: 54

```
Met Ser Val Arg Ala Ala Lys Glu Gly Val Gly Arg Ala Val Gly Leu
1               5                   10                  15

Gly Gly Gly Ser Gly Cys Gln Ala Ala Lys Glu Asp Pro Leu Pro Asp
                20                  25                  30

Cys Gly Ala Cys Ala Pro Gly Gln Gly Gly Arg Arg Trp Arg Leu Pro
            35                  40                  45

Gln Pro Ala Trp Val Glu Gly Ser Ser Ala Trp Leu Trp Glu Pro Ala
    50                  55                  60

Thr Gly Thr Gly Trp
65
```

<210> SEQ ID NO 55
<211> LENGTH: 1269
<212> TYPE: DNA
<213> ORGANISM: Macaca fascicularis

<400> SEQUENCE: 55

```
atgtcagtga gagccgcgaa ggagggagta gggagggcag ttgggcttgg aggcggcagc      60
ggctgccagg ctgccaagga agaccccctt cccgactgcg ggcttgcgc tcctggacaa      120
ggtggcaggc gctggaggct gccgcagcct gcgtgggtgg aggggagctc agcttggttg     180
tgggagccgg cgaccggcac tggctggatg gacctggaag cctcgctgct gcccactggt     240
cccaacacca gcaacaccct ctgatggcccc gataacctca cctcggcagg atcacctcct    300
cgctcaggga gcgtctccta catcaacatc atcatgcctt cggtgttcgg caccatctgc     360
ctcctgggca tcatcgggaa ctccatggtc atcttcgcgg tcgtgaagaa gtccaagctg     420
cactggtgca acaatgtccc cgacatcttc atcatcaacc tctcggtggt ggatctcctc     480
tttctcctgg gcatgcccttt catgatccac cagctcatgg gcaatggggt gtggcacttt    540
ggggagacca tgtgcacccct catcacggcc atggatgcca atagtcagtt caccagcacc    600
tacatcctga ccgccatggc cattgaccgc tacctggcca ccgtccaccc catctcttcc    660
acaaagttcc ggaagccctc tgtgccacc ctggtgatct gcctcctgtg ggccctctcc    720
ttcatcagca tcacccccgt gtggttgtat gccagactca tccccttccc aggaggtgca    780
gtgggctgcg gcatccgctt gcccaacccg gacactgacc tttactggtt caccctgtac    840
cagtttttcc tggcctttgc cctgccctc gtggtcatca cggccgcata cgtgaggatc    900
ctgcagcgca tgacgtcctc agtggccccc gcctcccagc gcagcatccg gctgcggaca    960
aagagggtga cccgcacagc catcgccatc tgcctggtct ctttgtgtg ctgggcaccc    1020
tactatgtgc tacagctgac ccagttgtcc atcagccgcc cgaccctcac ctttgtctac    1080
ctgtacaatg cggccatcag cttgggctac gccaacagct gcctcaaccc ctttgtgtac    1140
attgtgctct gcgagacgtt ccgcaaacgc ttggtccttt cggtgaagcc tgcagcccag   1200
gggcagcttc gcgctgtcag caacgctcag acggctgacg aggagaggac agaaagcaaa   1260
ggtacctga                                                            1269
```

<210> SEQ ID NO 56
<211> LENGTH: 422

```
<212> TYPE: PRT
<213> ORGANISM: Macaca fascicularis

<400> SEQUENCE: 56

Met Ser Val Arg Ala Ala Lys Glu Gly Val Gly Arg Ala Val Gly Leu
1               5                   10                  15

Gly Gly Gly Ser Gly Cys Gln Ala Ala Lys Glu Asp Pro Leu Pro Asp
            20                  25                  30

Cys Gly Ala Cys Ala Pro Gly Gln Gly Gly Arg Arg Trp Arg Leu Pro
        35                  40                  45

Gln Pro Ala Trp Val Glu Gly Ser Ser Ala Trp Leu Trp Glu Pro Ala
    50                  55                  60

Thr Gly Thr Gly Trp Met Asp Leu Glu Ala Ser Leu Leu Pro Thr Gly
65                  70                  75                  80

Pro Asn Thr Ser Asn Thr Ser Asp Gly Pro Asp Asn Leu Thr Ser Ala
                85                  90                  95

Gly Ser Pro Pro Arg Ser Gly Ser Val Ser Tyr Ile Asn Ile Ile Met
            100                 105                 110

Pro Ser Val Phe Gly Thr Ile Cys Leu Leu Gly Ile Ile Gly Asn Ser
        115                 120                 125

Met Val Ile Phe Ala Val Val Lys Lys Ser Lys Leu His Trp Cys Asn
130                 135                 140

Asn Val Pro Asp Ile Phe Ile Ile Asn Leu Ser Val Val Asp Leu Leu
145                 150                 155                 160

Phe Leu Leu Gly Met Pro Phe Met Ile His Gln Leu Met Gly Asn Gly
                165                 170                 175

Val Trp His Phe Gly Glu Thr Met Cys Thr Leu Ile Thr Ala Met Asp
            180                 185                 190

Ala Asn Ser Gln Phe Thr Ser Thr Tyr Ile Leu Thr Ala Met Ala Ile
        195                 200                 205

Asp Arg Tyr Leu Ala Thr Val His Pro Ile Ser Ser Thr Lys Phe Arg
    210                 215                 220

Lys Pro Ser Val Ala Thr Leu Val Ile Cys Leu Leu Trp Ala Leu Ser
225                 230                 235                 240

Phe Ile Ser Ile Thr Pro Val Trp Leu Tyr Ala Arg Leu Ile Pro Phe
                245                 250                 255

Pro Gly Gly Ala Val Gly Cys Gly Ile Arg Leu Pro Asn Pro Asp Thr
            260                 265                 270

Asp Leu Tyr Trp Phe Thr Leu Tyr Gln Phe Phe Leu Ala Phe Ala Leu
        275                 280                 285

Pro Phe Val Val Ile Thr Ala Ala Tyr Val Arg Ile Leu Gln Arg Met
    290                 295                 300

Thr Ser Ser Val Ala Pro Ala Ser Gln Arg Ser Ile Arg Leu Arg Thr
305                 310                 315                 320

Lys Arg Val Thr Arg Thr Ala Ile Ala Ile Cys Leu Val Phe Phe Val
                325                 330                 335

Cys Trp Ala Pro Tyr Tyr Val Leu Gln Leu Thr Gln Leu Ser Ile Ser
            340                 345                 350

Arg Pro Thr Leu Thr Phe Val Tyr Leu Tyr Asn Ala Ala Ile Ser Leu
        355                 360                 365

Gly Tyr Ala Asn Ser Cys Leu Asn Pro Phe Val Tyr Ile Val Leu Cys
    370                 375                 380

Glu Thr Phe Arg Lys Arg Leu Val Leu Ser Val Lys Pro Ala Ala Gln
385                 390                 395                 400
```

```
-continued

Gly Gln Leu Arg Ala Val Ser Asn Ala Gln Thr Ala Asp Glu Glu Arg
                405                 410                 415

Thr Glu Ser Lys Gly Thr
            420

<210> SEQ ID NO 57
<211> LENGTH: 26
<212> TYPE: DNA
<213> ORGANISM: Artificial Sequence
<220> FEATURE:
<223> OTHER INFORMATION: MCH1R outer reverse primer

<400> SEQUENCE: 57
cacaggaggc agatcaccag ggtggc                                    26

<210> SEQ ID NO 58
<211> LENGTH: 22
<212> TYPE: DNA
<213> ORGANISM: Artificial Sequence
<220> FEATURE:
<223> OTHER INFORMATION: MCH1R inner reverse primer

<400> SEQUENCE: 58
ggtgctggtg aactgactat tg                                        22
```

MELANIN CONCENTRATING HORMONE RECEPTORS

CROSS-REFERENCE TO RELATED APPLICATIONS

This application claims priority to U.S. Provisional Application No. 60/284,835, filed Apr. 19, 2001.

FIELD OF THE INVENTION

The present invention relates generally to tools useful for the discovery of drugs for the treatment of conditions associated with melanin concentrating hormone (MCH) receptor activation in humans and other animals. The invention is more specifically related to polypeptides comprising monkey MCH type 1 receptor (MCH1R) sequences, including monkey MCH1R and chimeric MCH receptors, and to polynucleotides encoding such polypeptides. Such polypeptides and polynucleotides may be used in the identification of agents that modulate MCH receptor activity.

BACKGROUND OF THE INVENTION

Melanin concentrating hormone, or MCH, is a cyclic 19 amino acid neuropeptide that functions as a regulator of food intake and energy balance. MCH is produced in the hypothalamus of many vertebrate species including man. MCH is also produced at various peripheral sites, including the gastrointestinal tract and testis.

The postulated role of MCH in feeding behavior and body weight has been confirmed by the finding that I.C.V. injection of MCH into the lateral ventrical of the hypothalamus increases caloric consumption in rats over similarly treated control animals. Furthermore, rats having the ob/ob genotype exhibit a 50–80% increase in MCH mRNA expression as compared to leaner ob/+ genotype mice. MCH knockout mice are leaner than their MCH-producing siblings due to hypophagia and an increased metabolic rate.

MCH activity is mediated via binding to specific cell surface receptors. Like other G protein-coupled receptors (e.g., neuropeptide Y (NPY) and beta-adrenergic receptors), MCH receptors are membrane-spanning proteins that consist of a single contiguous amino acid chain comprising an extracellular N-terminal domain, seven membrane-spanning alpha helical domains (connected by three intracellular loop domains alternating with three extracellular loop domains), and an intracellular C-terminal domain. Signal transduction is initiated by the binding of MCH to the receptor. This binding is believed to elicit conformational changes in the extracellular domains. When the receptor is functioning properly, these conformational changes are believed to propagate through the transmembrane domains and result in a coordinated change in the intracellular portions of the receptor. This precise alteration in the intracellular domains is believed to trigger the associated G-protein complex to modulate intracellular signaling.

The human MCH type 1 receptor (MCH1R) is a 353 amino acid G protein-coupled receptor, first reported by Lakaye, et al. (BBA (1998) 1401:216–220), and described in U.S. Pat. No. 6,291,195. MCH1R has also been known as SLC-1 (somatostatin-like receptor; see U.S. Pat. No. 6,008, 012). Immunohistochemistry studies of rat brain sections indicate that the MCH1R receptor is widely expressed in the brain. MCH1R receptor expression has been found in the olfactory tubercle, cerebral cortex, substantia nigra, basal forebrain CA1, CA2, and CA3 field of the hippocampus, amygdala, and in nuclei in the hypothalamus, thalamus, midbrain and hindbrain. Strong signals have been observed in the ventromedial and dorsomedial nuclei of the hypothalamus, two areas of the brain known to be involved in feeding behavior. Upon binding MCH, MCH1R expressed in HEK 293 cell mediates a dose dependent release of intracellular calcium. Cells expressing MCH receptors have also been shown to exhibit a pertussis toxin sensitive dose-dependent inhibition of forskolin-elevated cyclic AMP, suggesting that the receptor couples to a $G_{i/o}$ G-protein alpha subunit.

Because MCH is an important regulator of food intake and energy balance, agents capable of modulating MCH receptor activity are highly desirable for the treatment of obesity, eating disorders (e.g., bulimia and anorexia), sexual disorders (e.g., anorgasmic or psychogenic impotence) and metabolic disorders, such as diabetes. Isolated MCH receptors (e.g., as components of membrane preparations), cells expressing such receptors and cloned MCH receptor genes are needed to facilitate the discovery of such agents.

Accordingly, there is a need in the art for the identification of additional MCH receptor sequences. The present invention fulfills this need, and provides further related advantages.

BRIEF DESCRIPTION OF THE DRAWINGS

FIGS. 1A and 1B depict an alignment of the amino acid sequences of (a) cynomolgus macaque MCH1R long form (SEQ ID NO:56); (b) Cynomolgus macaque MCH1R (SEQ ID NO:2), (c) the human somatostatin-like protein recited in SEQ ID NO:2 of U.S. Pat. No. 6,008,012, (d) human MCH1R and (e) rat MCH1R.

FIG. 2A and 2B depict an alignment of the amino acid sequences of (a) Cynomolgus macaque MCH1R (SEQ ID NO:2), (b) Cynomolgus macaque MCH1R long form (SEQ ID NO:56); and (c) the human MCH1 recited as SEQ ID NO:2 of U.S. Pat. No. 6,291,195 (encoded by GenBank accession number AR169785).

DESCRIPTION OF THE SEQUENCE LISTING

SEQ ID NO:1 Cynomolgus macaque MCH1R DNA sequence
SEQ ID NO:2 Cynomolgus macaque MCH1R amino acid sequence
SEQ ID NO:3 Amino acid sequence of the $His_{6x}$ epitope
SEQ ID NO:4 Amino acid sequence of the FLAG epitope
SEQ ID NO:5 Human MCH1R DNA sequence
SEQ ID NO:6 Human MCH1R amino acid sequence
SEQ ID NO:7 5' Cynomolgus macaque MCH1R primer
SEQ ID NO:8 3' Cynomolgus macaque MCH1R primer
SEQ ID NO:9 Human NPY1 receptor DNA CDS only
SEQ ID NO:10 Human NPY1 receptor amino acid sequence
SEQ ID NO:11 Human NPY1 receptor BspE forward primer for CT
SEQ ID NO:12 Human NPY1 receptor reverse primer for CT
SEQ ID NO:13 Human NPY1 receptor BspE—Not I fragment for CT
SEQ ID NO:14 Human NPY1 receptor IC3 Sense oligo
SEQ ID NO:15 Human NPY1 receptor IC3 Antisense oligo
SEQ ID NO:16 Human MCH1R plus BspE Site added for C-terminal chimeras
SEQ ID NO:17 Human MCH1R/NPY1 IC3 chimera—DNA CDS only SEQ ID NO:18 Human MCH1R/NPY1 IC3 chimera—amino acid sequence
SEQ ID NO:19 Human MCH1R/NPY1 C-terminal chimera—DNA CDS only
SEQ ID NO:20 Human MCH1R/NPY1 C-terminal chimera—amino acid sequence
SEQ ID NO:21 Human MCH1R/NPY1 IC3 chimera in pcDNA3.1Plus (pN105)
SEQ ID NO:22 Human MCH1R/NPY1 C-terminal chimera in pcDNA3.1Plus (pN107)
SEQ ID NO:23 Human beta-2 adrenergic receptor—DNA
SEQ ID NO:24 Human beta-2 adrenergic receptor amino acid sequence
SEQ ID NO:25 Human beta-2 adrenergic receptor C-terminal forward primer
SEQ ID NO:26 Human beta-2 adrenergic receptor C-terminal reverse primer
SEQ ID NO:27 Human MCH1R/beta-2 adrenergic receptor C-term. chimera—DNA CDS
SEQ ID NO:28 Human MCH1R/beta-2 adrenergic receptor C-term. chimera—aa sequence
SEQ ID NO:29 Human MCH1R/beta-2 adrenergic receptor C-term. chimera in pcDNA3.1Plus (pN125)
SEQ ID NO:30 Amino acid residues 30–60 of SEQ ID NO:2
SEQ ID NO:31 Human MCH1R forward primer
SEQ ID NO:32 Human MCH1R reverse primer
SEQ ID NO:33 Cynomolgus macaque MCH2R clone A DNA sequence
SEQ ID NO:34 Cynomolgus macaque MCH2R clone A amino acid sequence
SEQ ID NO:35 Cynomolgus macaque MCH2R clone B DNA sequence
SEQ ID NO:36 Cynomolgus macaque MCH2R clone B amino acid sequence
SEQ ID NO:37 Cynomolgus macaque MCH2R DNA sequence
SEQ ID NO:38 Canine MCH2R DNA sequence
SEQ ID NO:39 Canine MCH2R amino acid sequence
SEQ ID NO:40 Cynomolgus macaque MCH1R with BspE Site for C-term. chimeras
SEQ ID NO:41 Cynomolgus macaque MCH1R/human NPY1 IC3 chimera—DNA seq.
SEQ ID NO:42 Cynomolgus macaque MCH1R/human NPY1 IC3 chimera—aa sequence
SEQ ID NO:43 Cynomolgus macaque MCH1R/human NPY1 C-term. chimera—DNA
SEQ ID NO:44 Cynomolgus macaque MCH1R/human NPY1 C-term. chimera—aa seq.
SEQ ID NO:45 Cynomolgus macaque MCH1R/human beta-2 adrenergic receptor C-terminal chimera—DNA sequence
SEQ ID NO:46 Cynomolgus macaque MCH1R/human beta-2 adrenergic receptor C-terminal chimera—amino acid sequence
SEQ ID NO:47 Cynomolgus macaque MCH1R/MCH2R N-terminal chimera—DNA
SEQ ID NO:48 Cynomolgus macaque MCH1R/MCH2R N-terminal chimera—aa
SEQ ID NO:49 Cynomolgus macaque MCH1R/MCH2R IC3 chimera—DNA sequence
SEQ ID NO:50 Cynomolgus macaque MCH1R/MCH2R IC3 chimera—amino acid seq.
SEQ ID NO:51 Cynomolgus macaque MCH1R/MCH2R C-terminal chimera—DNA
SEQ ID NO:52 Cynomolgus macaque MCH1R/MCH2R C-terminal chimera—aa
SEQ ID NO:53 Cynomolgus macaque MCH1R 5' extension—DNA sequence
SEQ ID NO:54 Cynomolgus macaque MCH1R 5' extension—amino acid sequence
SEQ ID NO:55 Cynomolgus macaque MCH1R long form 5'—DNA sequence
SEQ ID NO:56 Cynomolgus macaque MCH1R long form 5'—amino acid sequence
SEQ ID NO:57 MCH1R outer reverse primer
SEQ ID NO:58 MCH1R inner reverse primer

SUMMARY OF THE INVENTION

Briefly stated, the present invention provides polypeptides, polynucleotides and methods for using such polypeptides and polynucleotides to identify therapeutic agents for treating conditions associated with MCH receptor activation. In one aspect, the present invention provides isolated MCH1R polypeptides that comprise a monkey MCH1R sequence. Within certain embodiments, such polypeptides comprise at least 30 consecutive amino acids of the cynomolgus macaque (*Macaca fascicularis*) MCH1R sequence provided in SEQ ID NO:56; preferably, the 30 consecutive amino acids are located within residues 1–130 of SEQ ID NO:56. Preferably, such polypeptides exhibit MCH1R ligand binding activity. Certain polypeptides comprise at least amino acids 30–60 of the cynomolgus macaque sequence provided in SEQ ID NO:2.

Within related aspects, the present invention provides MCH1R chimeric polypeptides that comprise a MCH1R sequence, wherein one or more domains are replaced with a corresponding domain of a different G protein-coupled receptor. Preferably, from 1 to 3 domains are replaced; more preferably 1 domain is replaced. For example, the intracellular loop 3, N-terminal domain or C-terminal domain of MCH1R may be replaced with a corresponding domain of MCH2R, NPY$_1$ receptor, beta-2-adrenergic receptor or MCH1R from another species. Representative chimeric polypeptides include those provided in SEQ ID NOs:18, 20, 28, 42, 44, 46, 48, 50 and 52.

Within further aspects, the present invention provides isolated polynucleotides (e.g., DNA or RNA) that encode a MCH1R polypeptide or chimeric polypeptide as described above. Such polynucleotides may comprise a native sequence (e.g., SEQ ID NO:1 or 55) or may contain changes relative to the native sequence that do not affect the sequence of the encoded polypeptide. Certain such polynucleotides comprise at least 90 consecutive nucleotides of SEQ ID NO:55.

The present invention further provides, within related aspects, expression vectors (e.g., plasmids and viral vectors) that comprise a polynucleotide as described above, as well as transgenic host cells (i.e., cells comprising at least one heterologous expression vector) that express a polypeptide as described above (e.g., as a result of being transformed or transfected with at least one such expression vector) and cell membrane preparations isolated from such transgenic cells.

Methods are further provided, within other aspects, for determining MCH receptor binding activity of a compound, comprising the steps of: (a) contacting a compound with at least one transgenic cell or with a cell membrane preparation as described above; and (b) detecting binding of the compound to the cell(s) or cell membrane preparation. Binding may be detected, for example, by measuring competition for binding with detectably labeled MCH.

Within further aspects, the present invention provides methods for detecting MCH receptor modulating activity of a compound, comprising the steps of: (a) contacting a compound with at least one transgenic cell as described above; (b) detecting a cellular property (e.g., a level of $Ca^{2+}$ in the contacted cell(s)); and (c) comparing the detected cellular property with a property detected in control cells in the absence of compound (e.g., comparing a detected level of $Ca^{2+}$ with a level of $Ca^{2+}$ detected in control cells in the absence of compound). Within certain embodiments, before step (a), the transgenic cells are: (i) contacted with an indicator of intracellular $Ca^{2+}$ concentration to yield indicator-loaded cells; and (ii) washed. The level of $Ca^{2+}$ may be detected, for example, by quantifying $Ca^{2+}$-concentration-dependant changes in the properties of the indicator of intracellular $Ca^{2+}$.

Methods are further provided, within other aspects, for detecting MCH receptor agonist activity of a compound, comprising the steps of: (a) contacting transgenic cells as described above with an indicator of intracellular $Ca^{2+}$ concentration, to yield indicator-loaded cells; (b) washing the indicator-loaded cells; (c) contacting a portion of the washed, indicator-loaded cells with a compound to yield test cells; (d) separately detecting a property of the indicator of intracellular $Ca^{2+}$ concentration in the test cells and in a second portion of the washed and indicator-loaded cells; and (e) comparing the detected property of the test cells with the detected property of the washed indicator-loaded cells.

The present invention further provides methods for detecting MCH receptor antagonist activity of a compound, comprising the steps of: (a) contacting a compound and an MCH receptor agonist with transgenic cells as described above; (b) detecting a level of $Ca^{2+}0$ in the contacted cells; and (c) comparing the detected level of $Ca^{2+}$ with a level of $Ca^{2+}$ detected in control cells in the presence of agonist and in the absence of compound.

Methods are further provided for detecting MCH receptor antagonist activity of a compound, comprising the steps of: (a) contacting transgenic cells as described above with an indicator of intracellular $Ca^{2+}$ concentration, to yield indicator-loaded cells; (b) washing the indicator-loaded cells; (c) contacting a first portion of the washed, indicator-loaded cells with a compound and an MCH receptor agonist to yield test cells; (d) contacting a second portion of the washed, indicator-loaded cells with an MCH receptor agonist to yield control cells; (e) separately detecting a property of the indicator of intracellular $Ca^{2+}$ in the test cells and in the control cells; and (f) comparing the detected property of the test cells with the detected property of the control cells.

These and other aspects of the present invention will become apparent upon reference to the following detailed description and attached drawing.

DETAILED DESCRIPTION OF THE INVENTION

As noted above, the present invention is generally directed to compounds and methods for identifying therapeutic agents that may be used to treat conditions associated with MCH receptor activation. Compounds provided herein include polypeptides that comprise a monkey MCH1R sequence, as well as polynucleotides that encode such polypeptides. Chimeric polypeptides comprising a MCH1R sequence in which one or more domains are replaced with a corresponding domain of another G protein-coupled receptor are also provided. MCH1R polypeptides and polynucleotides may be used to identify therapeutic agents, as discussed in further detail below.

MCH Receptor Polynucleotides

Any polynucleotide that encodes an MCH1R polypeptide or chimera as described herein is encompassed by the present invention. Polynucleotides may be single-stranded (coding or antisense) or double-stranded, and may be DNA (e.g., genomic, cDNA or synthetic) or RNA, such as mRNA molecules. Modified analogues of such polynucleotides are also encompassed (e.g., phosphorthioate derivatives). Additional coding or non-coding sequences may, but need not, be present within a polynucleotide of the present invention, and a polynucleotide may, but need not, be linked to other molecules and/or support materials.

Certain polynucleotides encode a cynomolgus macaque MCH1R polypeptide. Such polynucleotides generally encode at least 30 consecutive amino acid residues of the MCH1R sequence provided in SEQ ID NO:56. Preferably, at least 30 consecutive amino acids located between residues 1 and 130 are encoded by such polynucleotides, and the encoded polypeptide exhibits MCH1R ligand binding activity (i.e., detectably bind MCH within the assay provided in Example 4). Certain polynucleotides encode at least amino acid residues 30–60 (SEQ ID NO:30) of a cynomolgus macaque MCH1R protein sequence provided in SEQ ID NO:2. For less than full length MCH1R sequences, deletions at the 3' end are generally preferred. Preferred cynomolgus macaque MCH1R polynucleotides encode at least amino acid residues 2–64 of SEQ ID NO:2, more preferably at least amino acid residues 2 to 230 of SEQ ID NO:2 and still more preferably at least amino acid residues 2 to 353 of SEQ ID NO:2. Certain such polynucleotides comprise at least 90 consecutive nucleotides, preferably at least nucleotides 28–220, of a cynomolgus macaque MCH1R sequence provided herein (SEQ ID NO:1).

Cynomolgus macaque MCH1R polynucleotides may, but need not, further encode the 5' sequence provided in SEQ ID NO:54 (by comprising, for example, the 5' sequence recited in SEQ ID NO:53). The 5' sequence is also shown as residues 1 to 69 of SEQ ID NO:56 (encoded by nucleotides 1 to 207 of SEQ ID NO:55). Polynucleotides with this 5' sequence are referred to herein as MCH1R long form polynucleotides.

The present invention also provides polynucleotides that encode chimeric MCH1R polypeptides. Such chimeric polypeptides generally comprise a MCH1R sequence (e.g., monkey, as described herein, or human, as in SEQ ID NO:6) in which one or more domains have been replaced with a corresponding domain of a different G-coupled protein receptor (e.g., MCH1R from a different species; a different MCH receptor such as MCH2R; NPY1 receptor; or beta-2-adrenergic receptor). Certain such chimeric polypeptides are MCH1R intracellular loop 3 chimeras (i.e., MCH1R sequences in which the amino acid sequence of the third intracellular loop has been replaced by the amino acid sequence of the third intracellular loop of another G protein-coupled receptor), C-terminal chimeras or N-terminal chimeras. As noted above, polynucleotides encoding such chimeras may comprise naturally occurring and/or non-naturally occurring sequences.

Naturally-occurring sequences that may be used to construct chimeric polynucleotides are provided herein and in the literature (e.g., SEQ ID NO:9 and GenBank Accession Number M88461 for human NPY1 receptor sequence; SEQ ID NO:23 and Accession Number Y00106 for human beta-2 adrenergic receptor; SEQ ID NO:33, 35 or 37 for macaque MCH2R; SEQ ID NO:38 for canine MCH2R). A precise coding sequence suitable for the construction of a chimera is readily determined by those of ordinary skill in the art from the nucleotide and amino acid sequences provided herein, and may be constructed using standard recombinant techniques.

Polynucleotides complementary to the MCH1R sequences discussed above (or portions thereof) are also encompassed by the present invention. Such polynucleotides include, for example, PCR products and restriction fragments, and may find use as probes or primers. Probes may be labeled with a variety of reporter groups, such as radionuclides and enzymes. Complementary polynucleotides generally hybridize to a MCH1R polynucleotide under stringent conditions. Stringent conditions include, for example, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C.). For short oligonucleotide probes, washing may be performed in 6×SSC/ 0.05% sodium pyrophosphate at 37° C. (for 14-base oligos), 48° C. (for 17-base oligos), 55° C. (for 20-base oligos), and 60° C. (for 23-base oligos). Other stringent conditions include overnight hybridization at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 μg/mL denatured, sheared salmon sperm DNA, followed by washing the filters in 0×SSC at about 65° C.

It will be appreciated by those of ordinary skill in the art that, as a result of the degeneracy of the genetic code, there are many nucleotide sequences that encode the polypeptides provided herein. Some of these polynucleotides bear minimal homology to the nucleotide sequence of any naturally occurring gene. Nonetheless, polynucleotides that vary due to differences in codon usage are specifically contemplated by the present invention. Additionally, it will be apparent that sequence changes may be made in the non-coding regions of the polynucleotides without altering the amino acid sequence of the protein product.

The present invention also encompasses polynucleotides that encode amino acid sequences with up to 15 (preferably no more than 10, more preferably no more than 5) amino acid substitutions relative to a naturally occurring monkey MCH1R sequence, provided that any substitutions do not substantially diminish receptor function (e.g., determined using a calcium mobilization assay as described within Example 5 herein) and are non-human (i.e., do not result in a human MCH1R sequence (SEQ ID NO:6)). In general, as discussed below, conservative substitutions are preferred. MCH1R polynucleotides preferably encode a polypeptide that does not comprise one or more of the following residues: (1) Ala in the position corresponding to position 14 of SEQ ID NO:2; (2) Thr in the position corresponding to position 33 of SEQ ID NO:2; (3) Ile in the position corresponding to position 36 of SEQ ID NO:2; and/or (4) Thr in the position corresponding to position 60 of SEQ ID NO:2. More preferably, an MCH1R polynucleotide encodes a polypeptide having at least one, preferably at least three or four, of the following residues (or conservative substitutions thereof): (1) Thr in the position corresponding to position 14 of SEQ ID NO:2; (2) Ser in the position corresponding to position 33 of SEQ ID NO:2; (3) Val in the position corresponding to position 36 of SEQ ID NO:2; and/or (4) Met in the position corresponding to position 60 of SEQ ID NO:2. The phrase "in the position corresponding to," as used herein, refers to the position within the polypeptide that, when aligned with SEQ ID NO:2 (using, for example, a ClustalW alignment) is matched with the specified residue of SEQ ID NO:2.

Polynucleotides provided herein may further comprise additional sequences. For example, an optimized translation initiation sequence (Kozak sequence) may be added to the 5' terminus. In-frame additions of sequences encoding antibody recognition sites may also, or alternatively, be included. Such sites are well known in the art, and include, but are not limited to the His-6×(hexa-histidine) epitope (SEQ ID NO:3) which is specifically bound by the Monoclonal Anti-polyhistidine Clone HIS-1 monoclonal antibody (Sigma, St. Louis No. H1029), and the FLAG epitope (SEQ ID NO:4) which is specifically bound by the FLAG-M2 monoclonal antibody (Sigma, St. Louis No. F3165). Techniques for making such modifications are also well known in the art, and may be readily carried out using routine methods or by using prepared kits, such as the Sigma Mammalian FLAG Expression Kits (Sigma, St. Louis; e.g., Nos. FL-MA and FL-MC). Preferably, fusions are made as in-frame amino-(N-) or carboxy-(C-) terminal fusions. When properly membrane-inserted fusion proteins (e.g., proteins retaining receptor signal transduction function) are desired, C-terminal fusions are preferred as being less prone to interfere with membrane insertion of the fusion protein.

Polynucleotides are preferably "isolated" (i.e., represent at least 10% of total nucleic acid molecules, preferably at least 20% and more preferably at least 50% of total nucleic acid molecules, within a sample or preparation). Unless otherwise specified, a polynucleotide comprising a given sequence may be of any length.

Polynucleotides may be prepared using any of a variety of well known techniques. For example, polynucleotides (or portions thereof) may be amplified via polymerase chain reaction (PCR), using sequence-specific primers designed based on the sequences provided herein, which may be purchased or synthesized. Portions of a desired polynucleotide obtained using PCR may be assembled into a single contiguous sequence by ligating suitable fragments, using well known techniques. Alternatively, amplified portion may be used to isolate a full length gene from a suitable library (e.g., one or more brain regions such as hypothalamus) using well known hybridization techniques. Within such techniques, a library (cDNA or genomic) is screened using one or more polynucleotide probes or primers corresponding to a portion of the desired sequence. Preferably, a library is size-selected for larger molecules. Random primed libraries may also be preferred for obtaining 5' regions of genes.

It will be apparent that primers designed based on the sequences provided herein may be used to obtain polynucleotides encoding MCH1R from other species, and that such polynucleotides are within the scope of the present invention.

RNA molecules may be generated by in vitro or in vivo transcription of DNA sequences encoding an MCH1R polypeptide, provided that the DNA is incorporated into a vector with a suitable RNA polymerase promoter (such as T7 or SP6). For example, antisense RNA may be generated from suitable cDNA constructs that have been introduced into cells or tissues to facilitate the production of antisense RNA.

Polynucleotides containing nucleotide substitutions, additions and deletions may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

MCH Receptor Polypeptides

The term "MCH1R polypeptide," as used herein, refers to monkey MCH1R polypeptides (i.e., polypeptides comprising a naturally-occurring monkey MCH1R sequence or variant thereof containing amino acid insertions, deletions and/or substitutions as described herein), as well as MCH1R chimeric polypeptides comprising an MCH1R sequence from any species in which one or more domains are replaced with corresponding domain(s) from a different G-coupled protein receptor. Cynomolgus macaque MCH1R polypeptides provided herein generally comprise at least 30 consecutive amino acid residues of SEQ ID NO:56, preferably at least 30 consecutive amino acids present between amino acids 1 and 130 of SEQ ID NO:56. Preferred MCH1R polypeptides comprise at least amino acid residues 30–60 (SEQ ID NO:30), 2–64 or 2 to 230 of SEQ ID NO:2. Certain such polypeptides comprise at least amino acid residues 2 to 353 of SEQ ID NO:2. MCH1R long form polypeptides may further comprise the N-terminal sequence shown in SEQ ID NO:54 (and as amino acids 1–69 of SEQ ID NO:56, which provides the full long form MCH1R sequence). Unless otherwise specified, a polypeptide comprising a given sequence may be of any length.

MCH1R polypeptides are preferably isolated. A polypeptide is said to be "isolated" if it represents at least 1% of total polypeptide molecules, preferably at least 10% and more preferably at least 20% of total polypeptide molecules, within a sample or preparation).

Certain MCH1R polypeptides and chimeric polypeptides exhibit MCH binding activity and/or receptor function. In other words, such polypeptides detectably bind MCH within a MCH1R ligand binding assay (i.e., within the assay provided in Example 4) and/or display detectable activity within a calcium mobilization assay as provided in Example 5. References herein to "MCH1R ligand binding activity" refer to binding detected within the assay described in Example 4.

As noted above, amino acid substitutions may be made within cynomolgus macaque MCH1R sequences at up to 15 amino acid residues, preferably at no more than 10 residues and more preferably at no more than 5 residues. Any substitutions should not substantially diminish MCH1R ligand binding activity and/or MCH receptor function. A substitution does not "substantially diminish" binding activity or receptor function if the activity within a ligand binding assay or calcium mobilization assay is enhanced, unchanged or diminished by no more than 10%, relative to the native MCH1R sequence of SEQ ID NO:2. In addition, substitutions should not result in a human MCH1R sequence (SEQ ID NO:6). Preferably, MCH1R polypeptides retain at least one, preferably all four, of the following amino acid residues: (1) Thr in the position corresponding to position 14 of SEQ ID NO:2; (2) Ser in the position corresponding to position 33 of SEQ ID NO:2; (3) Val in the position corresponding to position 36 of SEQ ID NO:2; and/or (4) Met in the position corresponding to position 60 of SEQ ID NO:2.

In general, conservative substitutions are preferred. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lys and arg; and amino acids with uncharged polar head groups having similar hydrophilicity values include leu, ile and val; gly and ala; asn and gln; and ser, thr, phe and tyr. Other groups of amino acids that may represent conservative changes include: (1) glu, asp, gin, asn, ser, thr; (2) cys, ser, tyr, thr; (3) gly, pro, val, ile, leu, met, ala, phe; (4) lys, arg, his; and (5) phe, tyr, trp, his.

Chimeric MCH1R polypeptides are those in which at least one domain is derived from a MCH1R sequence (e.g., monkey, human or rat), with one or more domains replaced with corresponding domain(s) from a different G-coupled protein receptor. As noted above, MCH receptors contain an N terminal domain, seven transmembrane domains interspersed with three intracellular loop domains alternating with three extracellular loop domains, and an intracellular C-terminal domain. The precise locations of domains may be conveniently calculated by computer analysis of hydrophobicity or hydrophilicity using hydropathy profiles, such as standard Kyte-Doolittle analysis (Kyte and Doolittle, *J. Mol. Biol.* 157:105–32, 1982). The transition boundaries between the hydrophobic and hydrophilic domains are typically marked by the presence of charged or polar (hydrophilic) amino acid residues at the beginning or end of a stretch of nonpolar (hydrophobic) residues. The N-terminus extends into the extracellular space and the C-terminus into the cytoplasm of the cell. Each of the seven hydrophobic domains is about 20–25 amino acids long, assumes a largely alpha helical conformation, and crosses once through the plasma membrane, its entire extent generally embedded in the membrane. The hydrophobic domains are thus also referred to as transmembrane domains or membrane-spanning alpha helical domains, while the hydrophilic domains are referred to as either extracellular or intracellular domains, depending upon their predicted locations in a functional, membrane-bound receptor. The hydrophilic domains interconnecting transmembrane domains form loops within the cytoplasm or extracellular space, and are consequently referred to as cytoplasmic or extracellular loop domains.

G protein-coupled receptors, including MCH receptors, have been structurally modeled as to secondary and tertiary structural conformation, and the precise locations of the extracellular, transmembrane and intracellular domains within their primary structures (i.e., their amino acid sequences) are well known and generally agreed to in the art. The location of domains within a G protein-coupled receptor may be determined using the model of Baldwin (*EMBO J.* 12:1693–703, 1993), in which certain conserved residues are initially located and aligned. For constructing chimeric polypeptides provided herein, locations of domains within the MCH1R polypeptide of SEQ ID NO:2 are generally as follows: extracellular N-terminal (residues 1 to 40), seven transmembrane domains (approximately residues 41–66, 76–101, 117–142, 158–183, 207–232, 254–279 and 291–316, respectively) interspersed with three intracellular loop domains alternating with three extracellular loop domains, and an intracellular C-terminal domain (residues 317 to end). Intracellular loop 3 consists of residues 233–253. Any of these domains may be replaced with a corresponding domain from MCH1R of a different species, MCH2R, or a non-MCH receptor such as $NPY_1$ or beta-2 adrenergic receptor. It will be apparent that, when replacing one domain with another, the residue numbers provided above may be altered slightly in either direction in order to facilitate cloning. In general, residue numbers may be altered by up to 6, preferably up to 4, amino acid residues in either direction. For example, if intracellular loop 3 (IC3) is to be replaced, the replaced portion may begin at any residue between 227 and 239, and may end at any residue between 247 and 259. Preferred macaque MCH1R IC3 chimeras contain residues 1–232 and 254–353 of MCH1R, with residues corresponding to MCH1R 233–253 derived from a different G-coupled protein receptor. Similarly, the C-terminal domain may be replaced beginning at any residue between 311 and 323, preferably beginning at residue 319–320. Corresponding domains of other G-coupled protein receptors may be readily identified, as noted above, by performing an alignment of the receptor sequence with an MCH1R sequence provided herein. By way of example, the N-terminal domain, intracellular loop 3 and the C-terminal domain of macaque MCH2R may be amino acids 1–35, 222–248 and 312–340, respectively, of SEQ ID NO:34 or 36; intracellular loop 3 and the C-terminal domain of human $NPY_1$ may be amino acids 236–260 and 329–384, respectively, of SEQ ID NO:10; and the C-terminal domain of human beta-2 adrenergic receptor may be amino acids 344–413 of SEQ ID NO:24.

Preferred chimeric polypeptides are those in which IC3, the C-terminal domain or the N-terminal domain is replaced. The sequences of certain representative chimeras are summarized in Table I and recited in SEQ ID NOs:18, 20, 28, 42, 44, 46, 48, 50 and 52. More specifically, SEQ ID NO:18 is a human MCH1R/human $NPY_1$ receptor IC3 chimera in which the amino acid sequence of the third intracellular loop of the MCH receptor is replaced by the amino acid sequence of the third intracellular loop of the human $NPY_1$ receptor (polynucleotide sequence provided in SEQ ID NO:17); SEQ ID NO:20 is a human MCH1R/human $NPY_1$ receptor C-terminal chimera in which the C-terminal domain of the MCH receptor is replaced by the C-terminal domain of the human $NPY_1$ receptor (polynucleotide sequence provided in SEQ ID NO:19); SEQ ID NO:28 is a human MCH1R/human beta-2 adrenergic receptor C-terminal chimera in which the C-terminal domain of the MCH receptor is replaced by the C-terminal domain of the human beta-2 adrenergic receptor (polynucleotide sequence provided in SEQ ID NO:27); SEQ ID NO:42 is a cynomolgus macaque MCH1R/human $NPY_1$ receptor IC3 chimera (polynucleotide sequence provided in SEQ ID NO:41); SEQ ID NO:44 is a cynomolgus macaque MCH1R/human $NPY_1$ C-terminal chimera (polynucleotide sequence provided in SEQ ID NO:43); SEQ ID NO:46 is a cynomolgus macaque MCH1R/human beta-2 adrenergic receptor C-terminal chimera (polynucleotide sequence provided in SEQ ID NO:45); SEQ ID NO:48 is a cynomolgus macaque MCH1R/cynomolgus macaque MCH2R N-terminal chimera, in which the N-terminal amino acid sequence of MCH1R is replaced by the N-terminal amino acid sequence of MCH2R (polynucleotide sequence provided in SEQ ID NO:47); SEQ ID NO:50 is a cynomolgus macaque MCH1R/cynomolgus macaque MCH2R IC3 chimera (polynucleotide sequence provided in SEQ ID NO:49); and SEQ ID NO:52 is a cynomolgus macaque MCH1R/cynomolgus macaque MCH2R C-terminal chimera (polynucleotide sequence provided in SEQ ID NO:51). It will be apparent that similar chimeras may be generated using the MCH1R long form shown in SEQ ID NO:56). As noted above, sequences that may be used to construct such chimeras are provided herein, and in the literature. Additional precise coding sequences suitable for the construction of a chimera may be readily determined by those of ordinary skill in the art from the amino acid sequences provided herein, and may be constructed using standard recombinant techniques.

TABLE I

Representative MCH1R Chimeras

| SEQ ID | MCH1R Residues | Inserted Domain |
|---|---|---|
| 18 | 1–232, 251–353 of SEQ ID NO:6 | Human NPY1 IC3 (aa 236–260 of SEQ ID NO:10) |
| 20 | 1–319 of SEQ ID NO:6 | Human NPY1 C-terminal (aa 329–384 of SEQ ID NO:10) |
| 28 | 1–319 of SEQ ID NO:6 | Human beta-2 adrenergic receptor C-terminal (aa 344–413 of SEQ ID NO:24) |
| 42 | 1–232, 254–353 of SEQ ID NO:2 | Human NPY1 1C3 (aa 236–260 of SEQ ID NO:10) |
| 44 | 1–319 of SEQ ID NO:2 | Human NPY1 C-terminal (aa 329–384 of SEQ ID NO:10) |
| 46 | 1–318 of SEQ ID NO:2 | Human beta-2 adrenergic receptor C-terminal (aa 344–413 of SEQ ID NO:24) |
| 48 | 36–353 of SEQ ID NO:2 | Macaque MCH2R N-terminal (aa 1–35 of SEQ ID NO:34 or 36) |
| 50 | 1–232, 254–353 of SEQ ID NO:2 | Macaque MCH2R 1C3 (aa 222–248 of SEQ ID NO:34 or 36) |
| 52 | 1–319 of SEQ ID NO:2 | Macaque MCH2R C-terminal (aa 315–340 of SEQ ID NO: 34 or 36) |

Polypeptides may be prepared using any of a variety of well known techniques from transgenic cells (i.e., cells that have been genetically altered to express a MCH1R polypeptide). Recombinant polypeptides encoded by polynucleotide sequences as described above may be readily prepared from the polynucleotide sequences using any of a variety of expression vectors known to those of ordinary skill in the art. Expression may be achieved in any appropriate host cell that has been transformed or transfected with at least one expression vector containing a DNA molecule that encodes a recombinant polypeptide. Suitable host cells include prokaryotes, yeast and higher eukaryotic cells, such as insect, mammalian or plant cells. Preferably, the host cells employed are *E. coli*, yeast, amphibian oocytes or a mammalian cell line such as COS, CHO, BHK, HEK 293, VERO, HeLa, MDCK, W138 or NIH 3T3 cells. Insect cell systems infected with recombinant virus expression vectors (for example, baculovirus) comprising a MCH1R polynucleotide provided herein may also be employed. Alternatively, a transgenic cell may be isolated from a transgenic animal.

Within certain embodiments, a MCH1R polypeptide is present within a membrane preparation. Such preparations are generated from transgenic cells that express a MCH1R polypeptide, using any standard procedure. Briefly, transfected host cell pellets are homogenized and centrifuged (e.g., 10 minutes at 48,000×g). The supernatant is discarded and the pellet is resuspended and homogenized again to generate an isolated membrane preparation. A more detailed protocol is provided in Example 3 herein. Preferably, isolated membranes have a MCH binding activity that is at least 2-fold greater, preferably 10-fold greater and more preferably at least 20-fold greater than that exhibited by control membranes isolated from a control cell (e.g., an untransfected cell of the same cell line used to prepare the recombinant cell or a cell transfected with a control vector that does not encode an MCH1R polypeptide). Preferred membrane preparations contain at least 0.1 pmol, 1 pmol or 5 pmol of MCH receptor polypeptide per mg of total membrane protein.

As noted above, MCH1R polypeptides may comprise additional sequences, such as antibody recognition sequences, that are not naturally present within a G protein-coupled receptor. A tagged fusion protein may be purified using an antibody specific for the tag (e.g., by affinity chromatography). Such purification procedures will typically require detergent extraction, and may result in a decrease in signal transduction activity. Such purified proteins are useful as antigens for the preparation of receptor-specific antibodies, in which case the retention of receptor signal transduction function is typically of little consequence.

Chimeric proteins may be prepared using standard recombinant methods. Briefly, convenient restriction sites may be incorporated into a MCH1R polynucleotide using site-directed mutagenesis. This allows the removal of polynucleotide encoding a particular domain. The domain to be inserted may be synthesized, and ligated to the digested MCH1R polynucleotide. The resulting polynucleotide encodes the chimeric polypeptide, and may be expressed using standard techniques, and as described herein. A similar process may be used to generate polypeptides that comprise a single MCH1R domain inserted into a different G protein-coupled receptor.

Expression Systems

Expression systems that may be used in the practice of certain aspects of the present invention include, but are not limited to, (a) insect cell systems infected with recombinant virus expression vectors (e.g., baculovirus) comprising one or more polynucleotides provided herein and (b) mammalian cell systems (e.g., COS, CHO, BHK, HEK 293, VERO, HeLa, MDCK, WI38 and NIH 3T3 cells) harboring recombinant expression constructs comprising one or more polynucleotides provided herein.

An expression vector is a vector for recombinant expression of a MCH1R polypeptide, comprising a MCH1R polynucleotide operatively linked to the necessary nucleotide sequences for expression (e.g., a suitable promoter and, if necessary, a terminating signal). A promoter is a nucleotide sequence (typically located 5' to the MCH receptor polynucleotide) that directs the transcription of adjacently linked coding sequences. A terminating signal may be a stop codon to end translation and/or a transcription termination signal. Additional regulatory element(s) (e.g., enhancer elements) may also be present within an expression vector. Such a vector is preferably a plasmid or viral vector. Techniques for incorporating DNA into such vectors are well known to those of ordinary skill in the art.

Preferably, an expression vector further comprises a selectable marker, which confers resistance to a selection. This allows cells to stably integrate the vector into their chromosomes and grow to form foci, which in turn can be cloned and expanded into cell lines. A number of selection systems can be used. For example, the hypoxanthine-guanine phosphoribosyltransferase, adenine phosphoribosyltransferase and herpes simplex virus thymidine kinase genes can be employed in hgprt⁻, aprt⁻ or tk⁻cells, respectively.

Also, anti-metabolite resistance can be used as the basis of selection for genes such as: dhfr, which confers resistance to methotrexate; gpt, which confers resistance to mycophenolic acid; neo, which confers resistance to the aminoglycoside G-418); hygro, which confers resistance to hygromycin; and puro, which confers resistance to puromycin.

Mammalian vectors should contain promoters, preferably derived from the genome of mammalian cells (for example, a metallothionein actin or phosphoglycerate kinase promoter) or from mammalian viruses (for example, the adenovirus late promoter, a CMV promoter and the vaccinia virus 7.5K promoter). In adenoviral expression vectors, the MCH receptor polynucleotide may be ligated to an adenovirus transcription/translation control complex such as the late promoter and tripartite leader sequence. Specific initiation signals (e.g., the ATG initiation codon and adjacent sequences such as ribosome binding sites) may also be required for efficient translation of inserted nucleic acid molecules. The efficiency of expression may be further enhanced by the inclusion of appropriate transcription enhancer elements, transcription terminators, etc. The recombinant gene may then be inserted in the adenovirus genome by in vitro or in vivo recombination. Insertion in a non-essential region of the viral genome (for example, region E1 or E3) will result in a recombinant virus that is viable and capable of expressing a MCH receptor polypeptide in infected cells. A preferred mammalian expression vector is the PCDNA3.1 vector (INVITROGEN, Carlsbad, Calif.).

Another preferred expression system is an amphibian oocyte system in which MCH1R RNA is introduced into an oocyte. Preferably the amphibian is a frog, most preferably the African clawed frog, *Xenopus laveis*. A preferred expression vector for expression in amphibian oocytes is the PBLUESCRIPT SK⁻ vector (STRATAGENE Cloning Systems, La Jolla, Calif.). Typically such vectors are used to generate MCH1R polypeptide-encoding RNAs in in vitro transcription systems, which RNAs are then injected into the oocytes to induce expression of the encoded protein.

An insect system utilizing a baculovirus such as *Autographa californica* nuclear polyhedrosis virus (AcNPV) can be used to express the MCH1R polypeptides provided herein. The virus grows in insect cells such as *Spodoptera frugiperda* cells. The coding sequence encoding the MCH1R polypeptide is typically inserted (e.g., ligated) into non-essential regions of the virus (for example into the polyhedrin gene) and placed under control of an AcNPV promoter (for example the polyhedrin promoter). Preferably, the successful introduction of the insert will result in inactivation of a viral gene. For example, when targeted into the polyhedrin gene, the successful incorporation of the insert will inactivate that gene and result in production of non-occluded recombinant virus (i.e., virus lacking the proteinaceous coat coded for by the polyhedrin gene). The resulting recombinant viruses are then used to infect insect cells, preferably *Spodoptera frugiperda* cells, in which the inserted coding sequence is expressed. A variety of kits for use in the preparation of an insect expression system are commercially available.

Host cells transformed or transfected with an expression vector comprising an MCH1R polynucleotide, and capable of expressing a MCH1R polypeptide, are further provided herein. Such cells may be prepared using standard transformation techniques. Stable expression is generally preferred, although transient expression systems may be suitable for certain uses. After the introduction of the vector (often following incubation in a non-selective medium to allow for recovery from the stress of vector introduction), engineered cells may be grown in a selective medium.

Assays

MCH1R polynucleotides and polypeptides may be used within a variety of assays to screen for and characterize compounds that modulate MCH receptor function. Such assays typically involve contacting a test compound with transfected host cells or isolated membranes prepared from such cells, and subsequently detecting (a) binding of the test compound to the cells or membranes (direct binding assays—e.g., via surface plasmon resonance, using a device available from BIAcor AB, Sweden); (b) an effect of the test compound on labeled ligand (e.g., radiolabeled MCH) binding to the cells or membranes (competitive binding assays); or (c) an effect on a cellular receptor response to MCH (functional assays). Test compounds may be any substance, but are preferably small organic, non-peptide molecules. Active compounds identified using such assays are useful, for example, as tools for receptor mapping and as pharmaceutical agents.

One suitable competitive binding assay is provided within Example 4. In such an assay, a test compound is used as a cold displacer. Briefly, a MCH1R polypeptide-containing membrane preparation (e.g., prepared from transfected HEK293 cells) is contacted (incubated) with labeled (e.g., $^{125}$I) MCH and unlabeled test compound. Unbound MCH is then removed (e.g., by washing) and remaining bound label is detected. Incubation with a compound that detectably modulates MCH binding to MCH receptor will result in a decrease or increase in the amount of label bound to the MCH receptor preparation, relative to the amount of label bound in the absence of the compound. Preferably, such a compound will exhibit a $K_i$ at an MCH receptor of less than 1 micromolar, more preferably less than 500 nM, 100 nM, 20 nM or 10 nM, within a ligand binding assay performed as described in Example 4.

Functional assays use transfected host cells as substrates and measure cellular responses to contact with a test compound. Within such assays, a compound may act as an agonist, mediating a cell-based response when contacted with a cell-surface MCH receptor, or as an antagonist, inhibiting the response of cell-surface MCH receptor to an MCH receptor agonist (e.g., MCH). A representative functional assay is set forth below as Example 5. Within $Ca^{2+}$ mobilization assays, MCH receptor modulating activity of a compound is detected by: (a) incubating (i.e., contacting) transgenic (e.g., transformed or transfected) cells with a compound; (b) detecting a level of $Ca^{2+}$ in the contacted cells; and (c) comparing the detected level of calcium with a level of $Ca^{2+}$ detected in control cells that are incubated in the absence of test compound. Preferably, within such assays, the transgenic cells are initially contacted with an indicator of intracellular $Ca^{2+}$ concentration, such as Fluo-3 Calcium Sensitive Dye (Molecular Probes; Eugene, Oreg.) and then washed. The compound is then contacted with the washed cells, and the level of calcium is detected by quantifying $Ca^{2+}$ concentration-dependant changes in the properties of the indicator of intracellular $Ca^{2+}$. The level of calcium detected in the presence of test compound is preferably at least 2-fold greater than the level detected in the absence of test compound (i.e., in control cells that are contacted with the indicator of intracellular $Ca^{2+}$ concentration, but not with the test compound).

MCH receptor antagonist activity may also be detected using calcium mobilization assays performed in the presence of a known MCH receptor agonist (e.g., MCH). MCH receptor agonist is preferably added to test and control cells just prior to detecting intracellular $Ca^{2+}$ concentration. Preferably, the concentration of intracellular $Ca^{2+}$ in the agonist-contacted test cell is significantly less (to the $p \leq 0.05$ level, as measured using a parametric test of statistical significance) than the concentration of intracellular $Ca^{2+}$ in the agonist-contacted control cell.

Compounds identified using such assays may be used for treating diseases and disorders associated with MCH receptor activation, such as eating disorders (e.g., obesity and bulimia nervosa), sexual disorders, diabetes, heart disease and stroke. Patients may include humans, companion animals (such as dogs) and livestock animals.

The following Examples are offered by way of illustration and not by way of limitation.

EXAMPLES

Example 1

MCH1R Polynucleotide Preparation

This Example illustrates the isolation of representative MCH1R polynucleotides.

A. Monkey MCH1R

RNA was isolated from Cynomolgus macaque hypothalamus using Trizol Reagent (Life Technologies, Gaithersburg, Md.). cDNA was prepared using random primers and Reverse Transcriptase (Life Technologies) according to the manufacturer's instructions.

Cynomolgus macaque MCH1R cDNA was obtained using PCR, with the following primers:
5' Forward Outer Primer GAGCAGGCGA CCGGCACTGG CTGG (SEQ ID NO:7)
3' Reverse Primer GGAGGTGTGC AGGGTGGCAG GGGAAGTA (SEQ ID NO:8)

PCR was performed using the Advantage-GC cDNA PCR Kit (Clontech Laboratories Palo Alto, Calif.) in 50 microliter reactions containing: 10 microliters GC Melt, 10 microliters 5× PCR reaction buffer, 1 microliter 50× dNTP Mix (10 mM each), 12.5 pmoles forward and reverse primers, 1 microliter Advantage-GC cDNA Polymerase Mix (50×), 1 microliter Cynomolgus macaque RT product. Conditions for touchdown PCR were as follows:

| | |
|---|---|
| | 94° C. - 3 minutes |
| 20 cycles: | 94° C. - 30 seconds |
| | 60° C. to 50° C. in 0.5° C. |
| | intervals for 20 rounds - 30 seconds |
| | 68° C. - 60 seconds |
| 20 cycles: | 94° C. - 30 seconds |
| | 50° C. - 30 seconds |
| | 68° C. - 60 seconds |
| 4° C. | |

The full length PCR product was initially cloned into the vector pGEM-T (Invitrogen, Carlsbad, Calif.). The cDNA was reamplified using a forward primer engineered to include an optimal translation initiation site (Kozak sequence). A cDNA expression cassette fragment encoding the monkey MCH1R was blunt end ligated into the PCR-SCRIPT vector (STRATAGENE, La Jolla, Calif.). The receptor sequence was excised from this vector using EcoRI and Not I and subcloned into the EcoRI/Not I site of PCDNA3.1 (INVITROGEN Corp.; Carlsbad, Calif.).

A receptor cDNA expression cassette thus cloned from cynomolgus macaque total hypothalamic cDNA (and referred to herein as cynMacMCH1R, SEQ ID NO:1) was subcloned into the PCDNA3.1 expression vector to create the MCH1 receptor expression vector, CynMacMCH1RDNA. This cynMacMCH1R cDNA expression cassette has been also been cloned into pCR-Script, and pBacPac9 vectors. The nucleotide and amino acid sequences of cynomolgus macaque MCH1R are shown in SEQ ID NO:1 and 2, respectively.

The MCH1R 5' extension was cloned using RACE. Cynomolgus macaque temporal cortex total RNA was used as a template and RACE was performed using the FirstChoice™ RLM-RACE kit (Ambion, Austin, Tex.) according to the manufacturer's instructions, with the outer reverse primer corresponding to nucleotides 503–478 of SEQ ID NO:1 (CACAGGAGGCAGATCAC-CAGGGTGGC; SEQ ID NO:57) and the inner reverse primer corresponding to nucleotides 393–372 of SEQ ID NO:1 (GGTGCTGGTGAACTGA CTATTG; SEQ ID NO:58). PCR conditions were as follows:

|  |  |
|---|---|
|  | 94° C. - 3 minutes |
| 35 cycles: | 94° C. - 30 seconds |
|  | 58° C. - 30 seconds |
|  | 68° C. - 30 seconds |
|  | 68° C. - 7 minutes |
| 4° C. |  |

The sequence of the 5' region is shown in SEQ ID NO:53, with the encoded amino acid sequence in SEQ ID NO:54. The long form of MCH1R, which includes the 5' extension, is shown in SEQ ID NO:55 (DNA sequence) and SEQ ID NO:56 (amino acid sequence). Alignments of the monkey MCH1R sequences with other MCH1R sequences are shown in FIGS. 1 (A and B) and 2.

B. Human MCH1R/human NPY1 Receptor Intracellular Loop 3 Chimera

Human MCH1R (SEQ ID NO:5) was cloned as a PCR product from a Gibco Human Brain library (Life Technologies; Rockville, Md.) as described above using the following primers:

Forward 5'CCACCATGGACCTGGAAGCCTCG (SEQ ID NO:31)

Reverse 5'AGGGTGGCAGGGGAAGTATC (SEQ ID NO:32)

The human MCH1R cDNA (SEQ ID NO:5) was digested with BamH I (base 689–694) and BstE II (bases 759–765) to remove the IC3 domain. This corresponds to amino acids 230–255 in SEQ ID NO:6. The IC3 domain from the human NPY1 receptor cDNA (SEQ ID NO:9, bases 706–779 and corresponding to amino acids 236–260 of SEQ ID NO:10) was constructed from two complementary oligonucleotides (SEQ ID NO:14 and SEQ ID NO:15) which contain the BamH I and BstE II sites. The two oligonucleotides were heated to 95° C., allowed to anneal, and are inserted into the digested MCH1R to yield the sequence the human MCH1R/human NPY1 receptor Intracellular Loop 3 chimera (SEQ ID NO:17). The corresponding amino acid sequence is given as SEQ ID NO:18. The entire sequence was subcloned into pcDNA 3.1 plus to yield SEQ ID NO:21.

C. Human MCH1R/human NPY 1 Receptor C-Terminal Chimera

To exchange the human NPY1 receptor C-terminal with that of the human MCH1R, a BspE I restriction site was introduced into both receptors. In the human MCH1R (SEQ ID NO:5) a silent C to G point mutation was made at base 957 to produce SEQ ID NO:16. For the human NPY1 receptor C-terminal, base 983 was mutated from A to G which results in a Q to R amino acid change at 328 of SEQ ID NO:10. A PCR fragment (SEQ ID NO:13) generated with SEQ ID NO:9 as a template using primers SEQ ID NO:11 and SEQ ID NO:12 (SEQ ID NO:12 is mainly comprised of vector sequence) was amplified. This PCR fragment was subcloned BspE I to Not I into the mutated human MCH1R (SEQ ID NO:16) to form the human MCH1R/human NPY1 receptor C-terminal chimera (SEQ ID NO:19). The corresponding amino acid sequence is given as SEQ ID NO:20. The final sequence in pcDNA 3.1 plus is given as SEQ ID NO:21.

D. Human MCH1R/human Beta Adrenergic Receptor C-terminal Chimera

The C-terminal sequence from the human beta-2 adrenergic receptor (SEQ ID NOs:23 and 24) was also used form a human MCH1R/beta adrenergic receptor C-terminal chimera. Primers (SEQ ID NOs:25 and 26) were used to amplify a PCR product from the human beta-2 adrenergic receptor (SEQ ID NO:23) which includes a BspE I site on the 5' end and an Xba I site on the 3' end. This fragment was introduced BspE I to Xba I into the human MCH1R mutated at base 957 as discussed above (SEQ ID NO:16) to form the Human MCH1R/human beta adrenergic receptor C-terminal chimera (SEQ ID NO:27). The corresponding amino acid sequence is given as SEQ ID NO:28. The final sequence in pcDNA 3.1 plus is given as SEQ ID NO:29.

It will be apparent that similar cloning procedures can be used to generate the corresponding chimeras based on the monkey MCH1R sequence and/or substituting domains from other G protein-coupled receptors.

Example 2

Preparation of Host Cells Expressing MCH1R Polypeptides

This Example illustrates the expression of representative MCH1R polynucleotides in host cells.

HEK 293 cells were stably transfected via standard calcium phosphate precipitation procedures with the Cyn-MacDNA monkey MCH1 receptor expression vector described in Example 1.

For transient transfection, cells were grown to confluency at 37° C., 5% $CO_2$, for approximately 48–72 hours in DMEM high glucose culture medium (catalog #10–017-CV, MEDIATECH, Herndon, Va.) supplemented with 10% fetal bovine serum, 25 mM HEPES. Cells could then be used directly within assays. For stable expression, cells were grown under the conditions described above (with the addition of 500 μg/ml G418) for 2–3 weeks. Single selected colonies were then chosen to generate a stable cell line.

CHO (Chinese Hamster Ovary) cells were also transfected via standard calcium phosphate precipitation procedures with the MCH1R expression vector. For transient transfection, cells were grown to confluency at 37° C., 5% $CO_2$, approximately 48–72 hours, in Ham's F12 culture medium (catalog #10-080-CV, MEDIATECH, Herndon, Va.) supplemented with 10% fetal bovine serum, 25 mM HEPES. Cells could then be used directly within assays. For stable expression, cells were grown under the conditions described above (with the addition of 500 μg/ml G418) for 2–3 weeks. Single selected colonies were then chosen to generate a stable cell line.

Example 3

Preparation of Isolated Membranes

This Example illustrates the preparation of isolated membranes comprising MCH1R polypeptides, for use within a variety of binding and activity assays.

Transfected HEK 293 cell pellets stored frozen at −80° C. are thawed by addition of wash buffer (25 mM Hepes with 1.0 mM $CaCl_2$, 5.0 mM $MgCl_2$, 120 mM NaCl, PH 7.4) and homogenized for 30 seconds using a BRINKMAN POLYTRON, setting 5. Cells are centrifuged for 10 minutes at 48,000×g. The supernatant is discarded and the pellet is resuspended in fresh wash buffer, and homogenized again. The protein concentration of the resulting membrane preparation is measured using the Bradford protein assay (Bio-Rad Laboratories, Hercules, Calif.). By this measure, a 1-liter culture of cells typically yields 50–75 mg of total membrane protein.

Example 4

MCH1R Ligand Binding Assays

This Example illustrates the use of MCH1R-containing membranes within binding assays to monitor the ability of cells expressing MCH receptors to bind MCH or to screen for MCH1R agonists and antagonists.

Purified membranes from HEK 293 cells expressing MCH1R are prepared as described above. The membrane homogenate is centrifuged as before and resuspended to a protein concentration of 333 µg/ml in binding buffer (Wash buffer+0.1% BSA and 1.0 µM final conc. phosphoramidon) for an assay volume of 50 µg membrane protein/150 µl binding buffer. Phosphoramidon is from SIGMA BIOCHEMICALS, St. Louis, Mo. (cat# R-7385).

Ligand binding assays are performed at room temperature by combining 150 µl of MCH1R-containing membranes in binding buffer, prepared as described above, 50 µl $^{125}$I-Tyr MCH in binding buffer and 50 µl binding buffer. $^{125}$I-Tyr MCH (specific activity=2200 Ci/mMol) is purchased from NEN, Boston, Mass. (Cat # NEX 373) and is diluted in binding buffer to provide a final assay concentration of 30 pM.

Competition binding assays for screening test compounds are performed at room temperature in Falcon 96 well round bottom polypropylene plates. To each assay well is added 150 µl of MCH1R-containing membranes in binding buffer, prepared as described above, 50 µl $^{125}$I-Tyr MCH in binding buffer, 50 µl binding buffer and 2 µl test compound in DMSO.

Non-specific binding is defined as the binding measured in the presence of 1 µM unlabeled MCH. MCH is purchased from BACHEM U.S.A., King of Prussia, Pa. (cat # H-1482). To each assay well used to determine non-specific MCH binding is added: 150 µl of MCH1R-containing membranes in binding buffer, 50 µl $^{125}$I-Tyr MCH in binding buffer, unlabeled MCH in 25 µl binding buffer, and 25 µl binding buffer.

Assay plates are incubated for 1 hour at room temperature. Membranes are harvested onto WALLAC glass fiber filters (PERKIN-ELMER, Gaithersburg, Md.) which are pre-soaked with 1.0% PEI (polyethyleneimine) for 2 hours prior to use. Filters are allowed to dry overnight then counted in a WALLAC 1205 BETA PLATE counter after addition of WALLAC BETA SCINT scintillation fluid.

For saturation binding the concentration of $^{125}$I-Tyr MCH is varied from 7–1,000 pM. Typically 11 concentration points are collected per saturation binding curve. Equilibrium binding parameters are determined by fitting the allosteric Hill equation to the measured values with the aid of the computer program FitP™ (BIOSOFT, Ferguson, Mo.).

Example 5

MCH 1 R Calcium Mobilization Assay

This Example illustrates the use of MCH1R-expressing cells within functional assays to monitor the response of cells expressing MCH receptors to MCH or to screen for MCH1R agonists and antagonists.

CHO or HEK 293 cells stably transfected with an MCH1R receptor expression vector as described above are grown to a density of 30,000 cells/well in FALCON black-walled, clear-bottomed 96-well plates (#3904, BECTON-DICKINSON, Franklin Lakes, N.J.). Prior to running the assay the culture medium is emptied from the 96 well plates. Fluo-3 calcium sensitive dye (Molecular Probes, Eugene, Oreg.) is added to each well (dye solution: 1 mg FLUO-3 AM, 440 µl DMSO and 440 µl 20% pluronic acid in DMSO; diluted 8.8 µl/ml with KRH; 50 µl diluted solution added per well). Plates are covered with aluminum foil and incubated at 37° C. for 1–2 hours. After the incubation the dye solution is emptied from the plates, cells are washed once in 100 µl KRH buffer (0.05 mM KCl, 0.115 M NaCl, 9.6 mM $NaH_2PO_4$, 0.01 mM $MgSO_4$, 1 mM probenecid (Sigma), 25 mM HEPES, pH 7.4) to remove excess dye; after washing 80 µl KRH buffer is added to each well.

In order to measure the ability of a test compound to antagonize the response of cells expressing MCH1R to MCH, the $EC_{50}$ of MCH is first determined. An additional 20 µl of KRH buffer and 1 µl DMSO is added to each well of cells, prepared as described immediately above. 100 µl human MCH in KRH buffer is automatically transferred by a FLIPR™ plate reader (Molecular Devices, Sunnyvale, Calif.) to each well, and fluorescence response is monitored by excitation at 480 nM and emission at 530 nM. An 8-point concentration response curve, with final MCH concentrations of 1 nM to 3 µM, is used to determine MCH $EC_{50}$.

Test compounds are dissolved in DMSO, diluted in 20 µl KRH buffer, and added to cells prepared as described above. The 96 well plates containing prepared cells and test compounds are incubated in the dark, at room temperature for 0.5 to 6 hours. It is important that the incubation not continue beyond 6 hours. Just prior to determining the fluorescence response, 100 µl human MCH diluted in KRH buffer to $2 \times EC_{50}$ is automatically added by the FLIPR instrument to each well of the 96 well plate for a final sample volume of 200 µl and a final MCH concentration of $EC_{50}$. The final concentration of test compounds in the assay wells is between 1 µM and 5 µM. Typically cells exposed to one $EC_{50}$ of MCH exhibit a fluorescence response of about 10,000 Relative Fluorescence Units. Antagonists of the MCH receptor exhibit a response that is significantly less than that of the control cells to the $p \leq 0.05$ level, as measured using a parametric test of statistical significance. Typically, antagonists of the MCH receptor decrease the fluorescence response relative to control cells by about 20%, preferably by about 50%, and most preferably by at least 80% as compared to matched control.

What is claimed is:

1. An isolated polynucleotide encoding a polypeptide, wherein the polypeptide comprises at least amino acid residues 2 to 353 of SEQ ID NO:2.

2. The isolated polynucleotide according to claim 1, wherein the polynucleotide comprises at least 90 consecutive nucleotides of SEQ ID NO:55.

3. The isolated polynucleotide according to claim 2, wherein the polynucleotide comprises at least nucleotides 28–220 of SEQ ID NO:1.

4. An isolated polynucleotide encoding a polypeptide, wherein the polypeptide comprises the sequence recited in SEQ ID NO:2 in which the third intracellular loop or C-terminal domain is replaced with a corresponding domain of MCH2R, NPY$_1$ receptor or beta-2-adrenergic receptor, and wherein the polypeptide binds melanin concentrating hormone.

5. The polynucleotide according to claim 4, wherein the polypeptide has a sequence recited in any one of SEQ ID NOs:42, 44, 46, 50 and 52.

6. An expression vector comprising a polynucleotide according to claim 1.

7. The expression vector according to claim 6, wherein the vector is a plasmid.

8. The expression vector according to claim 6, wherein the vector is a viral vector.

9. An isolated host cell transformed or transfected with an expression vector according to claim 6.

10. The isolated transformed or transfected host cell according to claim 9, wherein the cell is a mammalian cell.

11. The isolated transformed or transfected host cell according to claim 9, wherein the cell is an oocyte.

12. A cell membrane preparation isolated from a transformed or transfected host cell according to claim 9, wherein the membrane comprises a polypeptide that comprises at least amino acid residues 2 to 353 of SEQ ID NO:2.

13. The cell membrane preparation according to claim 12, wherein the cell membrane preparation exhibits MCH1R ligand binding activity that is at least 2-fold greater than MCH1R ligand binding activity exhibited by a control membrane preparation isolated from host cells that do not contain an expression vector encoding a polypeptide that comprises at least amino acid residues 2 to 353 of SEQ ID NO:2.

14. The isolated polynucleotide according to claim 3, wherein the polynucleotide comprises SEQ ID NO:1.

15. The isolated polynucleotide according to claim 1, wherein the polypeptide comprises at least amino acid residues 2 to 422 of SEQ ID NO:56.

16. The isolated polynucleotide according to claim 15, wherein the polynucleotide comprises SEQ ID NO:55.

17. An expression vector comprising a polynucleotide according to claim 4.

18. The expression vector according to claim 17, wherein the vector is a plasmid.

19. The expression vector according to claim 17, wherein the vector is a viral vector.

20. An isolated host cell transformed or transfected with an expression vector according to claim 17.

21. The isolated transformed or transfected host cell according to claim 20, wherein the cell is a mammalian cell.

22. The isolated transformed or transfected host cell according to claim 20, wherein the cell is an oocyte.

23. A cell membrane preparation isolated from a transformed or transfected host cell according to claim 20, wherein the membrane comprises a polypeptide that comprises the sequence recited in SEQ ID NO:2 in which the third intracellular loop or C-terminal domain is replaced with a corresponding domain of MCH2R, NPY$_1$ receptor or beta-2-adrenergic receptor.

24. The cell membrane preparation according to claim 23, wherein the cell membrane preparation exhibits MCH1R ligand binding activity that is at least 2-fold greater than MCH1R ligand binding activity exhibited by a control membrane preparation isolated from host cells that do not contain an expression vector encoding a polypeptide that comprises SEQ ID NO:2 in which the third intracellular loop or C-terminal domain is replaced with a corresponding domain of MCH2R, NPY1 receptor or beta-2-adrenergic receptor.

* * * * *